US012642856B2

(12) United States Patent
Gray et al.

(10) Patent No.: US 12,642,856 B2
(45) Date of Patent: Jun. 2, 2026

(54) DEGRADERS OF HEPATITIS C VIRUS NS3/4A PROTEIN

(71) Applicants: DANA-FARBER CANCER INSTITUTE, INC., Boston, MA (US); PRESIDENT AND FELLOWS OF HARVARD COLLEGE, Cambridge, MA (US)

(72) Inventors: Nathanael S. Gray, Boston, MA (US); Tinghu Zhang, Boston, MA (US); Priscilla Yang, Boston, MA (US); Melissanne De Wispelaere, Cambridge, MA (US); Guangyan Du, Jamaica Plain, MA (US)

(73) Assignees: DANA-FARBER CANCER INSTITUTE, INC., Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 1310 days.

(21) Appl. No.: 17/280,075

(22) PCT Filed: Sep. 26, 2019

(86) PCT No.: PCT/US2019/053148

§ 371 (c)(1),
(2) Date: Mar. 25, 2021

(87) PCT Pub. No.: WO2020/069125

PCT Pub. Date: Apr. 2, 2020

(65) Prior Publication Data

US 2021/0338825 A1 Nov. 4, 2021

Related U.S. Application Data

(60) Provisional application No. 62/738,326, filed on Sep. 28, 2018.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC ..... A61K 47/55; A61K 47/545; C07D 401/14
See application file for complete search history.

(56) References Cited

U.S. PATENT DOCUMENTS

2007/0207949 A1 9/2007 Ghosal et al.
2011/0195912 A1 8/2011 Riggs-Sauthier et al.
2018/0228907 A1 8/2018 Crew et al.

FOREIGN PATENT DOCUMENTS

WO 2017/185036 A1 10/2017

OTHER PUBLICATIONS

Shirakura, et al., "E6AP Ubiquitin Ligase Mediates Ubiquitylation and Degradation of Hepatitis C Virus Core Protein", Journal of Virology, 2007, 81(3):1174-1185.

(Continued)

*Primary Examiner* — Savitha M Rao
*Assistant Examiner* — Andrew P Lee
(74) *Attorney, Agent, or Firm* — ArentFox Schiff LLP; Daniel W. Clarke; Shawn P. Foley

(57) ABSTRACT

Disclosed are bifunctional compounds (degraders) that target hepatitis C virus (HCV) NS3/4A for degradation. Also disclosed are pharmaceutical compositions containing the degraders and methods of using the compounds to treat HCV infection and HCV-associated diseases or disorders.

15 Claims, 11 Drawing Sheets

(56) References Cited

OTHER PUBLICATIONS

De Wispelaere et al., "Small molecule degraders of the hepatitis C virus protease reduce susceptibility to resistance mutations," Nature Communications, 2019, vol. 30, No. 3468, pp. 1-11.
Bekes, M., et al. "PROTAC targeted protein degraders: the past is prologue", Nature Reviews Drug Discovery, 2022, vol. 21, pp. 181-200.
Bondeson, D. P., et al., "Lesson in PROTAC design from selective degradation with a promiscuous warhead", Cell Chem. Biol., 2018, vol. 25, No. 1, pp. 78-87.
Li, X., et al., "Proteolysis-targeting chimera (PROTAC) for targeted protein degradation and cancer therapy", Journal of Hematology & Oncology, 2020, vol. 13, No. 50, 14 pages.
Tan, L. et al., "When Kinases Meet PROTACs", Chin. J. Chem., 2018, vol. 36, pp. 971-977.
Nandave, M. et al., "PROTAC-mediated protein degradation: A paradigm shift in cancer therapeutics", Springer, 2024, 400 pages.
Sobierajski, et al., "The impact of E3 ligase choice on PROTAC effectiveness in protein kinase degradation", Drug Discovery Today, 2024, vol. 29, No. 7, 20 pages.

DEGRADERS OF HEPATITIS C VIRUS NS3/4A PROTEIN

RELATED APPLICATIONS

This application is a national stage application, filed under 35 U.S.C. § 371, of International Application No. PCT/US2019/053148, filed Sep. 26, 2019, which claims the benefit of priority under 35 U.S.C. § 119 (e) to U.S. Provisional Application No. 62/738,326, filed on Sep. 28, 2018, each of which is incorporated herein by reference in its entirety.

GOVERNMENT LICENSE RIGHTS

The invention was made with government support under grant number U19AI109740 awarded by the National Institutes of Health. The government has certain rights in the invention.

BACKGROUND OF THE INVENTION

Hepatitis C virus (HCV) infection is one of the leading causes of chronic liver disease worldwide. It is estimated that about 185 million individuals globally have anti-HCV antibodies and of these 130-170 million are chronic carriers of the infection. (Mohd Hanafiah et al., Hepatology 57:1333-42 (2013); Thomas, Nat. Med. 19:850-58 (2013)). Hepatitis C infection can also lead to liver cirrhosis. Furthermore, it is the number one cause of liver cancer.

HCV has a single-stranded positive-sense RNA molecule, which encodes a single large polyprotein. The polyprotein undergoes proteolytic cleavage by cellular and viral proteases, which process the polyprotein into 10 structural- and non-structural proteins. The NS3/4A protein complex of HCV has important protease and helicase activities and together with NS4B, NS5A and NS5B, participates in the replication module. The HCV NS3/4A protease is essential for HCV replication by cleaving the HCV polyprotein (Moradpour et al., Nat. Rev. Microbiol. 5:453-63 (2007)). HCV NS3/4A protease also cleaves cellular proteins like TC-PTP (T cell protein tyrosine phosphatase) and enhances EGF (epithelial growth factor) induced signal transduction, which is essential for viral replication (Brenndorfer et al., Hepatol. 49:1810-20 (2009)). Furthermore, NS3/4A blocks innate immune response signal transduction pathways by cleaving TRIF (Toll-interleukin-1 receptor domain-containing adaptor inducing IFN) and CARDIF proteins (CARD adaptor inducing IFN-β; and also MAVS, VISA and IPS-1), which are important for TLR (Toll-like receptor) and RIG-I (retinoic acid inducible gene-I) mediated signaling cascades. (Li et al., Proc. Natl. Acad. Sci. USA 102:2992-97 (2005); Heim J. Hepatol. 58:564-74 (2013); Li et al., Proc. Natl. Acad. Sci. USA 102:17717-22 (2005); Meylan et al., Nature 437:1167-72 (2005); Sklan et al., Nat. Rev. Gastroenterol. Hepatol. 6:217-27 (2009)). The inactivation of CARDIF and TRIF leads to reduced IFN production and impaired host defenses which may promote persistent HCV infection. (Bellecave et al., Hepatol. 51:1127-36 (2010)).

Until 2011, the gold standard for HCV treatment had been the combination of PEGylated interferon-α (PEG-IFNα) and ribavirin (RBV). The addition of direct acting anti-virals (DAAs, e.g., protease and polymerase inhibitors) in conjunction with PEG-IFNα and ribavirin treatment has shown improved sustained virologic responses. (Poordad et al., N. Engl. J. Med. 364:1195-1206 (2011)). Two oral DAAs, telaprevir (INCIVIK™) and boceprevir (VICTRELIS™) were approved by the FDA in 2011. Used in combination with PEG-IFN and RBV in patients with HCV genotype 1 infection, telaprevir and boceprevir produced sustained virological response (SVR) rates as high as 70%. However, both were withdrawn from the market, in 2014 and 2015, respectively, in favor of superior DAAs, including simeprevir (OLYSIO™) and sofosbuvir (SOVALDI™). (Kish et al., Pharmacy & Therapeutics 42(5):316-329 (2017)).

SUMMARY OF THE INVENTION

A first aspect of the present invention is directed to a bifunctional compound (also referred to herein as a "degrader" or "PROTAC"), which has a structure represented by formula (I):

(I)

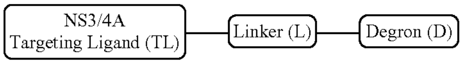

, wherein the targeting ligand represents a moiety that binds hepatitis C virus (HCV) NS3/4A protein, the degron represents a moiety that binds an E3 ubiquitin ligase, and the linker represents a moiety that covalently connects the degron and the targeting ligand, or a pharmaceutically acceptable salt or stereoisomer thereof.

A second aspect of the present invention is directed to a pharmaceutical composition containing a therapeutically effective amount of a bifunctional compound of formula I, or a pharmaceutically acceptable salt or stereoisomer thereof, and a pharmaceutically acceptable carrier.

A further aspect of the invention is directed to a method of treating HCV infection that includes administering a therapeutically effective amount of an inventive bifunctional compound or a pharmaceutically acceptable salt or stereoisomer thereof, to a subject in need thereof. In some embodiments, subjects with HCV infection have contracted liver disease (e.g., hepatitis, cirrhosis and liver cancer), in which case the methods may still be effective in treating the underlying and persistent HCV infection and may result in a more positive (e.g., stable) clinical outcome.

Further aspects of the present invention are directed to methods of making the bifunctional compounds.

Without intending to be bound by any particular theory of operation, the bifunctional compounds of formula (I) of the present invention are believed to degrade NS3/4A protein of HCV via the cell's ubiquitin/proteasome system, whose function is to routinely identify and remove damaged proteins. The degron functional moiety recruits the E3 ubiquitin ligase to tag NS3/4A (which is bound by the targeting ligand functionality) for ubiquitination and degradation through the proteasome, which is a large endogenous complex that degrades the ubiquitinated protein into small peptide fragments. After destruction of a NS3/4A molecule, the degrader is released and continues to be active. Effective intracellular concentrations of the degraders may be significantly lower than for small molecule NS3/4A inhibitors. Further, chemical degradation of NS3/4A may have significant advantages over protease inhibition by NS3/4A inhibitors and thus more likely clinical applicability due to abrogation of HCV. Thus, by engaging and exploiting the body's own natural protein disposal system, the bifunctional compounds of the present invention may represent a potential improvement over existing HCV treatment modalities such as DAAs and peg-IFNα/ribavirin.

In certain embodiments, the targeting ligand is telaprevir or a similar peptidomimetic. Thus, the invention may exploit a drug that was no longer believed to be effective for treating HCV infections and uses it in a very different way, i.e., as a targeting ligand moiety of the bifunctional compounds of the present invention. Unexpectedly, the inventive bifunctional degraders were superior at mediating antiviral activity against resistant viruses that arise upon treatment with direct-acting antivirals.

BRIEF DESCRIPTION OF THE DRAWINGS

FIG. 3A shows that Lenalidomide inhibited degradation of NS3 by inventive compounds 1, 3, and 4, indicating competition for E3 ligase. FIG. 3B shows that Lenalidomide inhibited degradation of NS3 by inventive compound 13. Compounds 20 and 22 are negative controls and showed no significant degradation of NS3 in the presence or absence of lenalidomide.

DETAILED DESCRIPTION OF THE INVENTION

Figure 1:
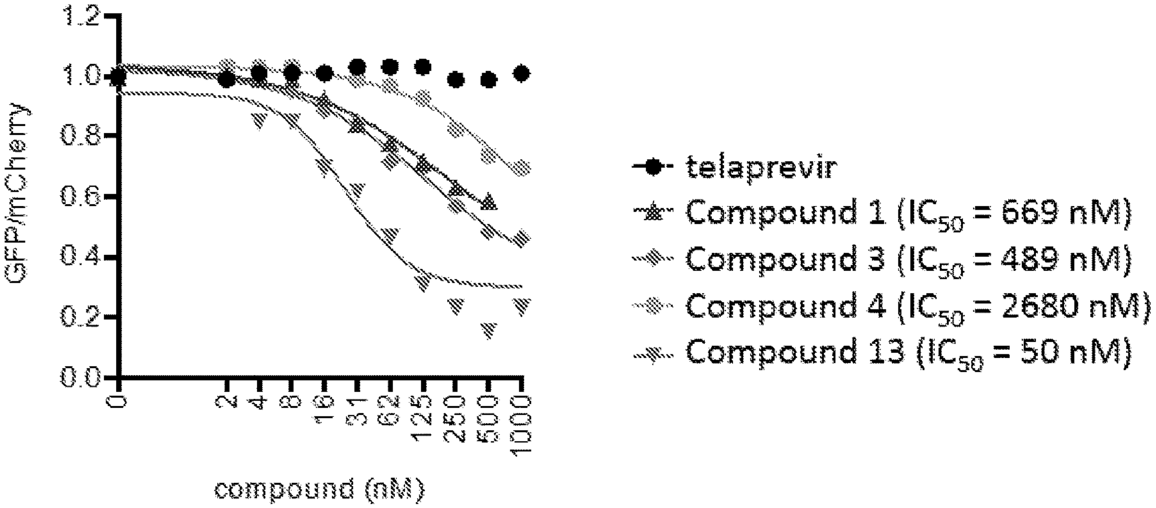
FIG. 1 is a graph showing transient cellular HCV NS3 degradation by treatment with compounds 1 ($IC_{50}$=669 nM), 3 ($IC_{50}$=489 nM), 4 ($IC_{50}$=2680 nM), and 3 ($IC_{50}$=50 nM).

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a" "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula —C(O)H. The terms "C(O)" and C═O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen.

Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carboxylic acid" is represented by the formula —C(O)OH, and a "carboxylate" is represented by the formula —C(O)O—.

As used herein, the term "ester" is represented by the formula —OC(O)$Z^1$ or —C(O)O$Z^1$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —$S(O)_2Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —$S(O)_2NH_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_5$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), haloalkyl (e.g., $CF_3$), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, sulfonyl, substituted sulfonyl, urea, substituted urea, carbamate, substituted carbamate, amino acid, and peptide groups.

The term "binding" as it relates to interaction between the targeting ligand and the targeted protein, which is NS3/4A, typically refers to an inter-molecular interaction that is substantially specific (or "selective") in that binding of the targeting ligand with other proteinaceous entities present in the cell is functionally insignificant. The present bifunctional compounds preferentially bind and recruit NS3/4A for targeted degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bifunctional compounds (also referred to herein as a "degrader" or "PROTAC"), of the present invention have a structure represented by formula (I):

(I)

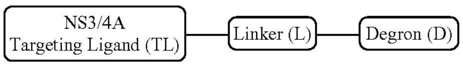

, wherein the targeting ligand represents a moiety that binds hepatitis C virus (HCV) NS3/4A protein, the degron represents a moiety that binds an E3 ubiquitin ligase, and the linker represents a moiety that covalently connects the degron and the targeting ligand, or a pharmaceutically acceptable salt or stereoisomer thereof.

NS3/4A Targeting Ligands

In some embodiments, the NS3/4A targeting ligand is telaprevir (formerly marketed as INCIVEK™), or a peptidomimetic analog thereof. Telaprevir is also known as (1S,3aR,6aS)-2-[(2S)-2-({(2S)-2-cyclohexyl-2-[(pyrazin-2-ylcarbonyl)amino]acetyl}amino)-3,3-dimethylbutanoyl]-N-[(3S-1-(cyclopropylamino)-1,2-dioxohexan-3-yl]-3,3a,4,5,6,6a-hexahydro-1H-cyclopenta[c]pyrrole-1-carboxamide. The structure of telaprevir is shown below:

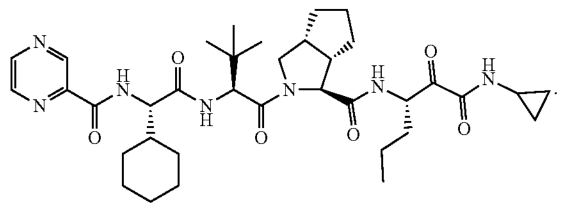

(Telaprevir)

Thus, in some embodiments, the NS3/4A targeting ligand has a structure represented by structure TL1:

(TL1)

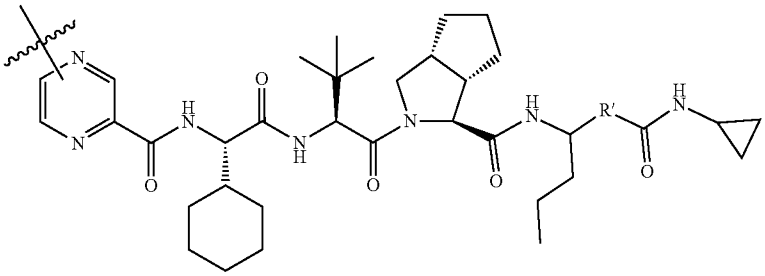

wherein R' is CH—OH or C═O, or a stereoisomer thereof.

In some embodiments, the NS3/4A targeting ligand has a structure represented by any one of structures TL1a-TL1d:

(TL1a)

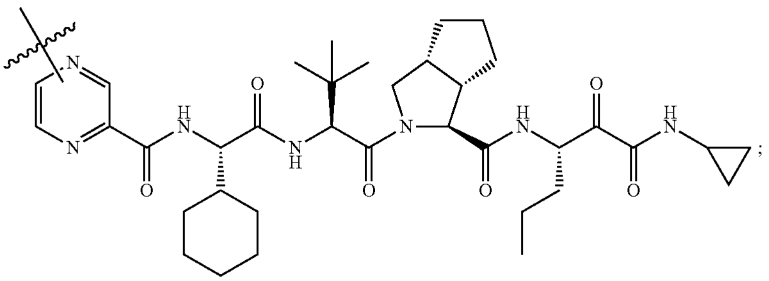

(TL1b)

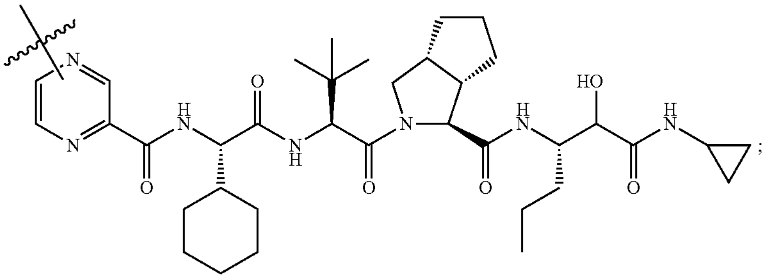

-continued (TL1c)

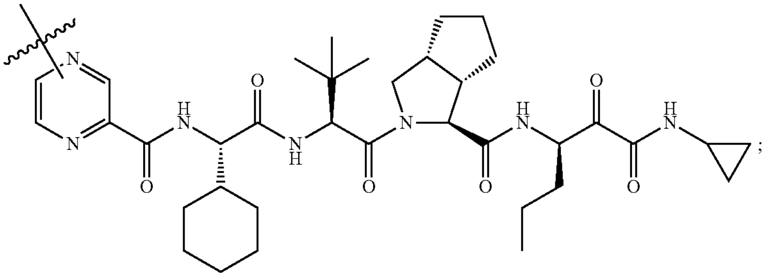

; and (TL1d)

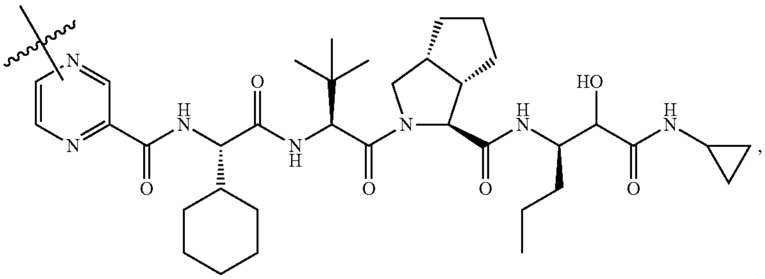

, or a stereoisomer thereof.

Other peptidomimetic analogs of Telaprevir that may be useful as NS3/4A targeting ligands are described in U.S. Pat. Nos. 7,820,671, 8,431,615 and 8,529,882.

Thus, in some embodiments, the bifunctional compounds of the present invention have a structure represented by formula dg1:

(dgl)

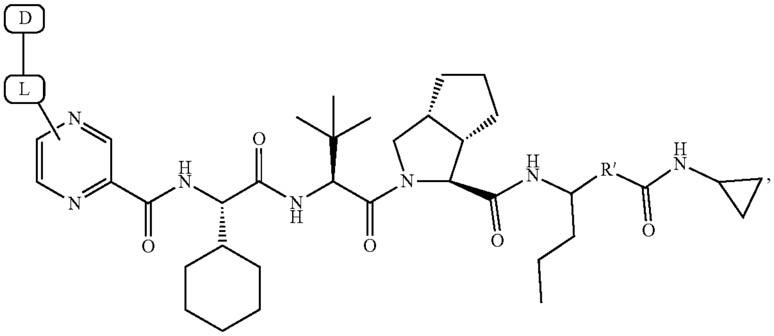

, wherein R' is CH—OH or C═O, or a pharmaceutically acceptable salt or stereoisomer thereof.

In some embodiments, the bifunctional compounds of the present invention are represented by any one of the following structures:

(dg1a)

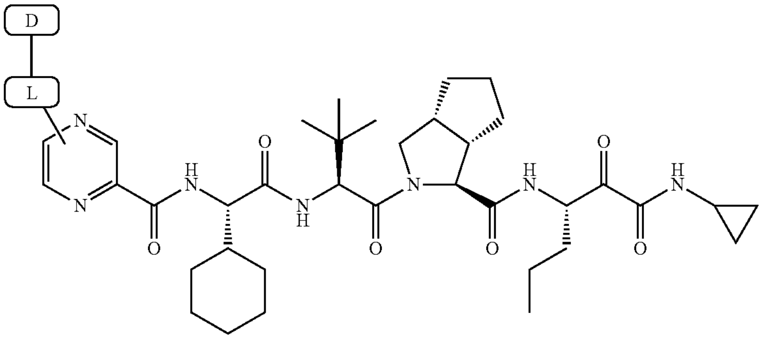

;

(dg1b)

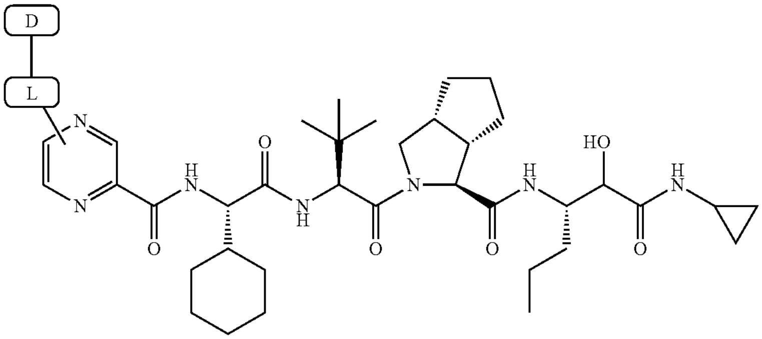

;

(dg1c)

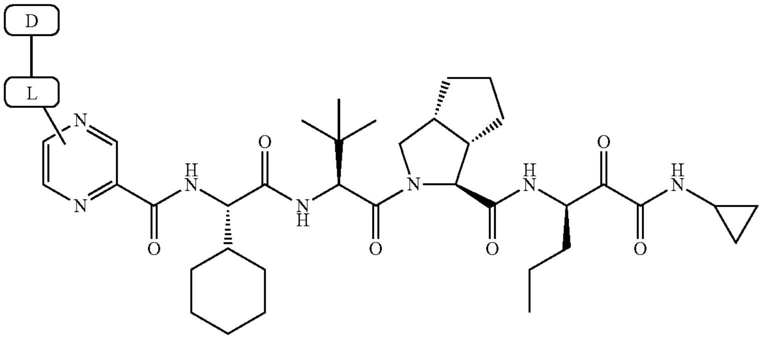

; and (dg1d)

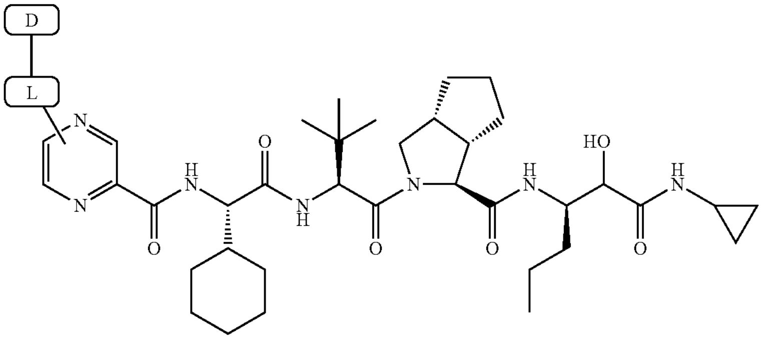

, or a pharmaceutically acceptable salt or stereoisomer thereof.

Linkers

The linker ("L") provides a covalent attachment of the NS3/4A targeting ligand to the degron. The structure of the linker may not be critical, provided it does not substantially interfere with the activity of the targeting ligand or the degron. In some embodiments, the linker is an alkylene chain (e.g., having 1-10 alkylene units). In other embodiments, the linker may be an alkylene chain or a bivalent alkylene chain, either of which may be interrupted by, and/or terminate (at either or both termini) at least one of —O—, —S—, —N(R")—, —C(O)—, —C(O)O—, —OC(O)—, —OC(O)O—, —C(NOR")—, —C(O)N(R")—, —C(O)N(R")C(O)—, —C(O)N(R")C(O)N(R")—, —N(R")C(O)—, —N(R")C(O)N(R")—, —N(R")C(O)O—, —OC(O)N(R")—, —C(NR")—, —N(R')C(NR")—, —C(NR")N(R")—, —N(R")C(NR")N(R")—, $—S(O)_2—$, —OS(O)—, —S(O)O—, —S(O)—, $—OS(O)_2—$, $—S(O)_2O—$, $—N(R")S(O)_2—$, $—S(O)_2N(R")—$, —N(R")S(O)—, —S(O)N (R")—, —N(R")S(O)$_2$N(R")—, —N(R')S(O)N(R')—, $C_{3-12}$ carbocyclene, 3- to 12-membered heterocyclene, 5- to 12-membered heteroarylene or any combination thereof, wherein R" is H or $C_1$-$C_6$ alkyl, wherein the one or both terminating groups may be the same or different.

In some embodiments the linker may be C1-C10 alkylene chain terminating in an NH-group wherein the nitrogen is also bound to the degron.

In certain embodiments, the linker is an alkylene chain having 1-10 alkylene units and interrupted by or terminating in

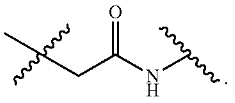 [SMILES: *CC(=O)N*]

In other embodiments, the linker is a polyethylene glycol chain having 2-8 PEG units and terminating in

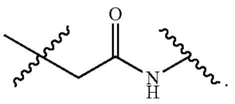 [SMILES: *CC(=O)N*]

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chains:

(L1)

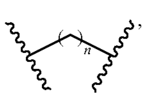

wherein n is an integer from 1-10 ("from" meaning inclusive), e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

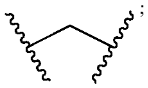

(L1-b)

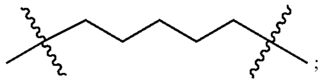

(L1-c)

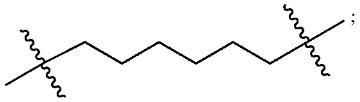

-continued (L1-d)

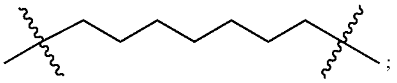

and (L1-e)

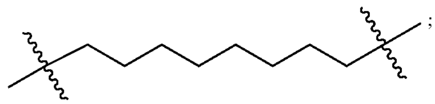

alkylene chains terminating in various functional groups (as described above), examples of which are as follows:

(L2-a)

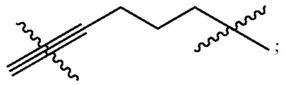

(L2-b)

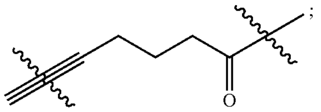

(L2-c)

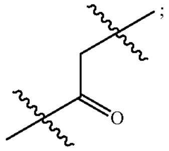

(L2-d)

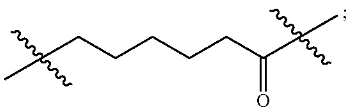

(L2-e)

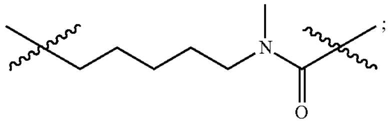

(L2-f)

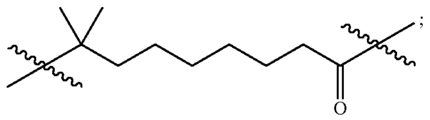

and (L2-g)

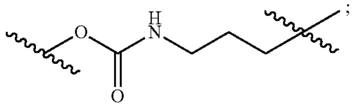

alkylene chains interrupted with various functional groups (as described above), examples of which are as follows:

(L3-a)

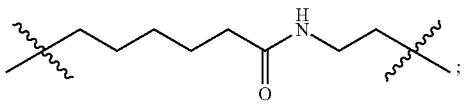

-continued (L3-b)

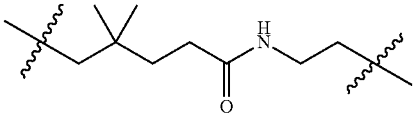

;

(L3-c)

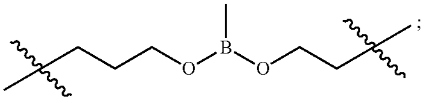

; and (L3-d)

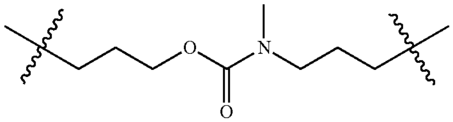

;

alkylene chains interrupted or terminating with heterocyclene groups, e.g.,

L4

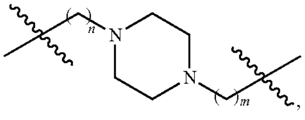

, wherein m and n are independently integers from 0-10, examples of which include:

(L4-a)

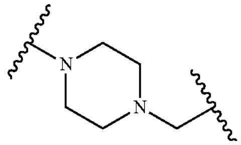

;

(L4-b)

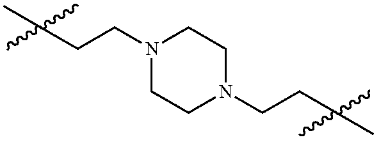

;

(L4-c)

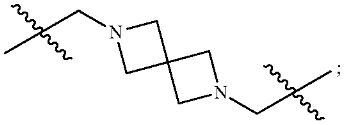

;

(L4-d)

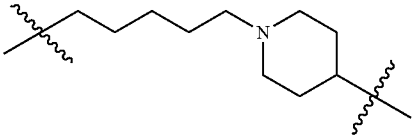

; and (L4-e)

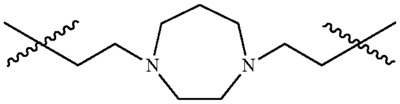

;

alkylene chains interrupted by amide, heterocyclene and/or aryl groups, examples of which include:

(L5-a)

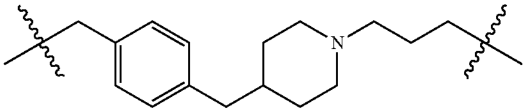

; and (L5-b)

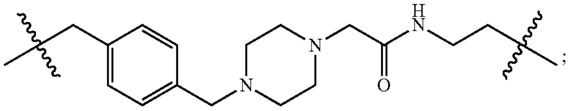

;

alkylene chains interrupted by heterocyclene and aryl groups, and a heteroatom, examples of which include:

(L6-a)

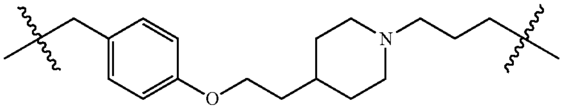

;

(L6-b)

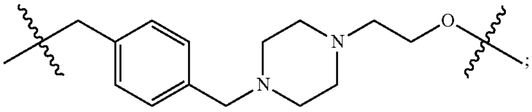

; and (L6-c)

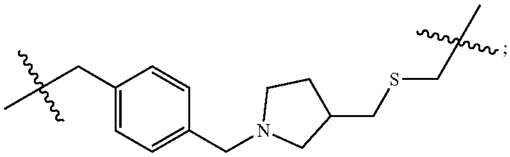

;

and alkylene chains interrupted by or terminating in a heteroatom such as N, O or B, e.g., (L7)

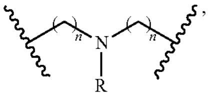

, wherein each n independently is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or C1 to C4 alkyl, an example of which is (L7-a)

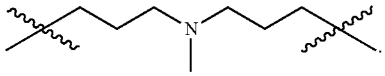

.

In some embodiments, the linker is a polyethylene glycol chain, examples of which include:

(L8)
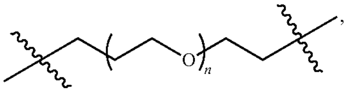
wherein n is an integer of 2-10, examples of which include:
(L8-a)
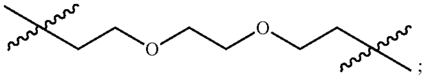
(L8-b)
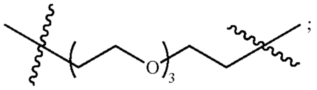
(L8-c)
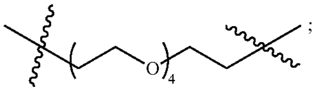
and
(L8-d)
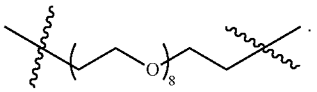
(L9-a)
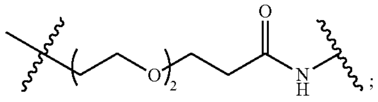
(L9-b)
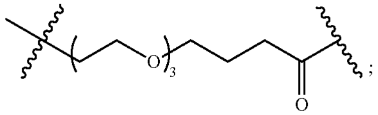
(L9-c)
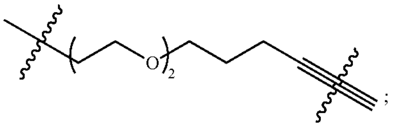
(L9-d)
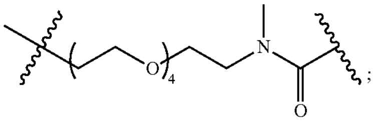
and
(L9-e)
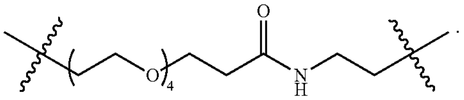
In some embodiments, the polyethylene glycol chain may terminate in a functional group, examples of which are as follows:
In some embodiments, the bifunctional compound of formula (I) includes a linker that is represented by any one of the following structures:
(L10)
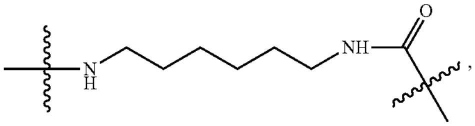
(L11)
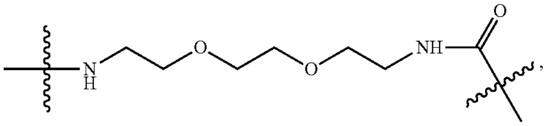
(L12)
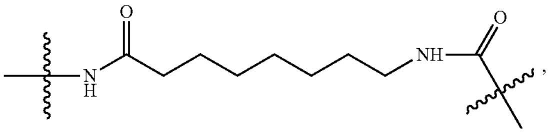
(L13)
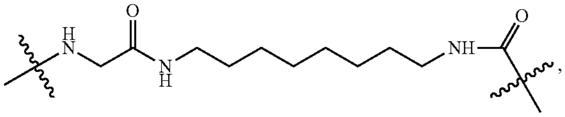
(L14)
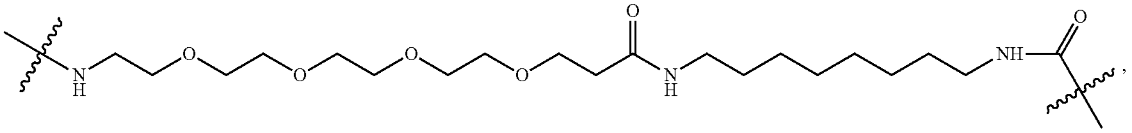
(L15)
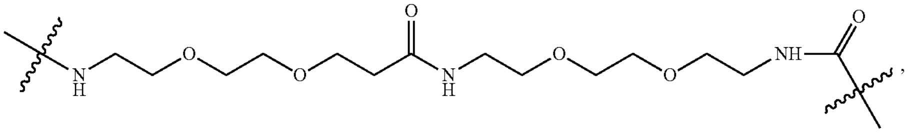
(L16)
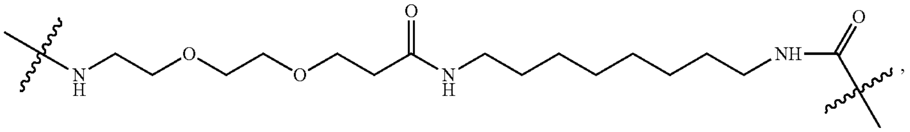

-continued
(L17)
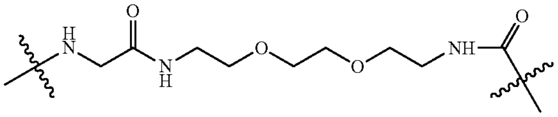,
(L18)
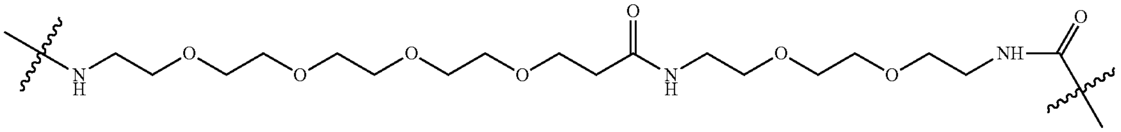,
(L19)
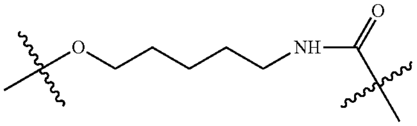,
(L20)
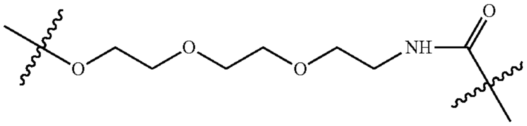,
(L21)
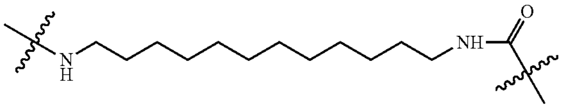,
(L22)
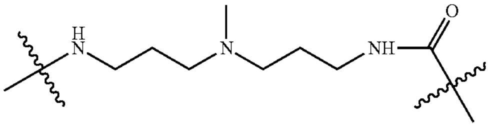,
(L23)
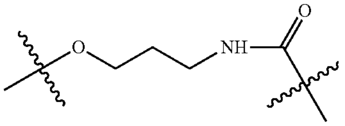, or
(L24)
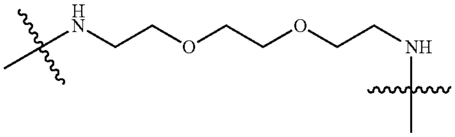.
Thus, in some embodiments, the bifunctional compounds of the present invention are represented by any one of the following structures:
(dg2)
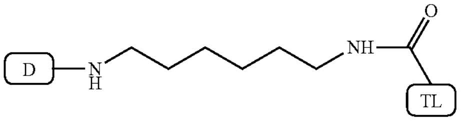,
(dg3)
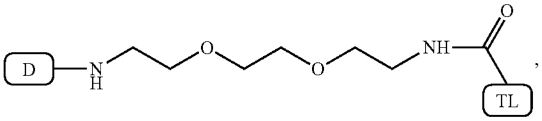,
(dg4)
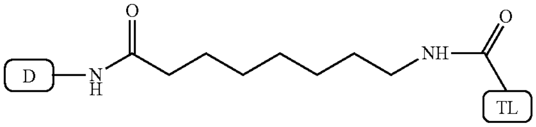,
(dg5)
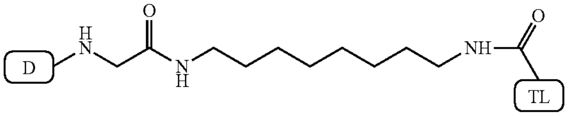,
(dg6)
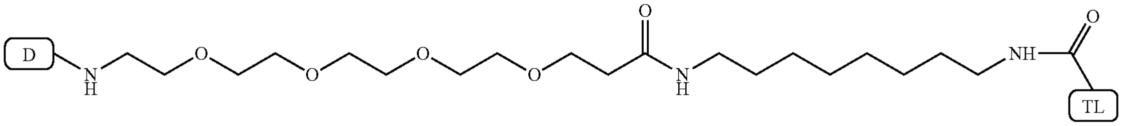,
(dg7)
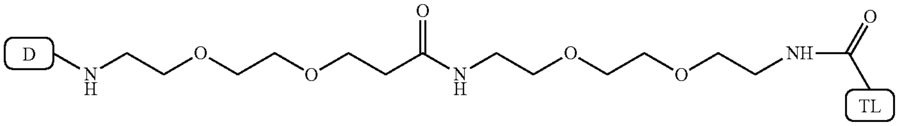,
(dg8)
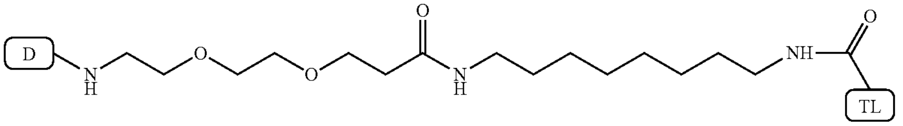, -continued (dg9)

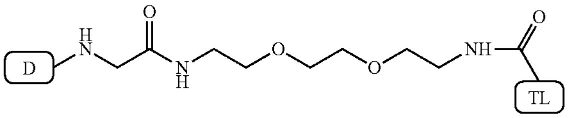

, (dg10)

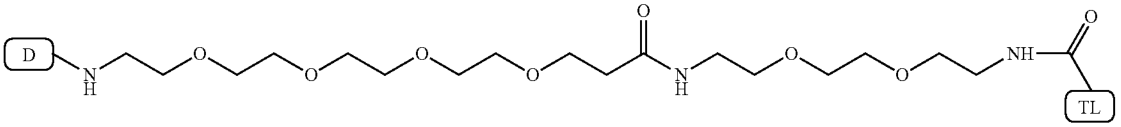

, (dg11)

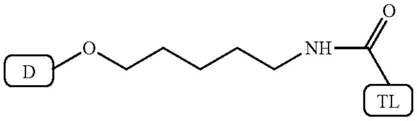

, (dg12)

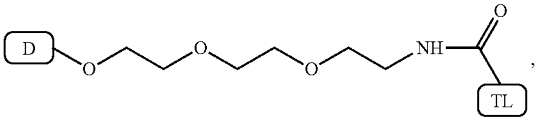

, (dg13)

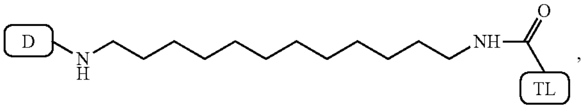

, (dg14)

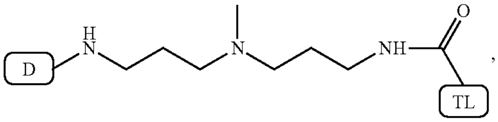

, (dg15)

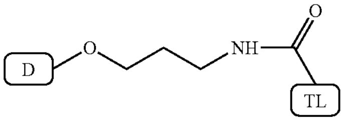

, and (dg16)

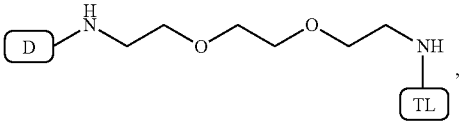

, wherein TL is a NS3/4A targeting ligand as defined herein and D is a degron as defined herein; or a pharmaceutically acceptable salt or stereoisomer thereof.

Degrons

The degron ("D") is a functional moiety that binds an E3 Ubiquitin Ligase.

In some embodiments, the degron binds Von Hippel Landau tumor suppressor (VHL). Representative examples of degrons that bind VHL are as follows:

(D1-a))

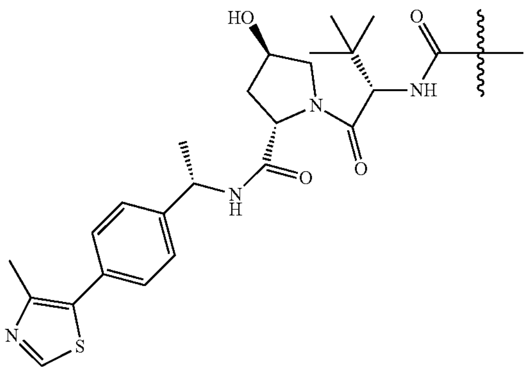

;

-continued (D1-b)

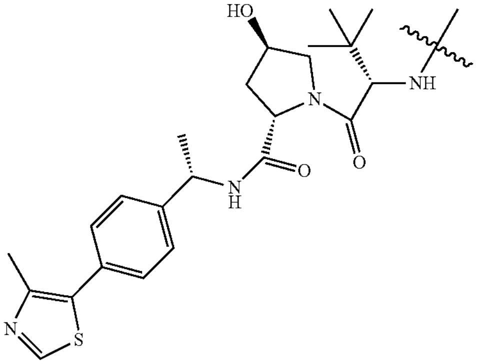

;

(D1-c)

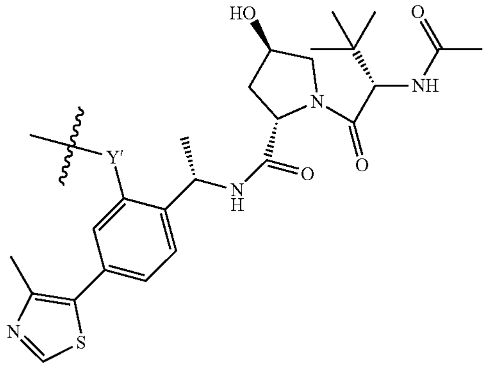

, wherein Y' is a bond, N, O or C; and (D1-d)

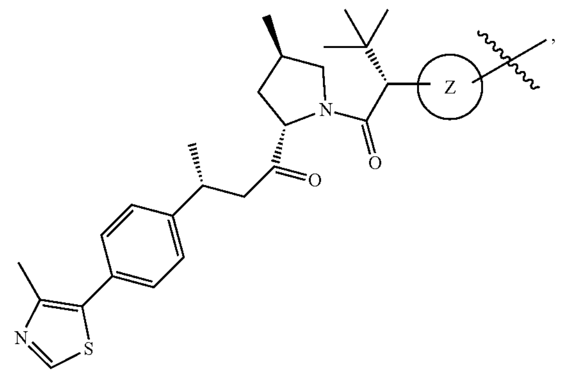

wherein Z is a $C_5$-$C_6$ carbocyclic or heterocyclic group; and (D1-e)

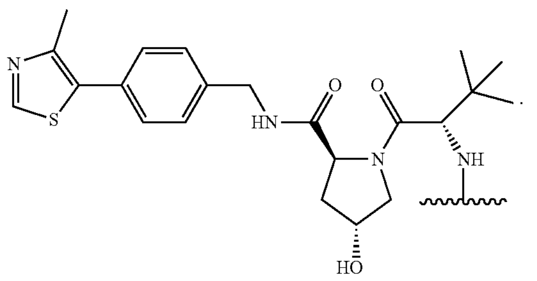

Yet other degrons that bind VHL and which may be suitable for use in the present invention are disclosed in U.S. Patent Application Publication 2017/0121321 A1.

In some embodiments, the compound of formula (I) includes a degron that binds cereblon (CRBN).

Representative examples of degrons that bind cereblon and which may be suitable for use in the present invention are described in U.S. Patent Application Publication 2018/0015085 A1 (e.g., the indolinones such as isoindolinones and isoindoline-1,3-diones embraced by formulae IA ad IA' therein, and the bridged cycloalkyl compounds embraced by formulae IB and IB' therein).

In some embodiments, the compounds of formula (I) include a degron that binds cereblon, and is represented by any one of structures D2-a to D2-q:

(D2-a)

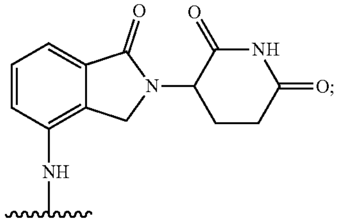

-continued (D2-b)

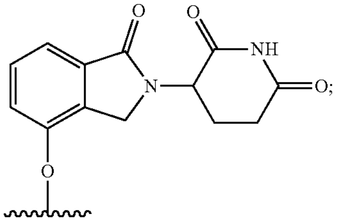

(D2-c)

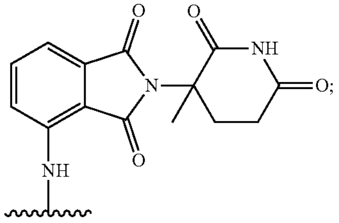

(D2-d)

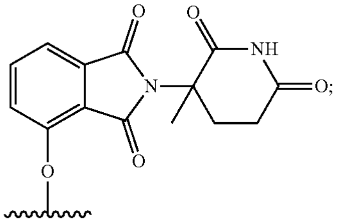

(D2-e)

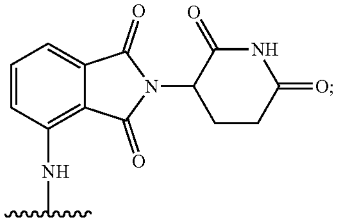

(D2-f)

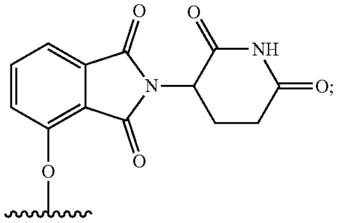

(D2-g)

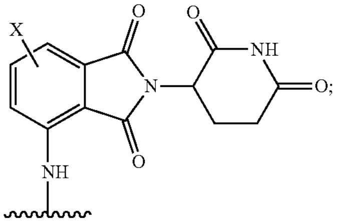

(D2-h)

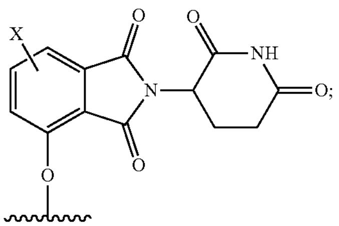

-continued
(D2-i)
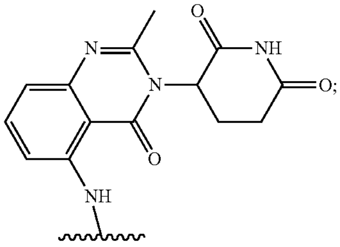
(D2-j)
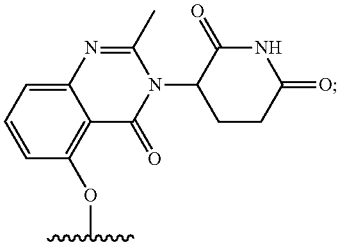
(D2-k)
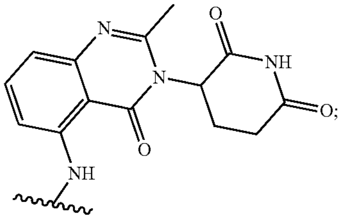
(D2-l)
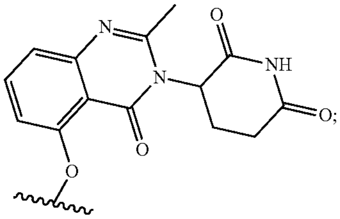
(D2-m)
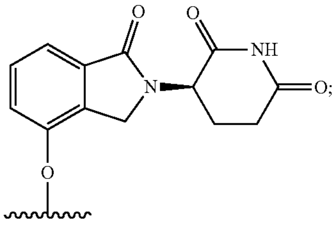
(D2-n)
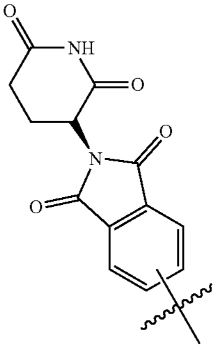
;
-continued
(D2-o)
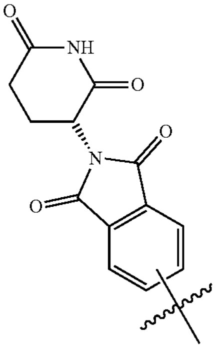
;
(D2-p)
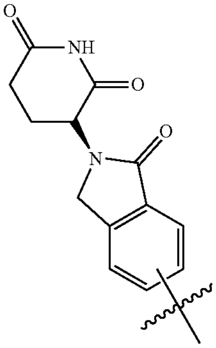
; and
(D2-q)
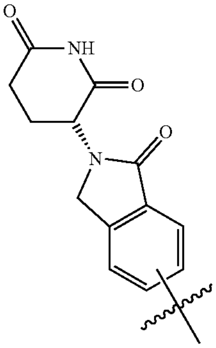
,
wherein X is halo, methyl, methoxy, CN, $CF_3$ or $OCF_3$.
In some embodiments, the degron that binds cereblon is represented by the following structure:
(D3)
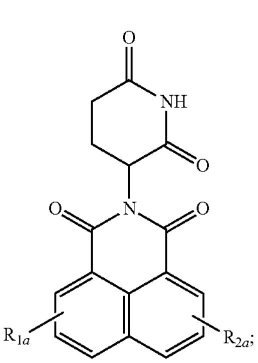
wherein $R_{1a}$ and $R_{2a}$ independently represent H, hydroxyl, optionally substituted alkoxy, optionally substituted amine, or

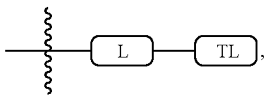

provided that one of $R_{1a}$ and $R_{2a}$ represents

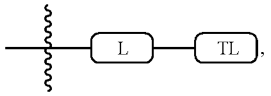

or a pharmaceutically acceptable salt or stereoisomer thereof. In some embodiments, $R_{1a}$ represents

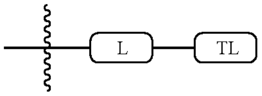

and $R_{2a}$ represents H, hydroxyl, optionally substituted alkoxy or optionally substituted amine. In some embodiments, $R_{2a}$ represents

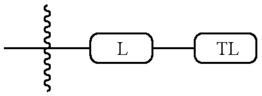

and $R_{1a}$ represents H, hydroxyl, optionally substituted alkoxy or optionally substituted amine.

In some embodiments, $R_{1a}$ and $R_{2a}$ independently represent C1-C3 or C1-C5 alkoxy, provided that one of $R_{1a}$ and $R_{2a}$ represents

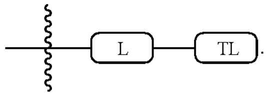

In some embodiments, the compound of formula (I) includes a degron that is represented by the following structure:

(D3-a)

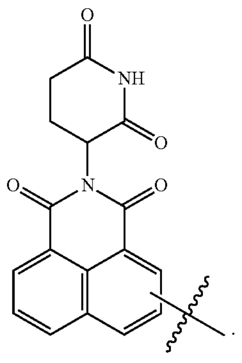

In some embodiments, the degron that binds cereblon is represented by the following structure:

(D4)

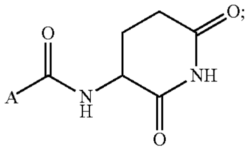

wherein A represents $A_1$, $A_2$, or $A_3$:

$(A_1)$

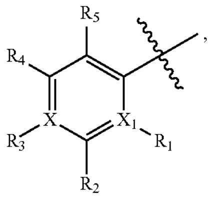

wherein X and $X_1$ independently represent C or N, provided that one of X and $X_1$ represents N; wherein $R_1$ is absent if $X_1$ represents N, and if $X_1$ represents C, $R_1$ represents H, or together with $R_2$ and the other atoms to which they are bound form an optionally substituted 5- or 6-membered carbocyclic group (e.g., an optionally substituted aryl group) or an optionally substituted 5- or 6-membered heterocyclic group (e.g., an optionally substituted 5- or 6-membered heteroaryl group); $R_2$ represents H, halo, optionally substituted C1-C4 alkoxy, optionally substituted aryl (which as defined herein embraces aralkyl and aralkoxy), optionally substituted heteroaryl (which as defined herein embraces heteroaralkyl and heteroaralkoxy), or $NR_6R_7$, wherein each of $R_6$ and $R_7$ independently represents H or a substituent (e.g., optionally substituted aryl), or $R_2$ together with $R_1$ and the other atoms to which they are bound form an optionally substituted 5- or 6-membered carbocyclic group (e.g., an optionally substituted aryl group) or an optionally substituted 5- or 6-membered heterocyclic group (e.g., an optionally substituted 5- or 6-membered heteroaryl group); if X represents N, $R_3$ is absent, and if X represents C, $R_3$ independently represents H, halo, amine, optionally substituted amine, optionally substituted C1-C4 alkoxy,

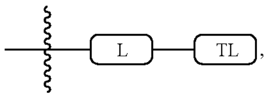

wherein L represents a linker, and TL represents a ligand that binds a protein target, or $NR_6R_7$, or wherein $R_2$ and $R_3$, or $R_3$ and $R_4$, together with the atoms to which they are bound form an optionally substituted 5- or 6-membered carbocyclic group (e.g., an optionally substituted aryl group) or an optionally substituted 5- or 6-membered heterocyclic group (e.g., an optionally substituted 5- or 6-membered heteroaryl group);

$R_4$, and $R_5$ each independently represents H, halo, optionally substituted amine, optionally substituted C1-C4 alkoxy, optionally substituted aryl, optionally substituted heteroaryl,

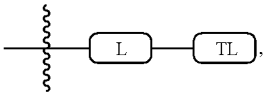, or $NR_6R_7$, or wherein $R_3$ and $R_4$, or $R_4$ and $R_5$, together with the atoms to which they are bound form an optionally substituted 5- or 6-membered carbocyclic group (e.g., an optionally substituted aryl group) or an optionally substituted 5- or 6-membered heterocyclic group (e.g., an optionally substituted 5- or 6-membered heteroaryl group), provided that one of $R_3$, $R_4$ and $R_5$ represents

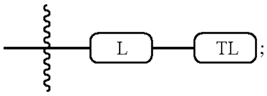;

or wherein A represents $A_2$:

($A_2$)

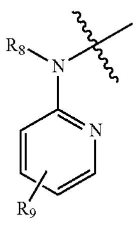, wherein $R_8$ represents H, optionally substituted alkyl, optionally substituted amine, optionally substituted alkoxy, optionally substituted 5- or 6-membered carbocyclic group (e.g., an optionally substituted aryl group), optionally substituted 5- or 6-membered heterocyclic group (e.g., an optionally substituted 5- or 6-membered heteroaryl group), and $R_9$ is

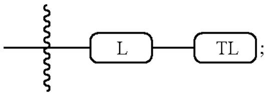;

or wherein A represents $A_3$:

($A_3$)

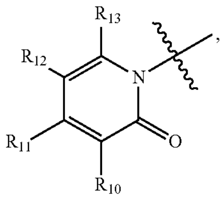, wherein $R_{10}$, $R_{11}$, $R_{12}$ and $R_{13}$ independently represent H,

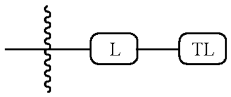, or a substituent, or wherein $R_{10}$ and $R_{11}$ together with the atoms to which they are bound form an optionally substituted 5- or 6-membered carbocyclic group (e.g., optionally substituted aryl group), an optionally substituted 5- or 6-membered heterocyclic group (e.g., an optionally substituted 5- or 6-membered heteroaryl group), or wherein $R_{11}$ and $R_{12}$ together with the atoms to which they are bound form an optionally substituted 5- or 6-membered carbocyclic group (e.g., an aryl group), an optionally substituted 5- or 6-membered heterocyclic group (e.g., a 5- or 6-membered heteroaryl group), or wherein $R_{12}$ and $R_{13}$ together with the atoms to which they are bound form an optionally substituted 5- or 6-membered carbocyclic group (e.g., an aryl group), or an optionally substituted 5- or 6-membered heterocyclic group (e.g., a 5- or 6-membered heteroaryl group), provided that one of $R_{10}$, $R_{11}$, $R_{12}$ and $R_{13}$ represents

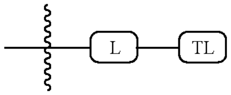;

or a pharmaceutically acceptable salt or stereoisomer thereof.

In some embodiments wherein A is $A_1$ and X and $X_1$ both represent C, one of $R_3$, $R_4$ and $R_5$ represents

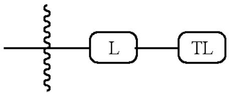

and all but one of $R_1$, $R_2$, $R_3$, $R_4$, and $R_5$ represents H. In some embodiments, such as when X represents N (requiring $R_3$ to be absent), one of $R_4$ and $R_5$ represents

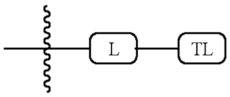

and all but one of $R_1$, $R_2$, and one of $R_4$ and $R_5$ represents H. In some embodiments, such as when $X_1$ represents N, one of $R_3$, $R_4$ and $R_5$ represents

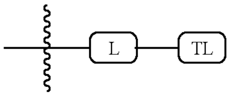

and all but one of $R_2$, $R_3$, and one of $R_4$ and $R_5$ represents H. In some embodiments, one of $R_1$, $R_2$, $R_3$, $R_4$, and $R_5$ represents a substituted benzyloxy group (e.g., 4-[[4(oxymethyl)phenyl]methyl]morpholine), or halo (e.g., C1). In some embodiments, $R_1$ and $R_2$ together with the atoms to which they are bound form an optionally substituted 6-membered heteroaryl group such as a pyridyl group.

In some embodiments wherein A is $A_2$, $R_8$ is H or methyl, and $R_9$ is

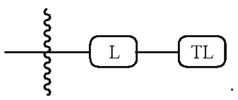

.

In some embodiments wherein A is $A_3$, $R_{10}$ and $R_{11}$ together with the atoms to which they are bound form an optionally substituted 6-membered aryl group. In some embodiments, $R_{11}$ and $R_{12}$ together with the atoms to which they are bound form an optionally substituted 6-membered aryl group. In some embodiments, $R_{12}$ and $R_{13}$ together with the atoms to which they are bound form an optionally substituted 6-membered aryl group. In some embodiments, the aryl group formed by $R_{10}$ and $R_{11}$, or by $R_{11}$ and $R_{12}$, or by $R_{12}$ and $R_{13}$ is a phenyl group. In some embodiments, the 6-membered aryl group is unsubstituted.

In some embodiments wherein $R_2$ and $R_3$, or $R_3$ and $R_4$, or $R_4$ and $R_5$, or $R_9$ and $R_{10}$, or $R_{10}$ and $R_{11}$, or $R_{11}$ and $R_{12}$, or $R_{12}$ and $R_{13}$, together with the atoms to which they are bound form an optionally substituted 5- or 6-membered carbocyclic group (e.g., an optionally substituted group aryl) or optionally substituted 5- or 6-membered heterocyclic group (e.g., an optionally substituted 5- or 6-membered heteroaryl group) an optional substituent is

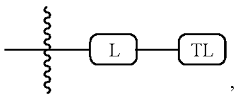

, provided that the bifunctional compound has a single

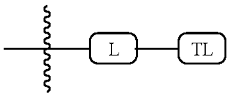

group.

In some embodiments, the degron that binds cereblon is represented by the following structure:

(D4-a)

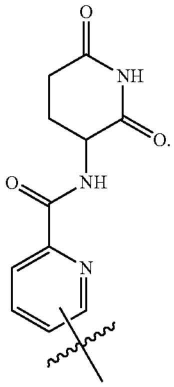

Thus, in some embodiments, the bifunctional compounds of the present invention are represented by any one of the following structures (with the linker shown generically):

(dg17)

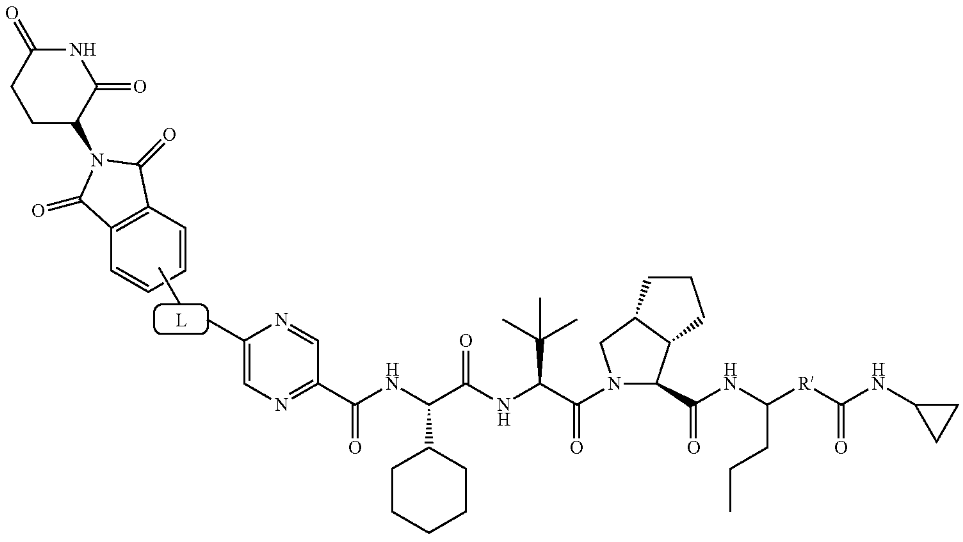

;

-continued
(dg18)
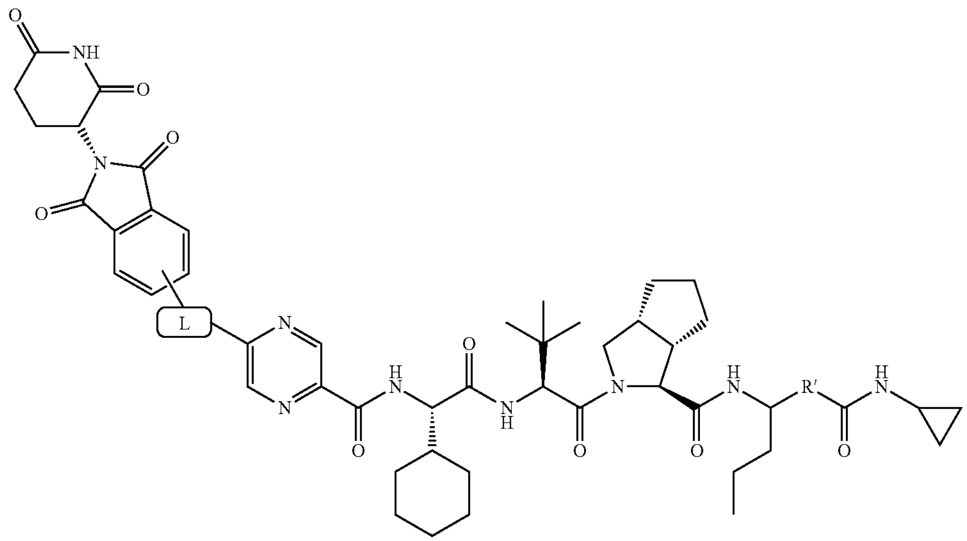
;
(dg19)
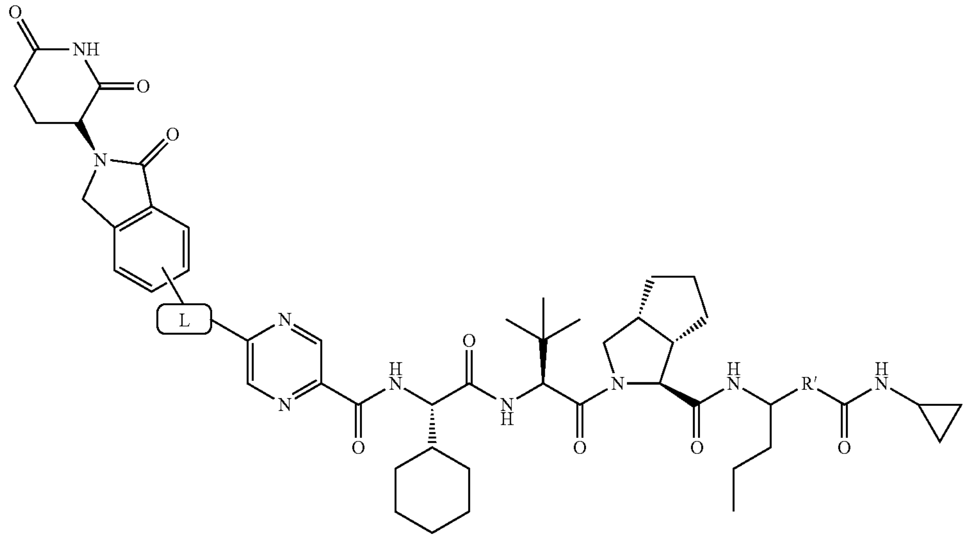
;
(dg25)
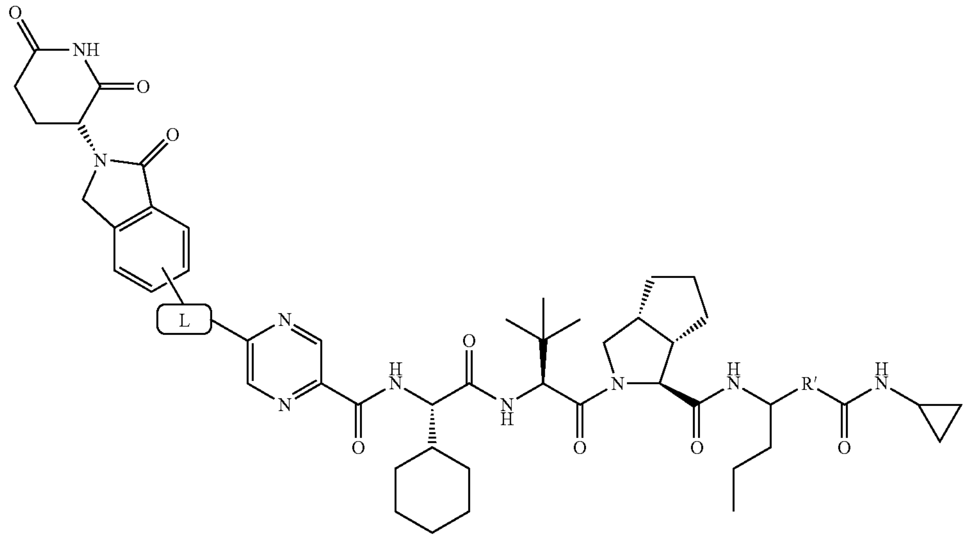
;

-continued
(dg20)
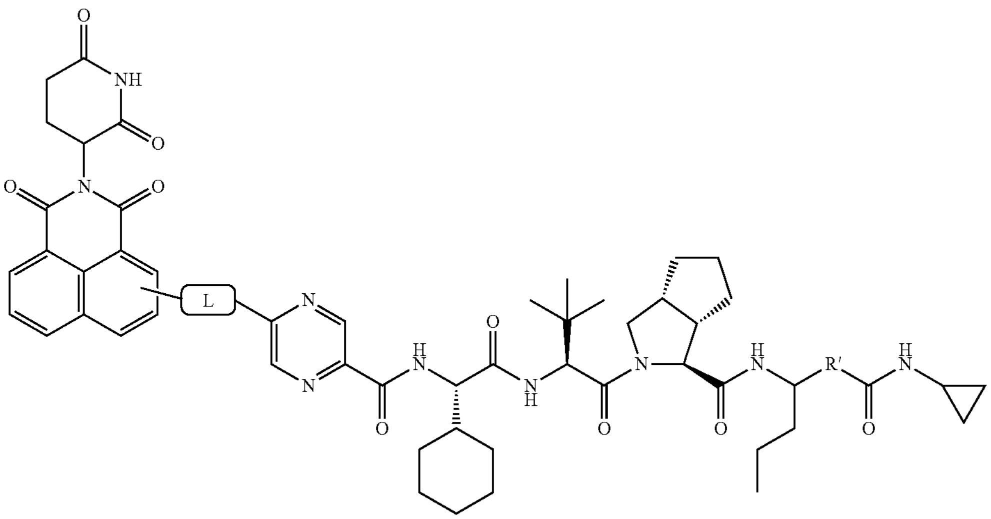
;
(dg21)
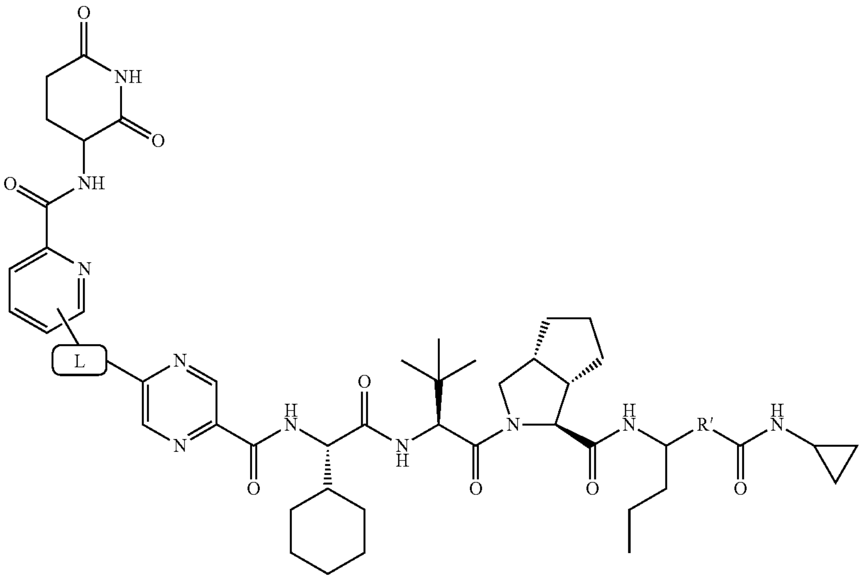
;
(dg17a)
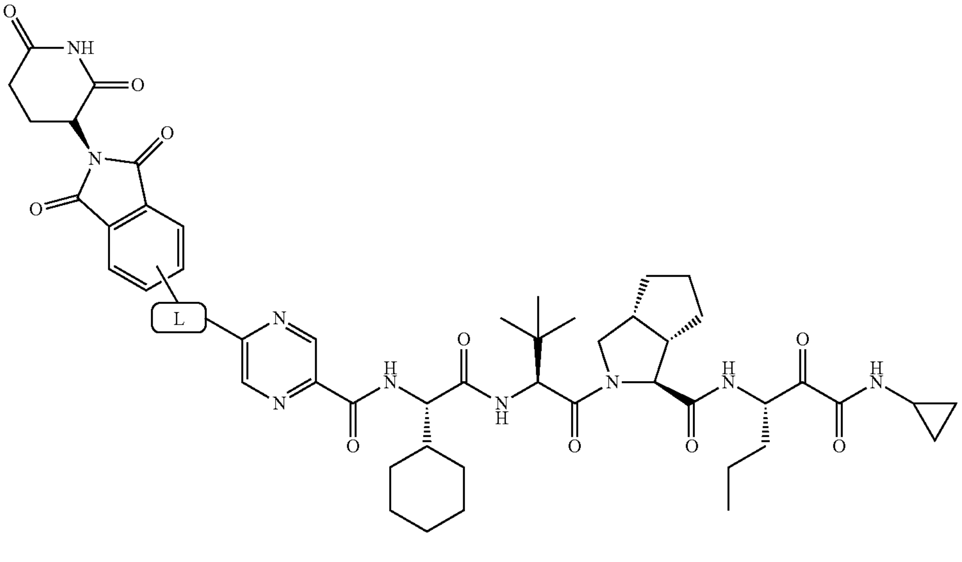
;

-continued
(dg18a)
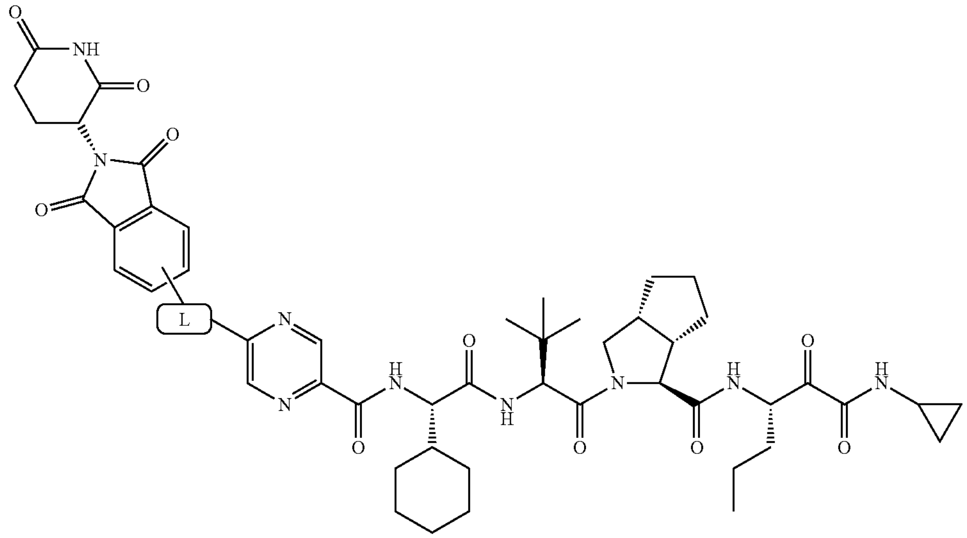
;
(dg19a)
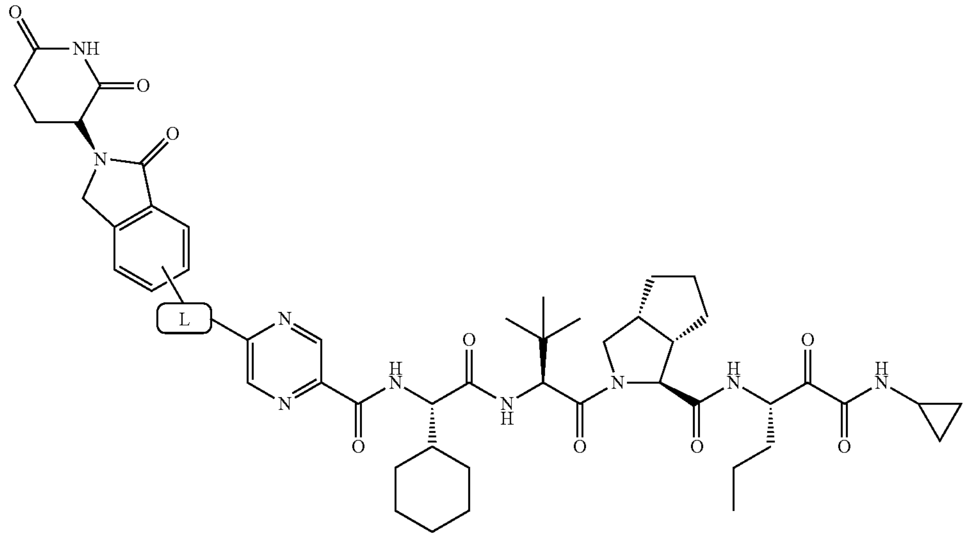
;
(dg20a)
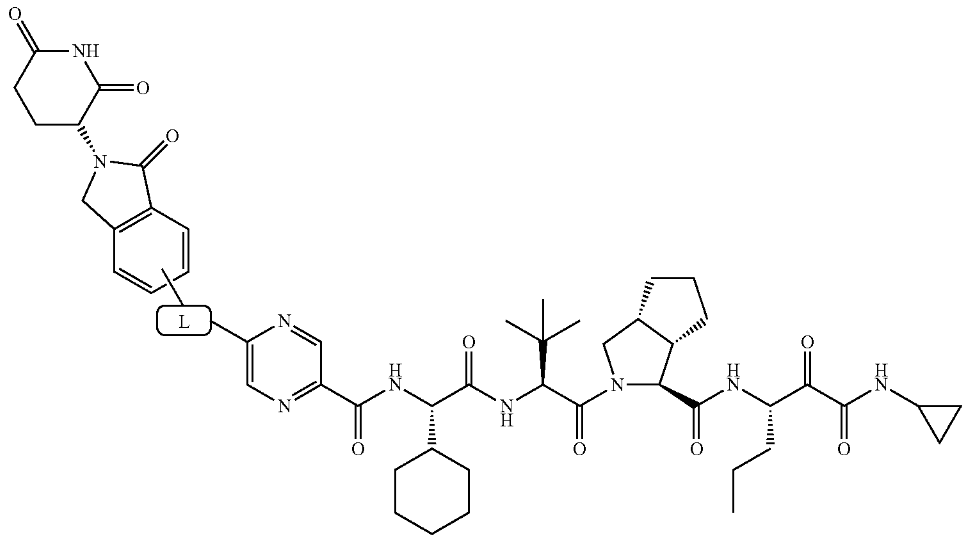
;

-continued
(dg21a)
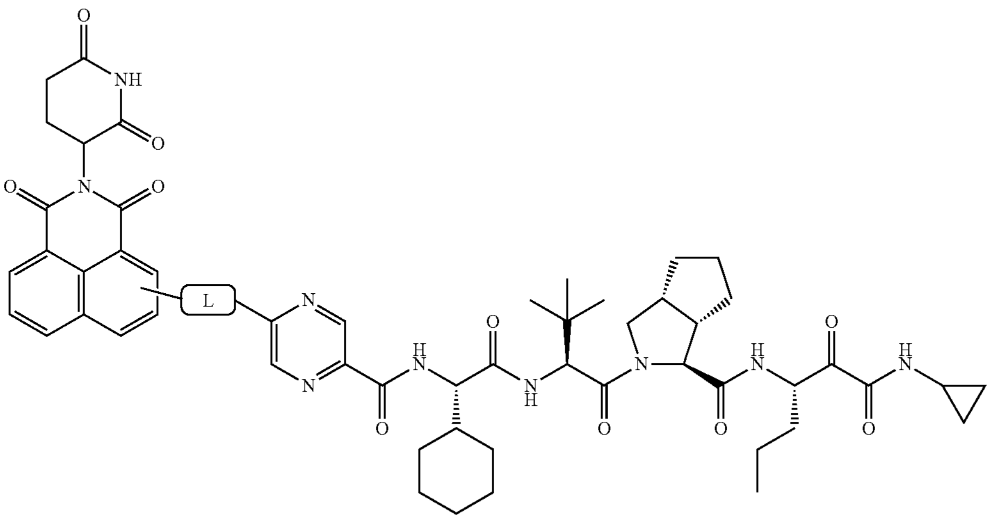
;
(dg22a)
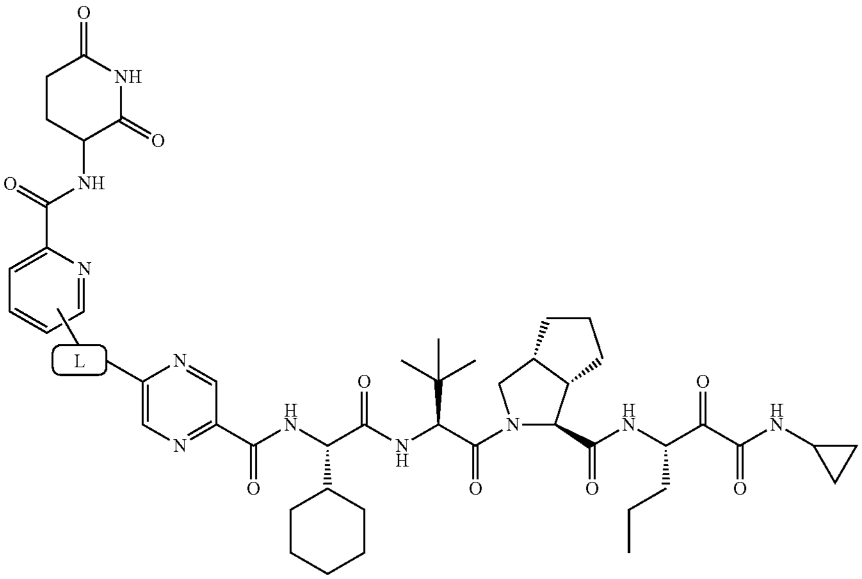
;
(dg17b)
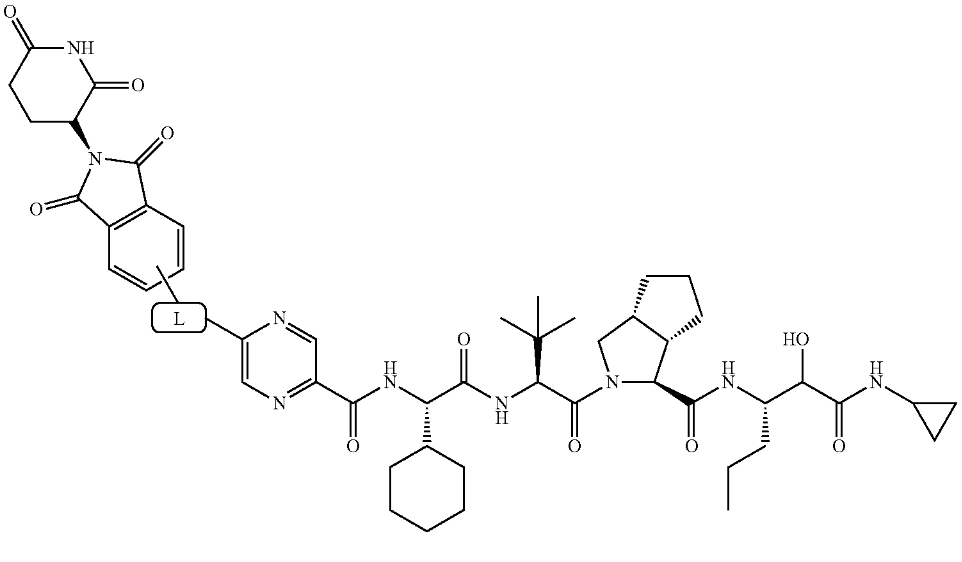
;

-continued
(dg18b)
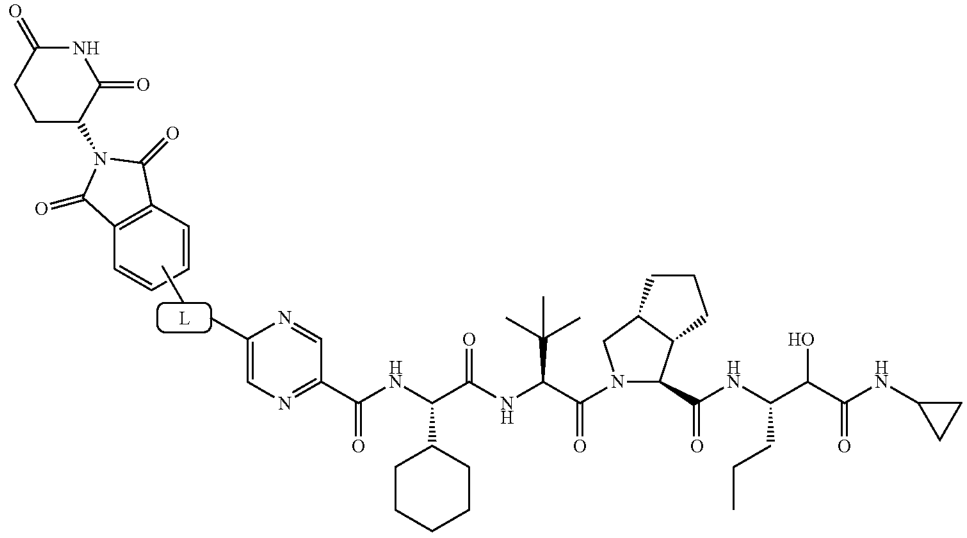
;
(dg19b)
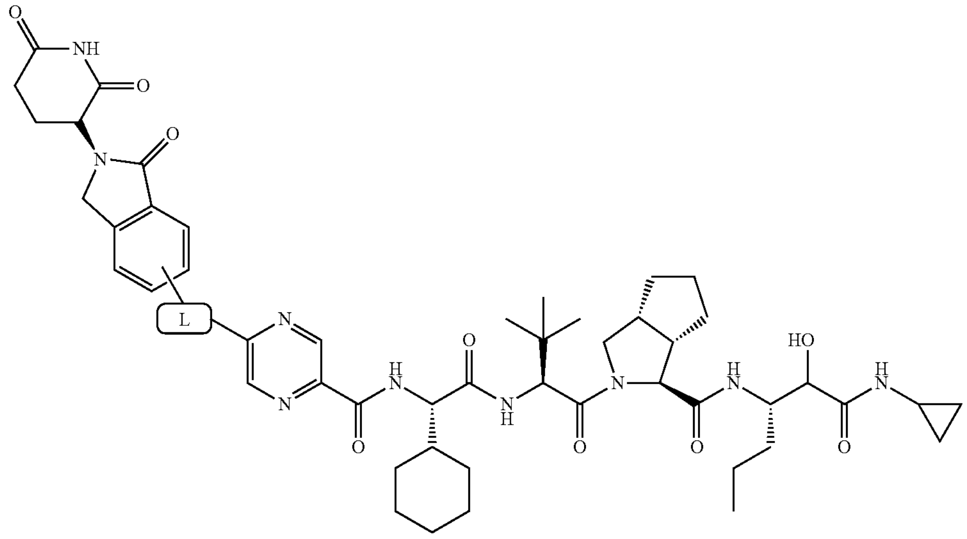
;
(dg20b)
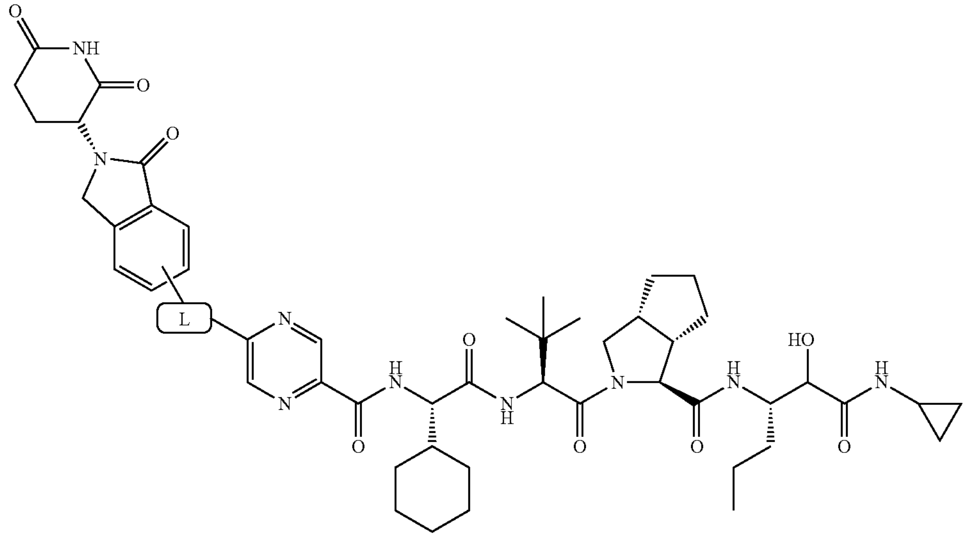
;

-continued
(dg21b)
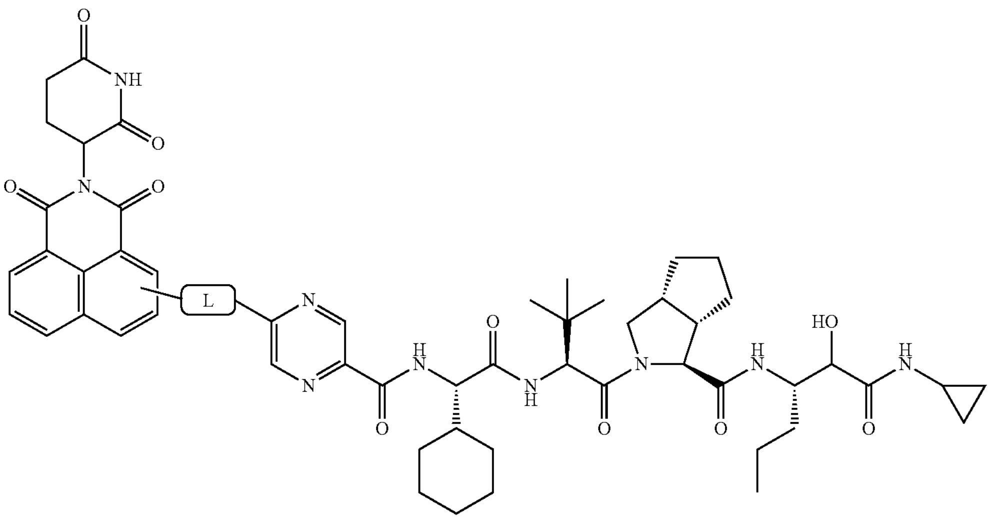
;
(dg22b)
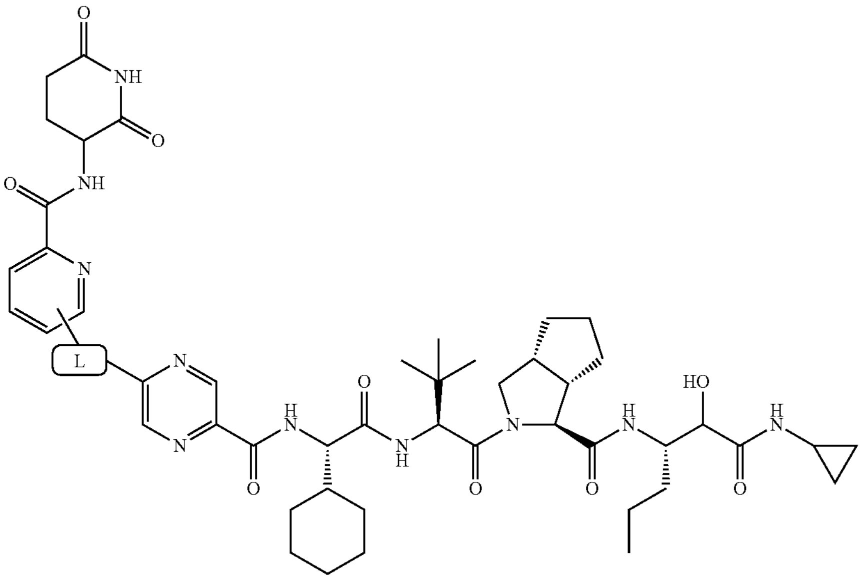
;
(dg17c)
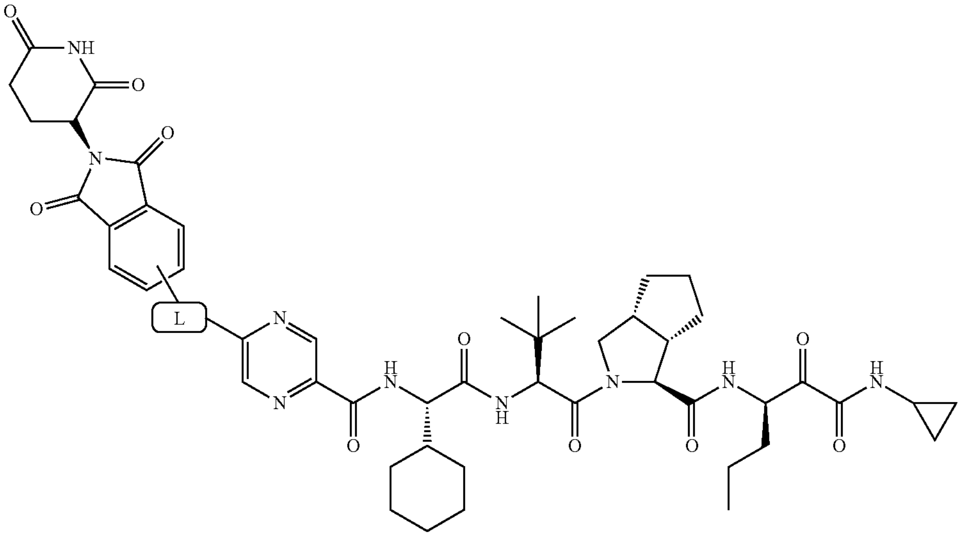
;

-continued
(dg18c)
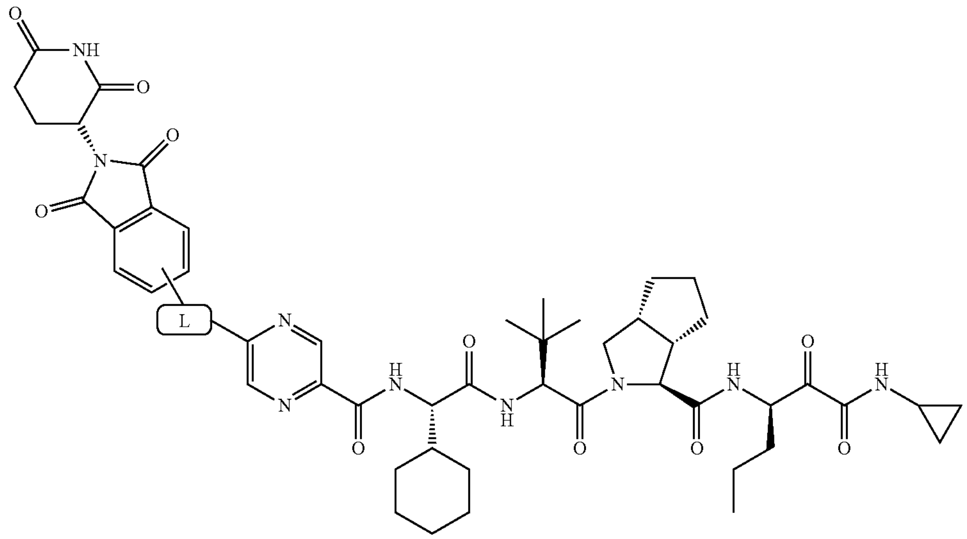
;
(dg19c)
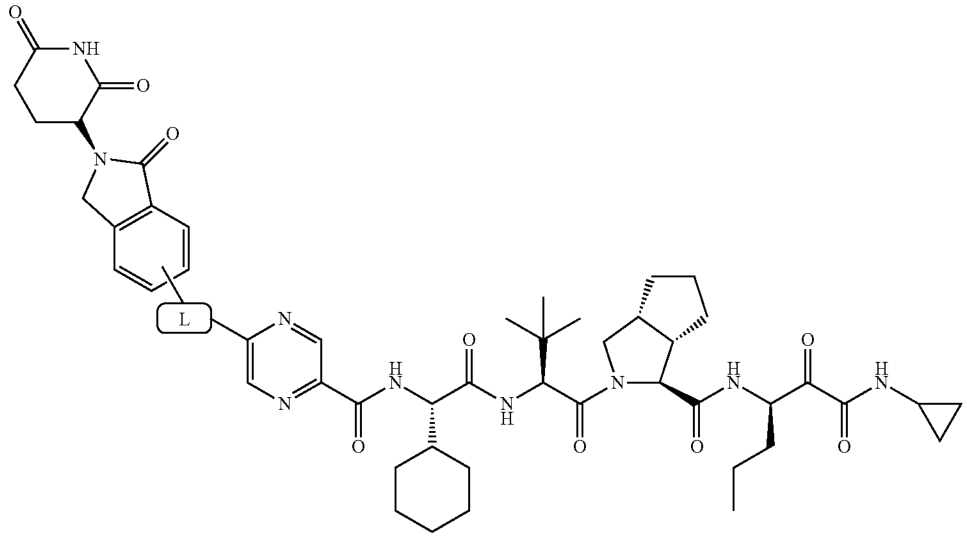
;
(dg20c)
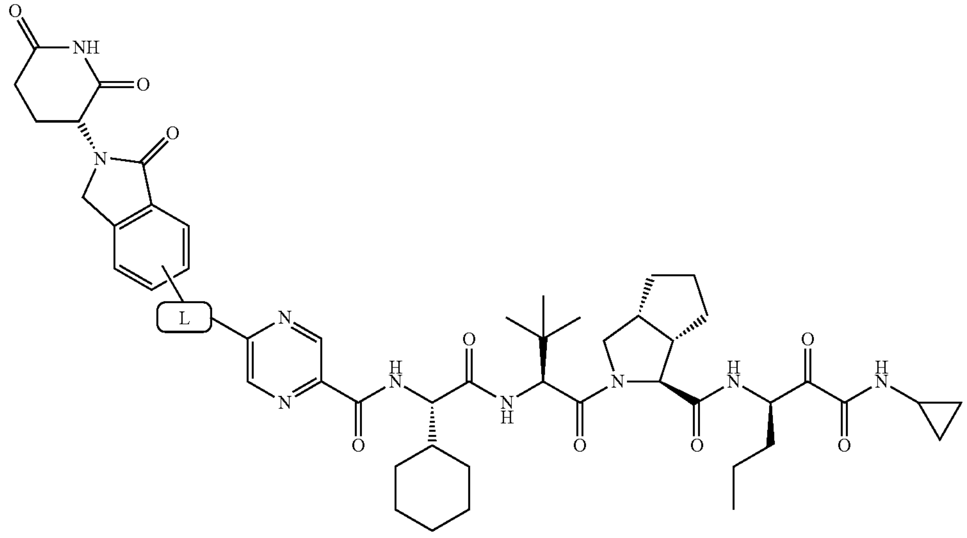
;

-continued
(dg21c)
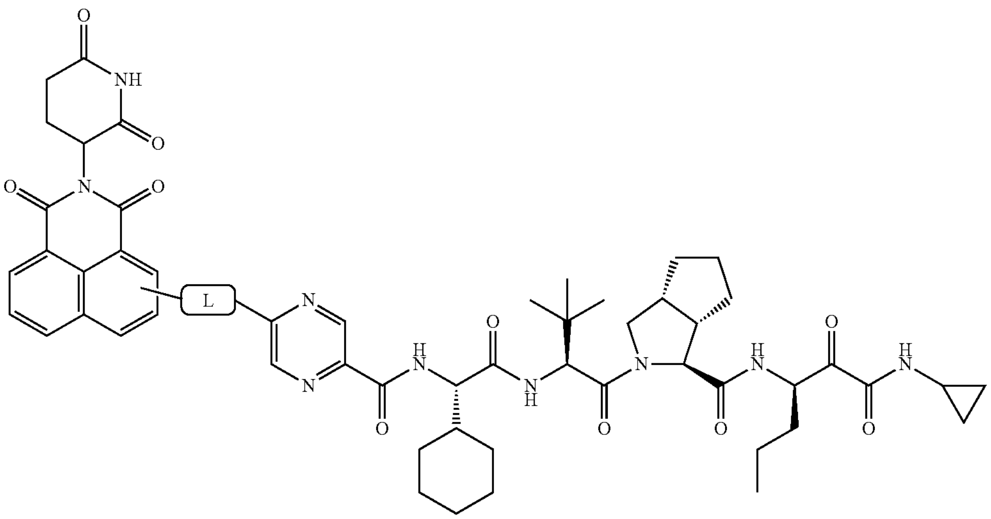
;
(dg22c)
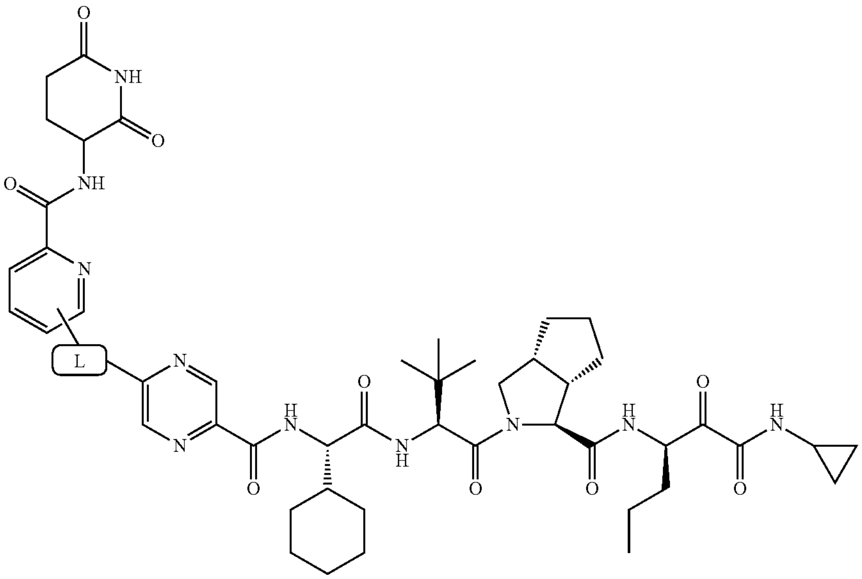
;
(dg17d)
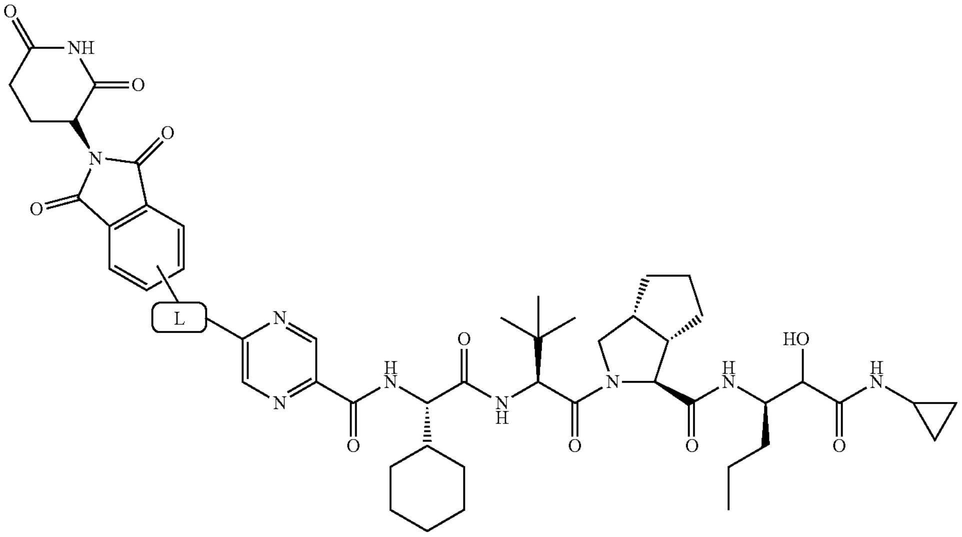
;

-continued
(dg18d)
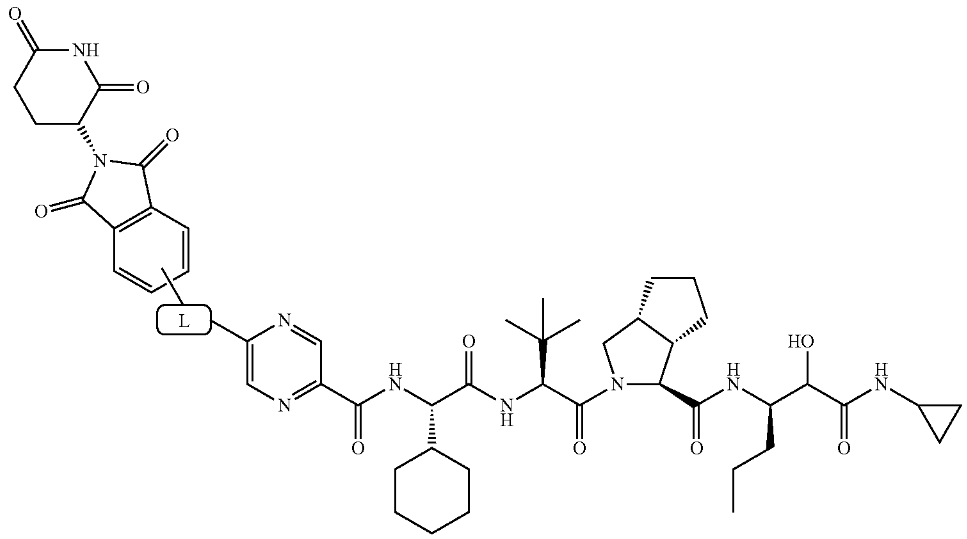
;
(dg19d)
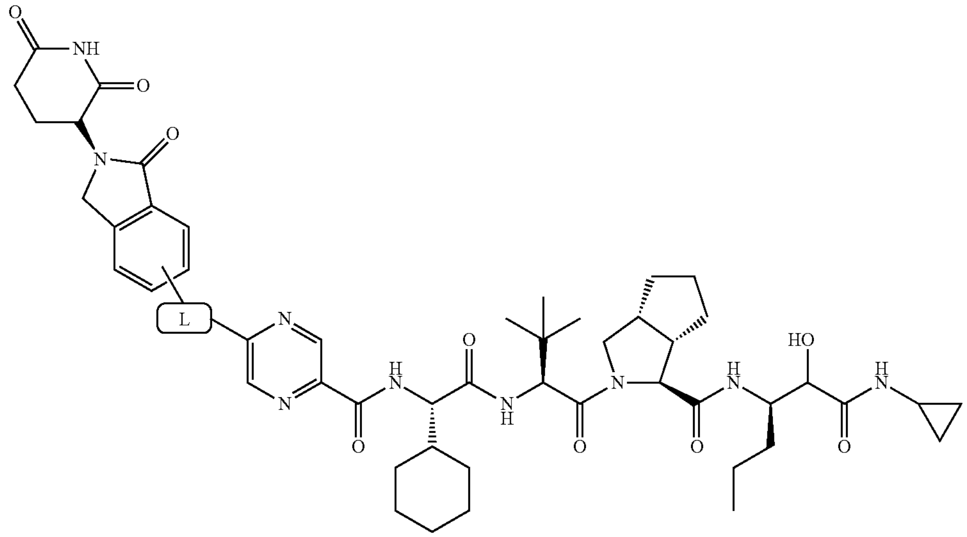
;
(dg20d)
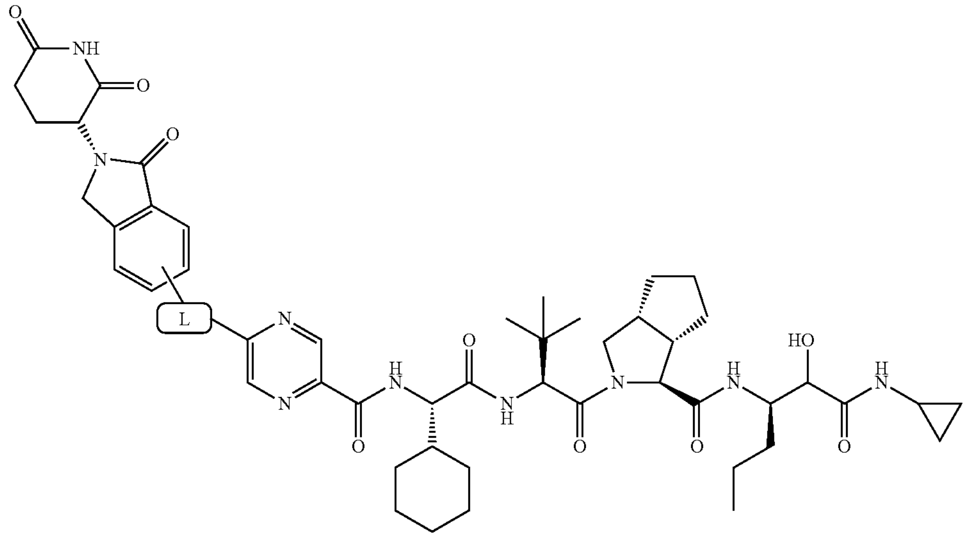
;

-continued
(dg21d)
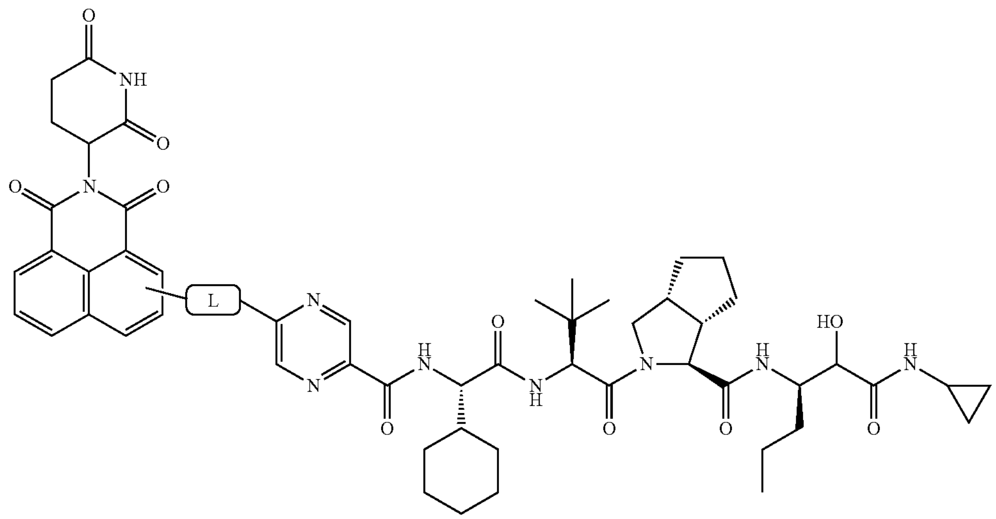
; and
(dg22d)
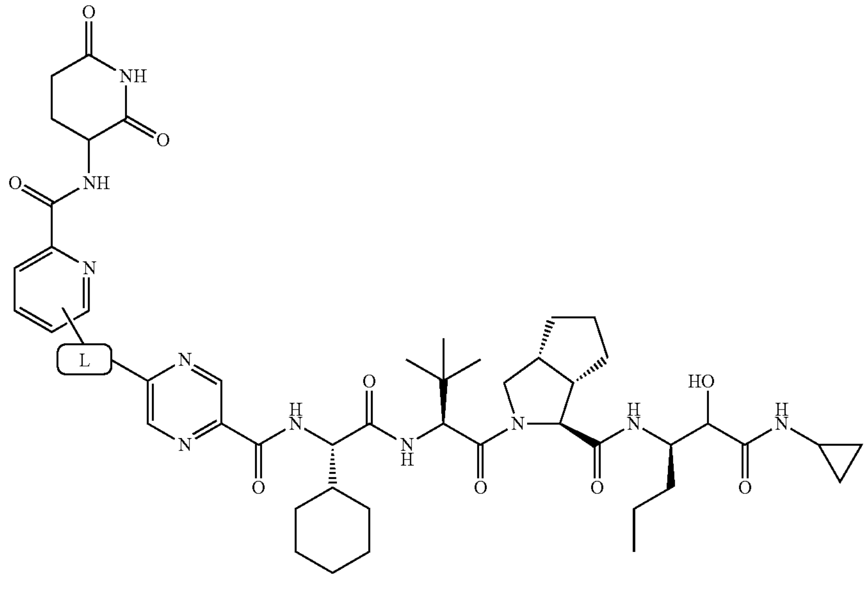
;
wherein R' is C—OH or C═O and L is a linker as described herein; or a pharmaceutically acceptable salt or stereoisomer thereof.

In some embodiments, the bifunctional compounds of the present invention are represented by any one of the following structures:
(1)
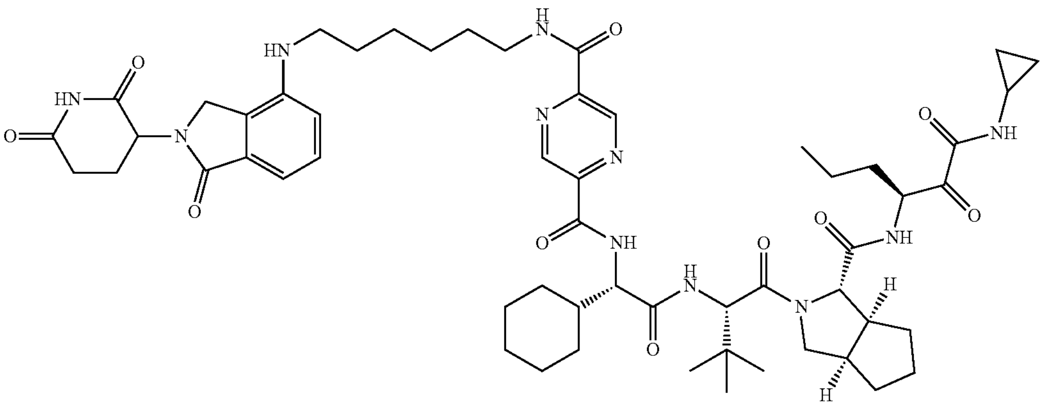
;
(2)
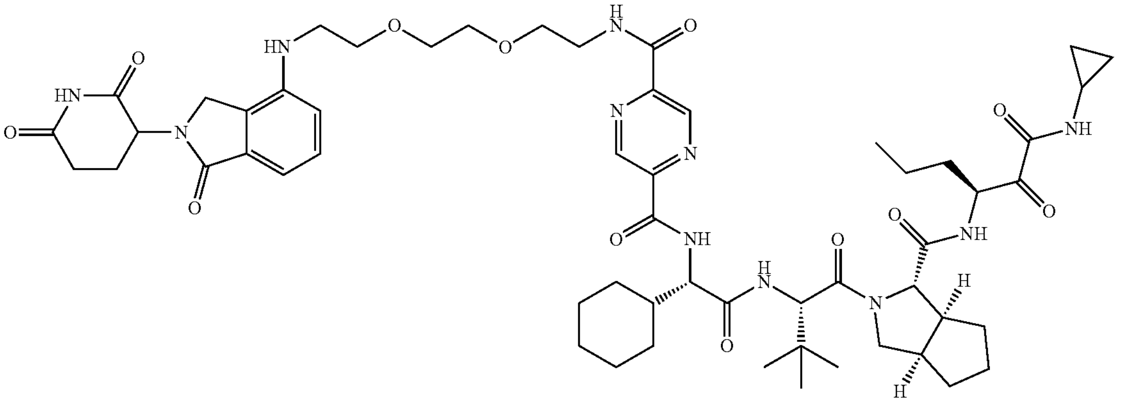
;
(3)
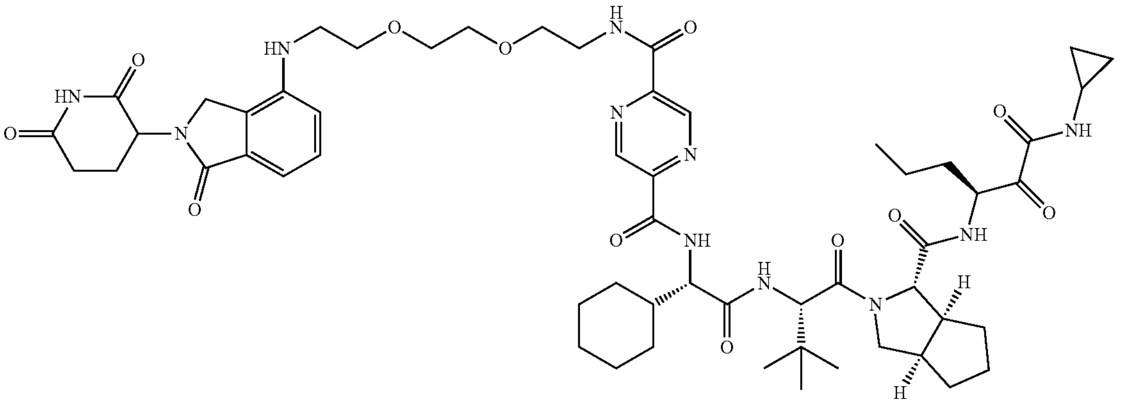
;

-continued
(4)
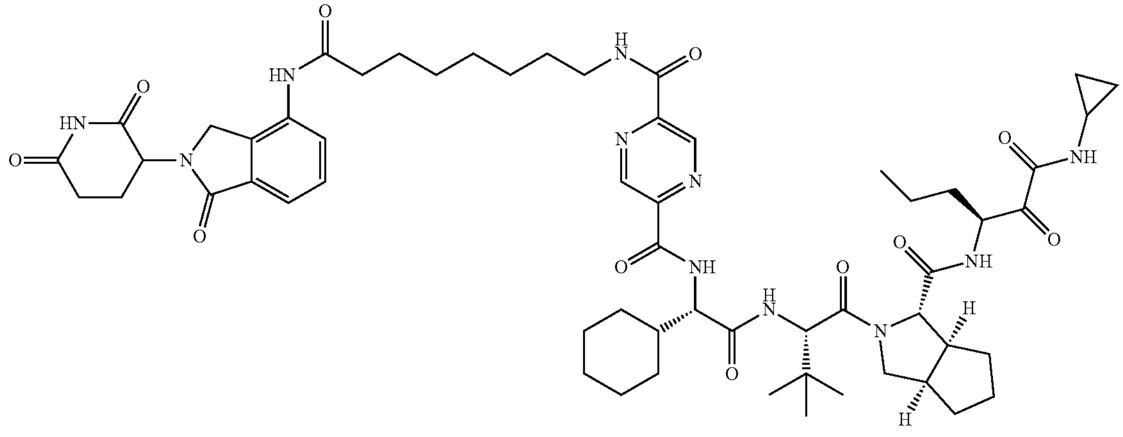
;
(5)
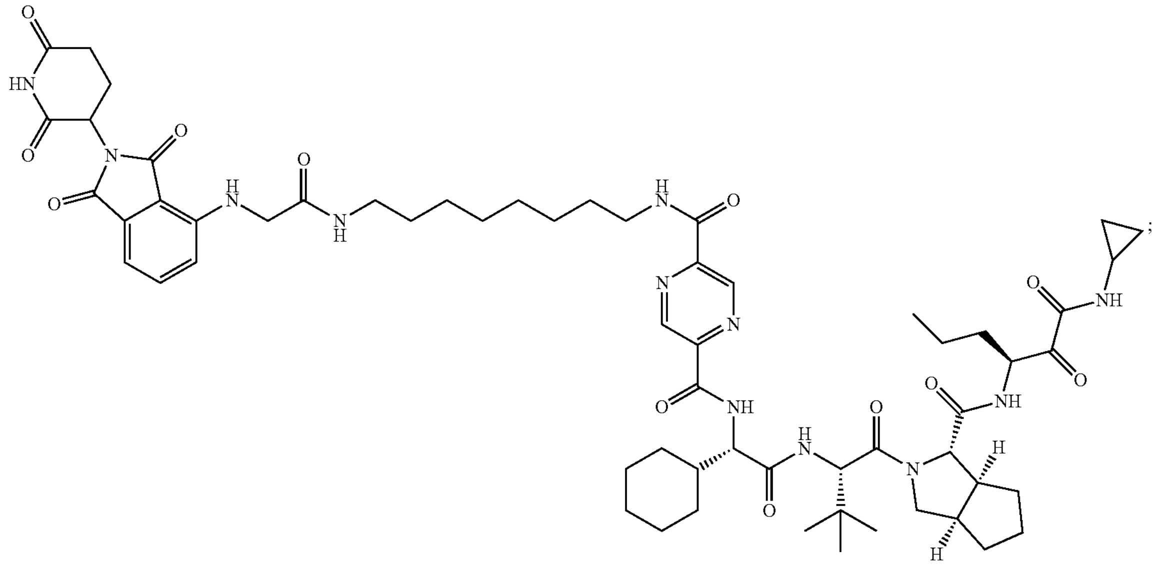
;
(6)
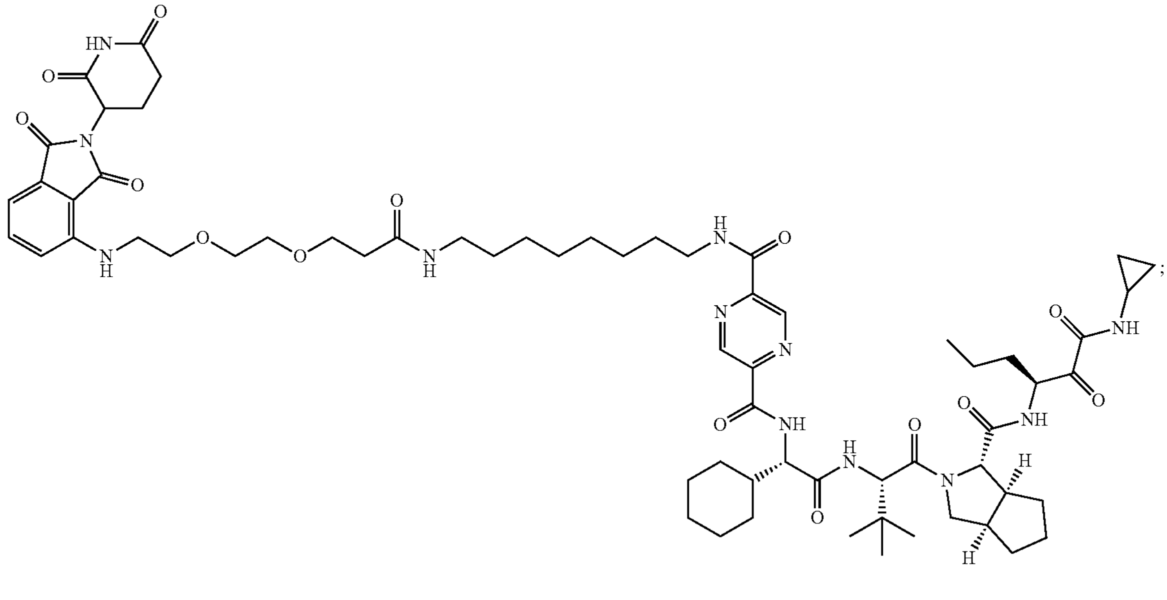
;

-continued
(7)
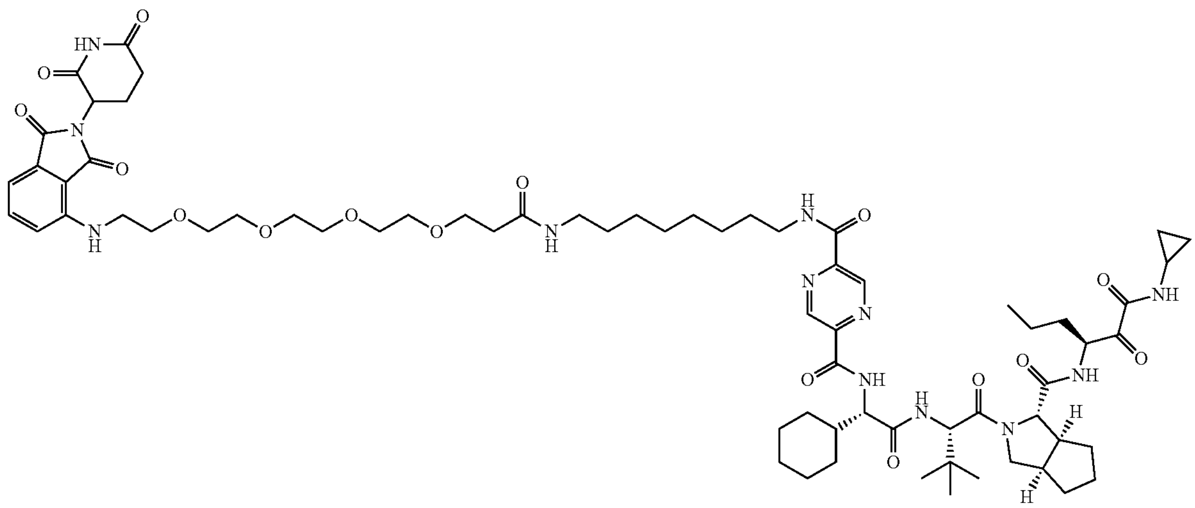
;
(8)
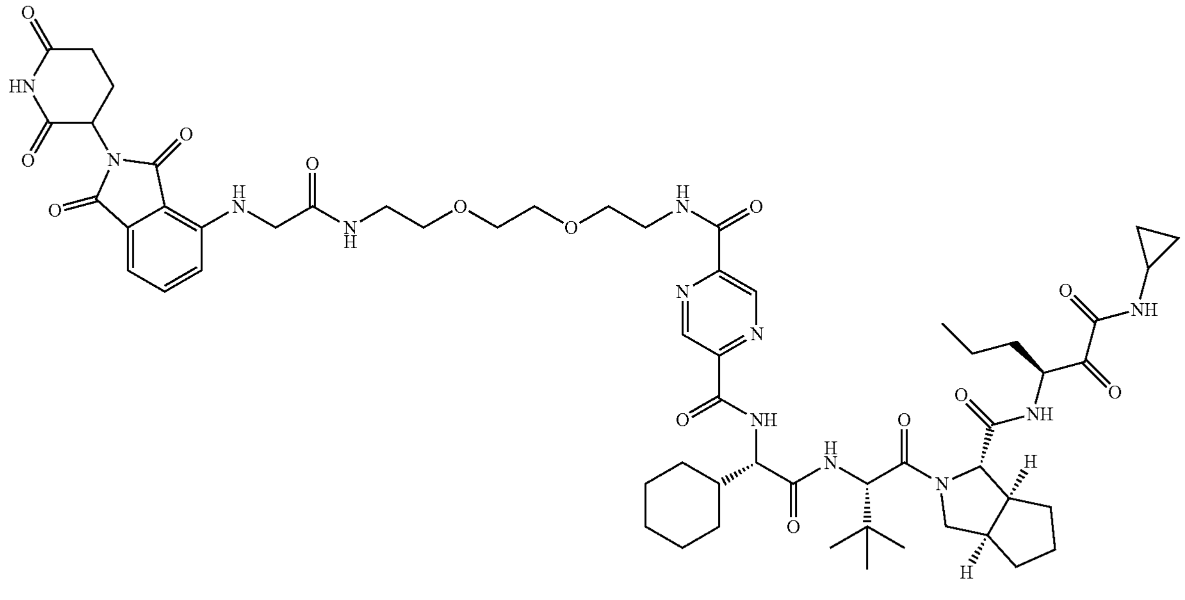
;

-continued
(9)
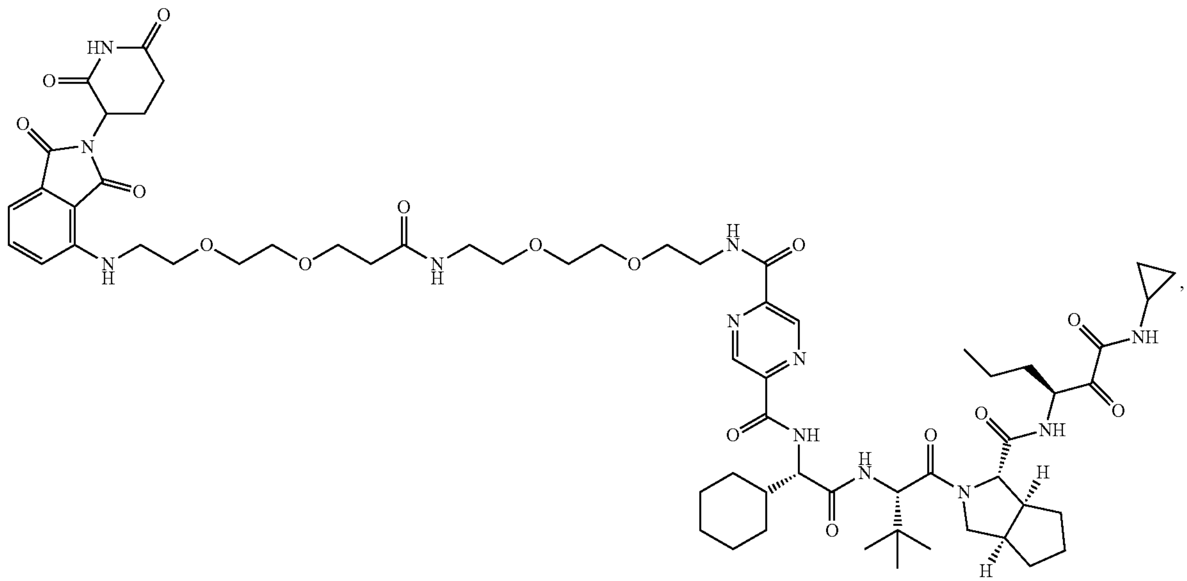
,
(10)
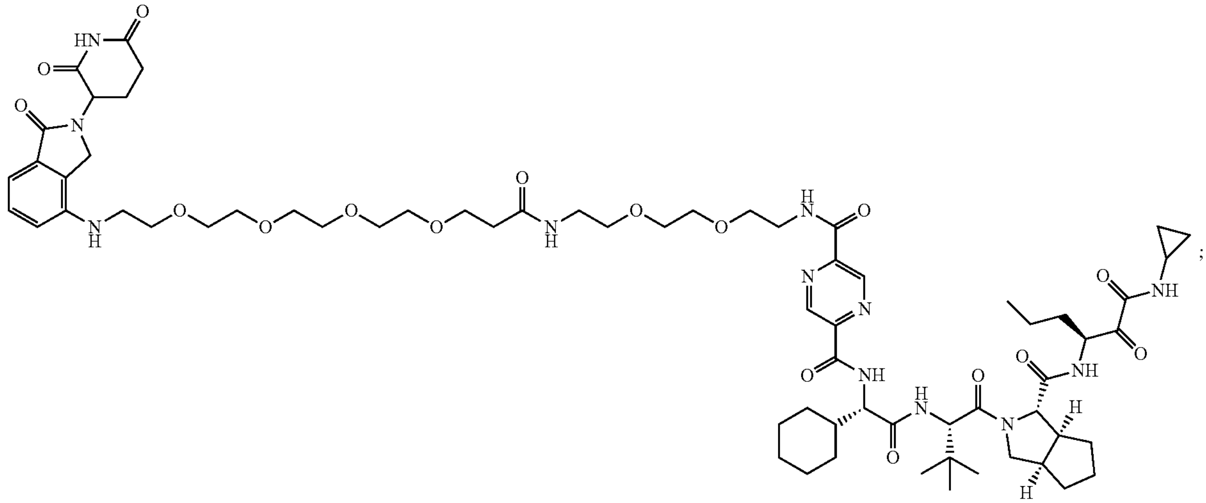
;
(12)
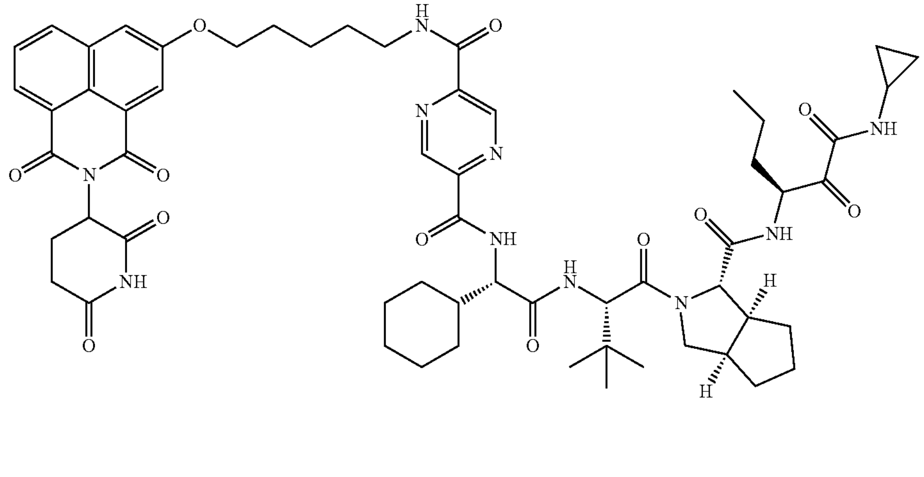
;

-continued
(13)
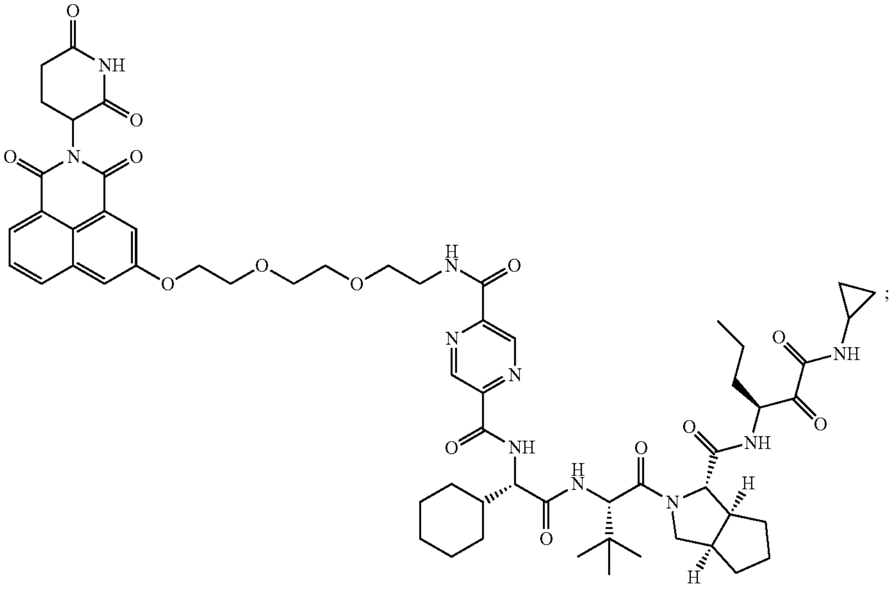
(14)
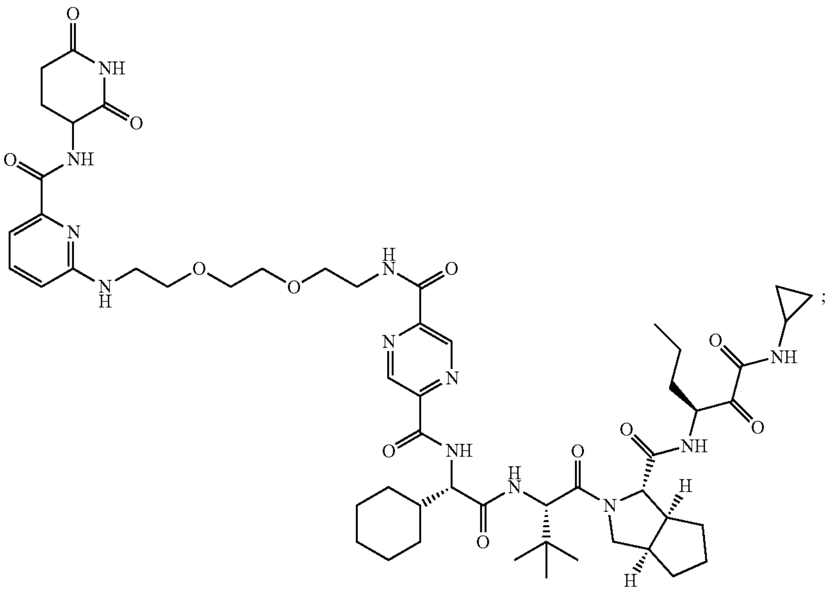

-continued
(15)
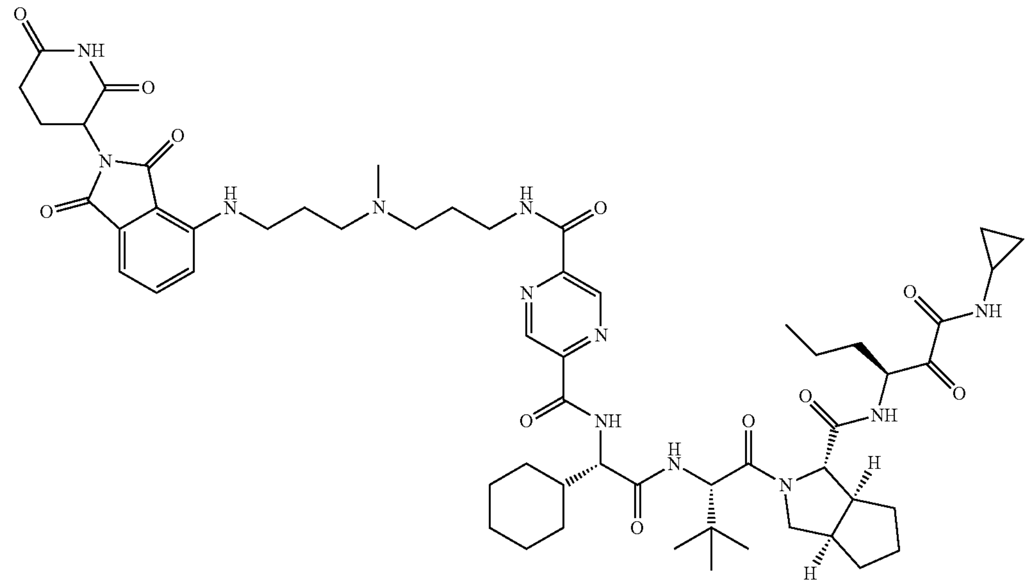
;
(16)
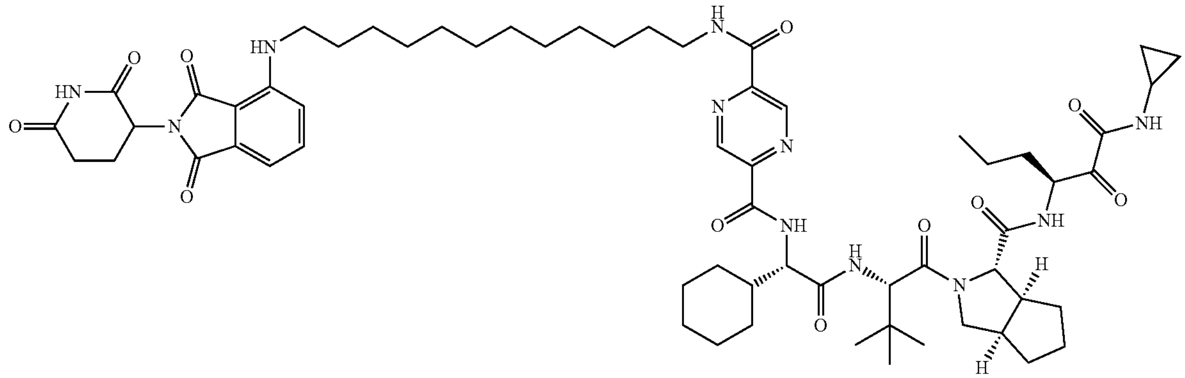
;
(17)
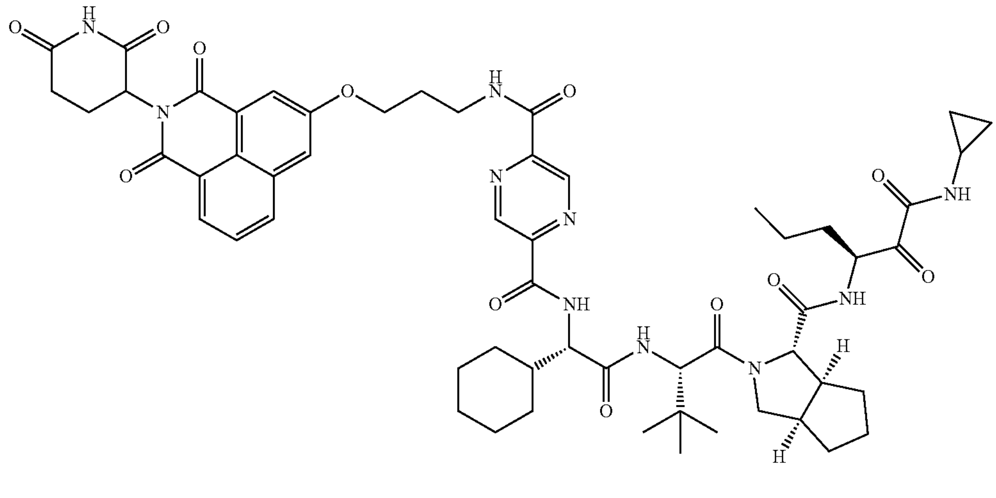
; and

-continued (18)

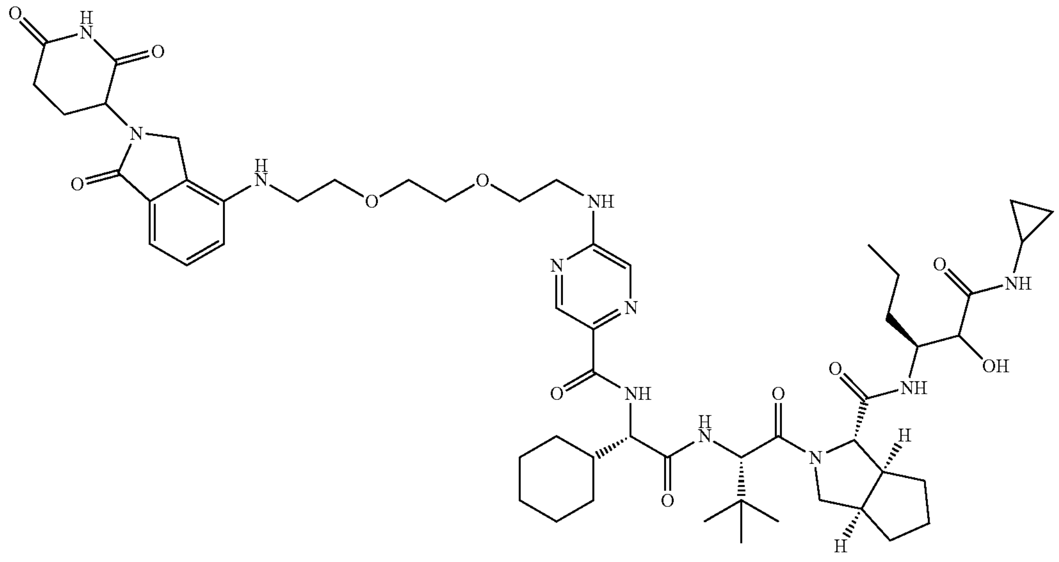

;

and pharmaceutically acceptable salts and stereoisomers thereof.

Bifunctional compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of the present invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compound of formula (I) may be an isotopic derivative in that it has at least one desired isotopic substitution of an atom, at an amount above the natural abundance of the isotope, i.e., enriched. In one embodiment, the bifunctional compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

Bifunctional compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the bifunctional compounds of the present invention may be made and used in the form of individual isomers and substantially free of other isomers, or in the form of a mixture of various isomers, e.g., racemic mixtures of stereoisomers.

In addition, the bifunctional compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

Another aspect of the present invention is directed to a method for making a bifunctional compound of formula (I) or a pharmaceutically acceptable salt or stereoisomer thereof. Broadly, the inventive compounds or pharmaceutically-acceptable salts or stereoisomers thereof, may be prepared by any process known to be applicable to the preparation of chemically related compounds. The compounds of the invention will be better understood in connection with the synthetic schemes that are described in various working examples and which illustrate non-limiting methods by which the compounds of the invention may be prepared.

Pharmaceutical Compositions

Another aspect of the present invention is directed to a pharmaceutical composition that includes a therapeutically effective amount of a bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bifunctional compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Bifunctional compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the bifunctional compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, the bifunctional compounds of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bifunctional compounds may be formulated for buccal or sublingual administration, examples of which include tablets, lozenges and gels.

The bifunctional compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating the bifunctional compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the bifunctional compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof, effective in producing the desired therapeutic response in a particular patient suffering from an HCV infection and/or an HCV-associated disease or disorder. The term "therapeutically effective amount" includes the amount of the bifunctional compound of formula (I) or a pharmaceutically acceptable salt or a stereoisomer thereof, that when administered, may induce a positive modification in the infection, disease or disorder to be treated (e.g., to selectively inhibit/degrade HCV), or is sufficient to prevent development or progression of the infection, disease or disorder, or alleviate to some extent, one or more of the symptoms of the infection, disease or disorder being treated in a subject, or which simply kills or inhibits the replication of HCV, or reduces the amount of NS3/4A protein in an HCV-infected cell.

The total daily dosage of the bifunctional compounds may be decided in accordance with standard medical practice, e.g., by the attending physician using sound medical judgment. The specific therapeutically effective dose for any particular subject will depend upon a variety of factors including any one or more of the infection, disease or disorder being treated and the severity thereof (e.g., its present status); the activity of the bifunctional compound employed; the specific type of formulation employed; the age, body weight, general health, sex and diet of the subject; the time of administration, route of administration, and rate of excretion of the bifunctional compound employed; the duration of the treatment; drugs used in combination or coincidental with the bifunctional compound employed; and like factors well known in the medical arts (see, for example, *Goodman and Gilman's The Pharmacological Basis of Therapeutics,* 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg).

In some embodiments, the bifunctional compound is administered in a dose between 100 mg per day and 250 mg per day. In other embodiments the bifunctional compound is administered in a dose between 200 mg per day and 400 mg per day, e.g., 250-350 mg per day. In yet other embodiments, the bifunctional compound is administered in a dose between 750 mg per day and 1875 mg per day, e.g., 375 mg three times per day (7-9 hours apart). In some embodiments, individual dosages may be formulated to contain the desired dosage amount depending upon the number of times the compound is administered per day.

Methods of Use

Bifunctional compounds of formula (I) and their pharmaceutically acceptable salts and stereoisomers may be useful in the treatment of HCV infection. In some embodiments, the subject has an HCV-associated disease and disorder. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The present methods thus include administering a therapeutically effective amount of a bifunctional compound of formula (I) to a subject in need thereof. In some embodiments, subjects with HCV infection have contracted liver disease (e.g., hepatitis, cirrhosis and liver cancer), in which case the methods may still be effective in treating the underlying and persistent HCV infection and may result in a more positive (e.g., stable) clinical outcome. The term "subject" (or "patient") as used herein includes all members of the animal kingdom prone to or suffering from the indicated infection, disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "suffering from or suspected of suffering from" a specific infection, disease or disorder may have a sufficient number of risk factors or presents with a sufficient number or combination of signs or symptoms such that a medical professional could diagnose or suspect that the subject was suffering from the infection, disease or disorder. Thus, subjects suffering from, and suspected of suffering from, a specific infection, disease or disorder are not necessarily two distinct groups.

In general, methods of using the bifunctional compounds of the present invention include administering to a subject in need thereof a therapeutically effective amount of a compound of the present invention. The modes of administration (e.g., oral, parenteral) may be determined in accordance with the standard medical practice.

The bifunctional compounds of the present invention may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

The methods of the present invention may entail administration of bifunctional compounds of the present invention or pharmaceutical compositions thereof to the patient in a single dose or in multiple doses (e.g., 1, 2, 3, 4, 5, 6, 7, 8, 10, 15, 20, or more doses). For example, the frequency of administration may range from five times a day up to about once every eight weeks. In some embodiments, the frequency of administration ranges from about five times a day for 1, 2, 3, 4, 5, or 6 weeks, and in other embodiments entails a 28-day cycle which includes daily administration for 3 weeks (21 days). In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

Bifunctional compounds of formula (I) and their pharmaceutically acceptable salts and stereoisomers may be used in combination with at least one other active agent in treating HVC infections and HCV-associated diseases and disorders. The term "in combination" in this context means that the agents are co-administered, which includes substantially contemporaneous administration, by way of the same or separate dosage forms, or sequentially, e.g., as part of the same treatment regimen or by way of successive treatment regimens. Thus, if given sequentially, at the onset of administration of the second compound, the first of the two compounds is in some cases still detectable at effective concentrations at the site of treatment.

In some embodiments, the treatment regimen may include administration of a compound of formula (I) in combination with one or more additional therapeutics known for use in treating the infection, disease or disorder. The dosage of the additional antiviral therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; *Physician's Desk Reference,* 60th ed., 2006. For example, anti-viral agents that may be used in combination with the inventive compounds are known in the art.

In some embodiments, a bifunctional compound of formula (I) may be used in combination with PEG-interferon-α or and/or ribavirin.

In some embodiments, a bifunctional compound of the present invention may be used in combination with one or more HCV NS3/4A protease inhibitors including asunaprevir, boceprevir, grazoprevir, glecaprevir, paritaprevir, simeprevir, telaprevir, sofosbuvir, ledipasvir, paritaprevir, ritonavir, ombitasvir, dasabuvir, daclatasvir, elbasvir, grazoprevir and velpatasvir.

In some embodiments, a bifunctional compound of the invention may be used combination with a fixed-dose combination antiviral including: COMBIVIR® (lamivudine/zidovudine), KALETRA® (also known as ALUVIA™) (lopinavir/ritonavir), TRIZIVIR® (abacavir/lamivudine/zidovudine), EPZICOM® (also known as KIVEXA®) (abacavir/lamivudine), TRIOMUNE (lamivudine/stavudine/nevirapine), DUOVIR-N(lamivudine/zidovudine/nevirapine), TRUVADA® (emtricitabine/tenofovir/disoproxil), ATRIPLA® (emtricitabine/tenofovir/disoproxil/efavirenz), COMPLERA® (also known as EVIPLERA®) (emtricitabine/tenofovir/disoproxil/rilpivirine), STRIBILD® (emtricitabine/tenofovir/disoproxil/elvitegravir/cobicistat), TRIUMEQ® (abacavir/lamivudine/dolutegravir), EVOTAZ® (atazanavir/cobicistat), PREZCOBIX® (also known as REZOLSTA®) (darunavir/cobicistat), DUTREBIS™ (lamivudine/raltegravir), GENVOYA® (emtricitabine/tenofovir/alafenamide/elvitegravir/cobicistat), ODEFSEY® (emtricitabine/tenofovir/alafenamide/rilpivirine), DESCOVY® (emtricitabine/tenofovir/alafenamide), JULUCA® (rilpivirine/dolutegravir), SYMFI™/SYMFI LO™ (lamivudine/tenofovir/disoproxil/efavirenz), BIKTARVY® (emtricitabine/tenofovir/alafenamide/bictegravir), CIMDUO™ (lamivudine/tenofovir/disoproxil), SYMTUZA® (emtricitabine/tenofovir/alafenamide/darunavir/cobicistat), EPCLUSA® (sofosbuvir/velpatasvir), HARVONI® (ledipasvir/sofosbuvir), VIEKIRA/VIEKIRA PAK™ (paritaprevir/ritonavir/ombitasvir/dasabuvir), TECHNIVIE™ (paritaprevir/ritonavir/ombitasvir), SMV/SOF (simeprevir/sofosbuvir), DCV/SOF (daclatasvir/sofosbuvir), ZEPATIER™ (elbasvir/grazoprevir) and MAVYRET™ (glecaprevir/pibrentasvir).

In some cases patients may suffer from co-viral infections, i.e., they may be infected with more than one type of virus. For example, HCV/HIV and HCV/HBV co-infections may occur. Thus, in some embodiments, a bifunctional compound of the present invention may be used in combination with one or more antiviral drugs including abacavir, acyclovir, adefovir, alafenamide, amantadine, amprenavir, ampligen, aplaviroc, arbidol, atazanavir, atripla, anti-caprine antibody, balavir, BCX4430, BI224436, b12, bictegravir, cabotegravir, cidofovir, combivir, cobicistat, cytarabine, dolutegravir, darunavir, DCM205, DARPins, delaviridine, didanosine, disoproxil, docosanol, edoxudine, efavirenz, emtricitabine, enfuvirtide, entecavir, ecoliever, elvitegravir, epigallocatechin gallate, etravirine, famciclovir, fomivirsen, fosamprenavir, foscarnet, fosfonet, fostemsavir, ganciclovir, gemcitabine, griffithsin, ibacitabine, imunovir, idoxuridine, imiquimod, indinavir, inosine, interferon type III, interferon type II, interferon type I, interferon, lamivudine, ledipasvir, lopinavir, loviride, maraviroc, moroxydine, methisazone, MK-2048, nelfinavir, nevirapine, nexavir, nitazoxanide, norvir, oseltamivir, penciclovir, peramivir, pibrentasvir, pleconaril, plerixafor, podophyllotoxin, PRO 140, raltegravir, rilpivirine, rimantadine, pyramidine, saquinavir, simeprevir, sofosbuvir, stavudine, telbivudine, tenofovir, tenofovir disoproxil, TNX-355, tipranavir, trifluridine, trizivir, tromantadine, truvada, valacyclovir, valganciclovir, vicriviroc, vidarabine, viramidine, VIR-576, zalcitabine, zanamivir, and zidovudine.

In some embodiments, the compound of formula (I) and the additional antiviral therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part.

When the active components of the combination are not administered in the same pharmaceutical composition, it is understood that they can be administered in any order to a subject in need thereof. For example, a bifunctional compound of the present invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional antiviral therapeutic, to a subject in need thereof. In various aspects, the antiviral therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the antiviral therapeutics are administered within the same office visit. In another example, the combination antiviral therapeutics may be administered at 1 minute to 24 hours apart.

In some embodiments, the bifunctional compound of the present invention and the additional agent or therapeutic (e.g., an antiviral therapeutic) are cyclically administered. Cycling therapy involves the administration of one antiviral therapeutic for a period of time, followed by the administration of a second anti-viral therapeutic for a period of time and repeating this sequential administration, i.e., the cycle, in order to reduce the development of resistance to one or both of the antiviral therapeutics, to avoid or reduce the side effects of one or both of the antiviral therapeutics, and/or to improve the efficacy of the therapies. In one example, cycling therapy involves the administration of a first antiviral therapeutic for a period of time, followed by the administration of a second antiviral therapeutic for a period of time, optionally, followed by the administration of a third antiviral therapeutic for a period of time and so forth, and repeating this sequential administration, i.e., the cycle in order to reduce the development of resistance to one of the antiviral therapeutics, to avoid or reduce the side effects of one of the antiviral therapeutics, and/or to improve the efficacy of the antiviral therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of formula (I) or a pharmaceutical composition. The kits or pharmaceutical systems of the invention may also include printed instructions for using the bifunctional compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(6-(2-(2,6-dioxopiperidin-3-yl)-1-oxoisoindolin-4-ylamino)hexyl)pyrazine-2,5-dicarboxamide (1)

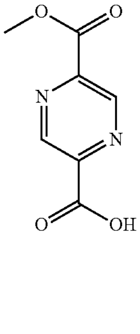

+

-continued

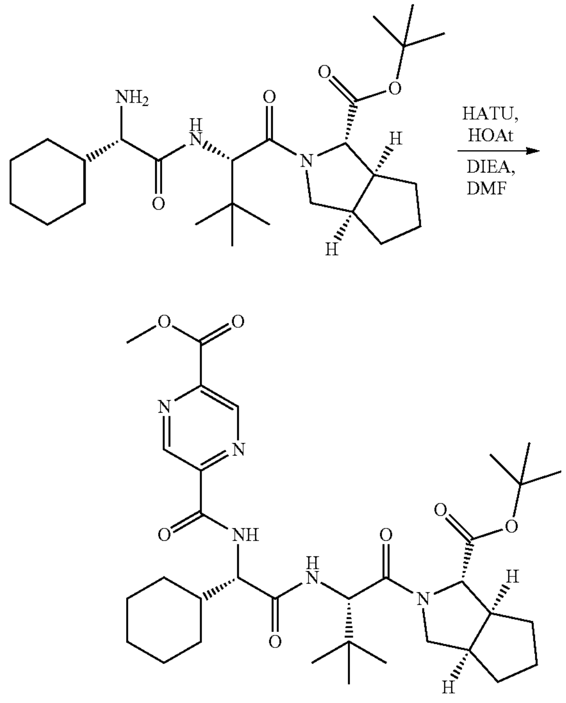

To a solution of 5-(methoxycarbonyl)pyrazine-2-carboxylic acid (208 mg, 1.14 mmol) and (1S,3aR,6aS)-tert-butyl 2-((S)-2-((S)-2-amino-2-cyclohexylacetamido)-3,3-dimethylbutanoyl)octahydrocyclopenta[c]pyrrole-1-carboxylate (530 mg, 1.14 mmol) in DMF (8 mL), DIEA (736 mg, 5.70 mmol), 1-[Bis(dimethylamino)methylene]-1H-1,2,3-triazolo[4,5-b]pyridinium 3-oxid hexafluorophosphate (HATU) (867 mg, 2.28 mmol) and 1-hydroxy-7-azabenzotriazole (HOAт) (31 mg, 0.228 mmol) were added at 0° C. The reaction was stirred for 10 minutes and then quenched with ice water. The mixture was stirred for 30 minutes at 0° C. The resulting white precipitate was filtered off and washed with ice water. The white precipitated was dried under vacuum to obtain (1S,3aR,6aS)-tert-butyl 2-((S)-2-((S)-2-cyclohexyl-2-(5-(methoxycarbonyl)pyrazine-2-carboxamido)acetamido)-3,3-dimethylbutanoyl)octahydrocyclopenta[c]pyrrole-1-carboxylate (560 mg, 0.89 mmol, 78% yield).

LC/MS m/z calculated for $[M+H]^+$ 628.4, found 628.4.

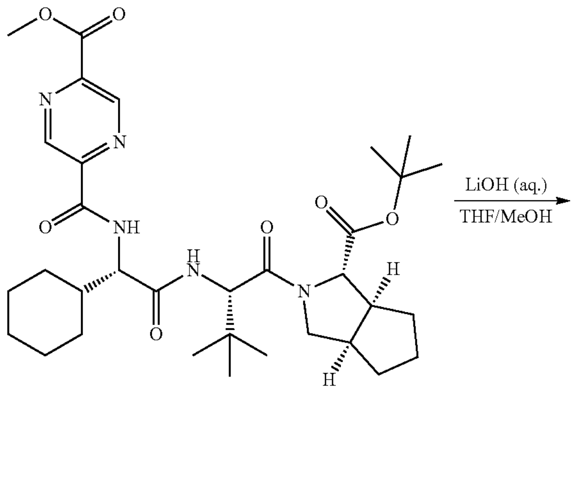

-continued

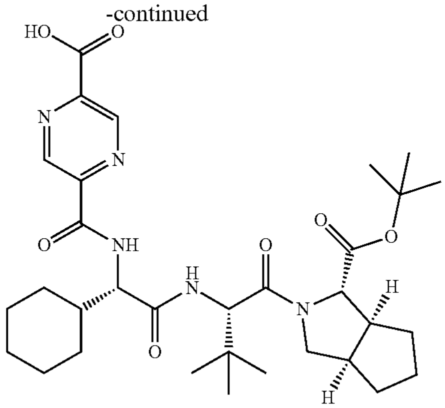

To a solution of (1S,3aR,6aS)-tert-butyl 2-((S)-2-((S)-2-cyclohexyl-2-(5-(methoxycarbonyl)pyrazine-2-carboxamido)acetamido)-3,3-dimethylbutanoyl)octahydrocyclopenta[c]pyrrole-1-carboxylate (250 mg, 0.40 mmol) in THF/MeOH (1.6 mL/0.1 mL) LiOH (aqueous, 0.80 mL, 0.80 mmol, 1 M) was added at room temperature. The reaction was stirred overnight. To the mixture, HCl (aq. 2 M) was added to acidify the solution to pH 3. The mixture was extracted with EtOAc (10 mL×3). The combined organic layers were evaporated under vacuum to get crude 5-((S)-2-((S)-1-((1S,3aR,6aS)-1-(tert-butoxycarbonyl)hexahydrocyclopenta[c]pyrrol-2(1H)-yl)-3,3-dimethyl-1-oxobutan-2-ylamino)-1-cyclohexyl-2-oxoethylcarbamoyl)pyrazine-2-carboxylic acid (223 mg, 0.364 mmol, 91% yield) without any further purification.

LC/MS m/z calculated for $[M+H]^+$ 614.3, found 614.3.

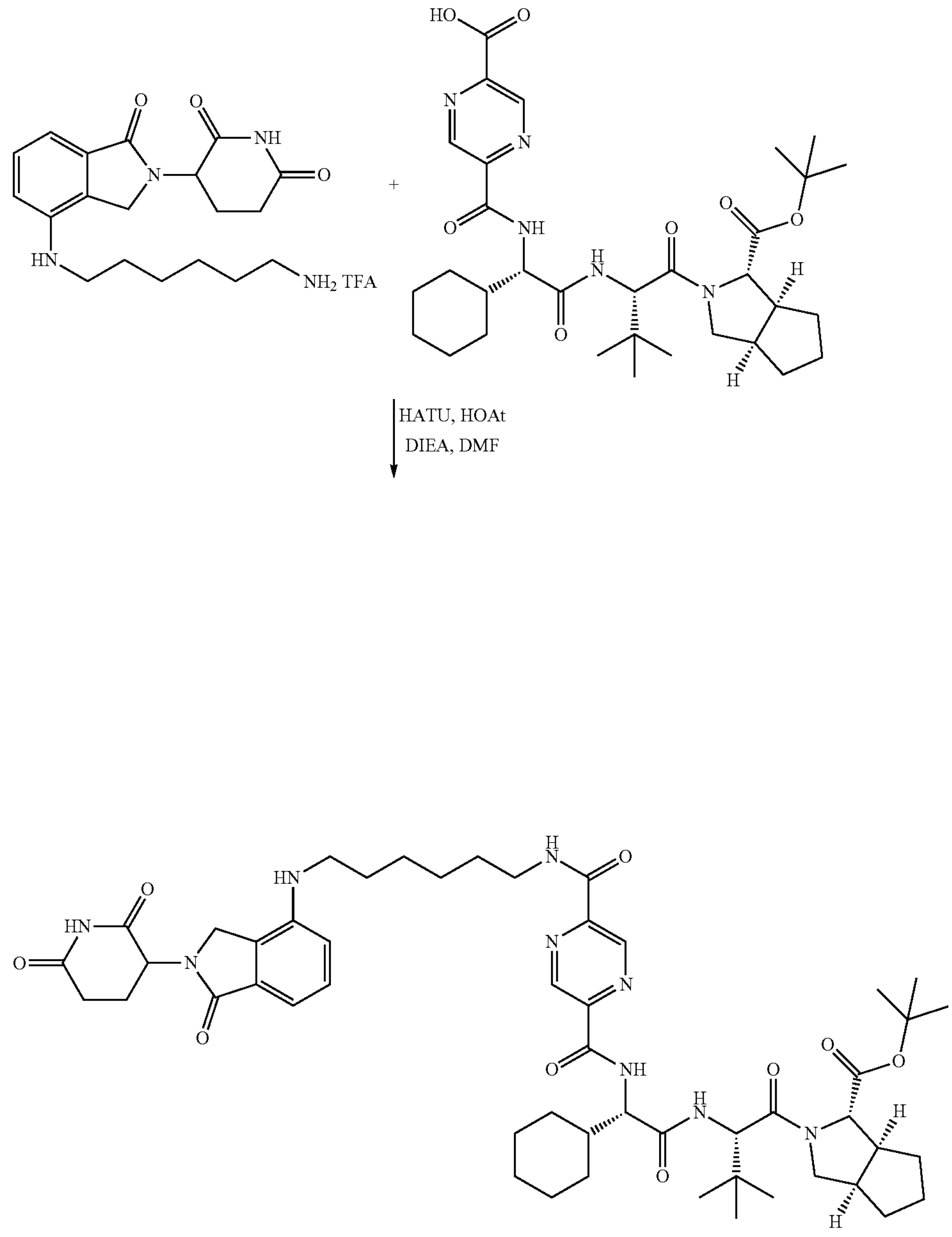

To a solution of 3-(4-(6-aminohexylamino)-1-oxoisoindolin-2-yl)piperidine-2,6-dione TFA salt (70 mg, 0.15 mmol) and 5-((S)-2-((S)-1-((1S,3aR,6aS)-1-(tert-butoxycarbonyl)hexahydrocyclopenta[c]pyrrol-2(1H)-yl)-3,3-dimethyl-1-oxobutan-2-ylamino)-1-cyclohexyl-2-oxoethylcarbamoyl)pyrazine-2-carboxylic acid (76 mg, 0.12 mmol) in DMF (1 mL), DIEA (78 mg, 0.60 mmol), HATU (91 mg, 0.24 mmol) and HOAт (3.3 mg, 0.024 mmol) were added at 0° C. The reaction was stirred for 10 minutes. The reaction mixture was purified with HPLC to get (1S,3aR,6aS)-tert-butyl 2-((2S)-2-((2S)-2-cyclohexyl-2-(5-(6-(2-(2,6-dioxopiperidin-3-yl)-1-oxoisoindolin-4-ylamino)hexylcarbamoyl) pyrazine-2-carboxamido)acetamido)-3,3-dimethylbutanoyl) octahydrocyclopenta[c]pyrrole-1-carboxylate (17 mg, 0.0178 mmol, 12% yield).

LC/MS m/z calculated for $[M+H]^+$ 954.5, found 954.5.

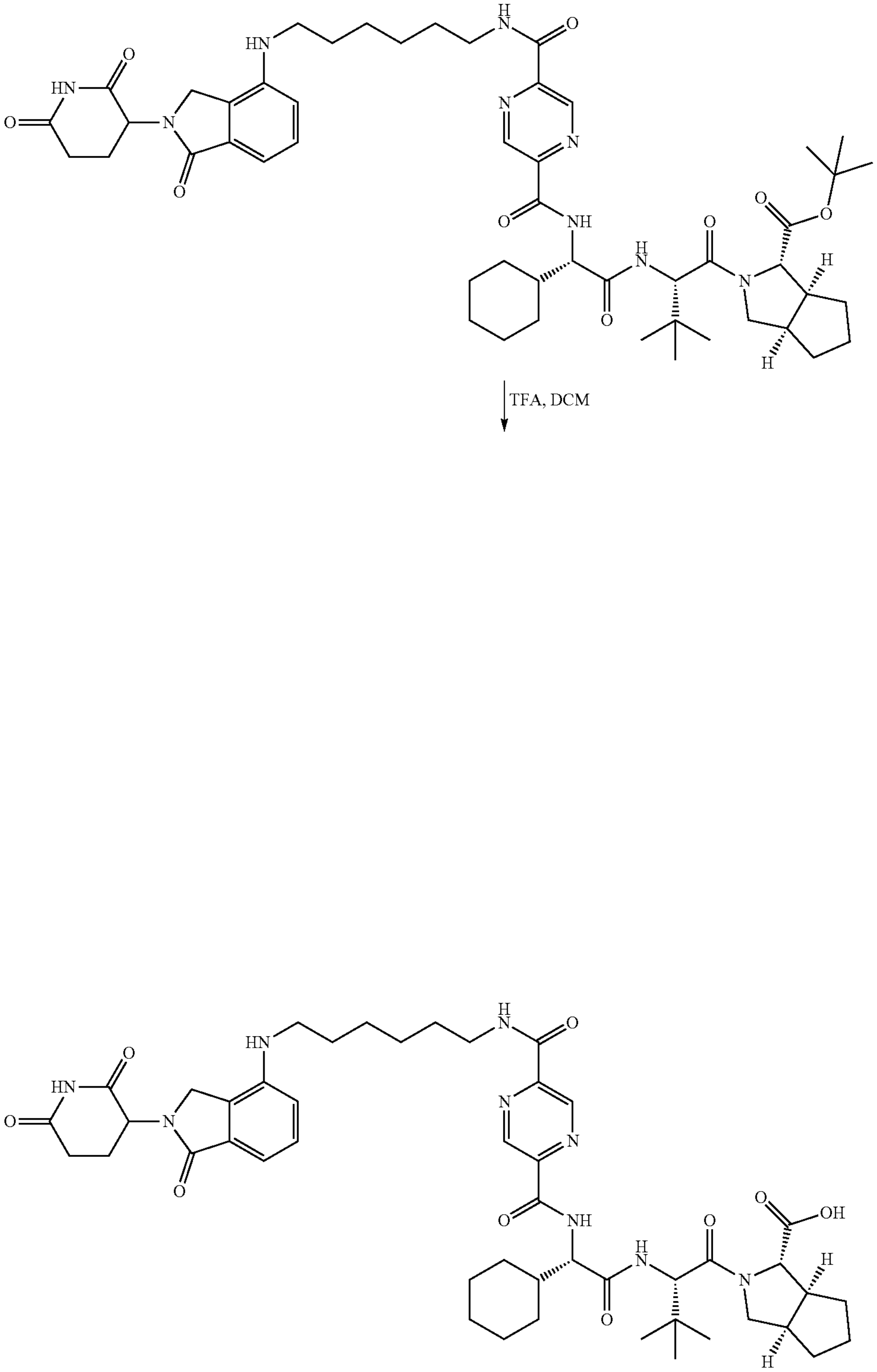

To a solution of (1S,3aR,6aS)-tert-butyl 2-((2S)-2-((2S)-2-cyclohexyl-2-(5-(6-(2-(2,6-dioxopiperidin-3-yl)-1-oxoisoindolin-4-ylamino)hexylcarbamoyl)pyrazine-2-carboxamido)acetamido)-3,3-dimethylbutanoyl)octahydrocyclopenta[c]pyrrole-1-carboxylate (17 mg, 0.0178 mmol) in DCM (1 mL), TFA (1 mL) was added at room temperature. The reaction was stirred for 1 hour. The reaction was evaporated under vacuum to obtain (1S,3aR,6aS)-2-((2S)-2-((2S)-2-cyclohexyl-2-(5-(6-(2-(2,6-dioxopiperidin-3-yl)-1-oxoisoindolin-4-ylamino)hexylcarbamoyl)pyrazine-2-carboxamido)acetamido)-3,3-dimethylbutanoyl)octahydrocyclopenta[c]pyrrole-1-carboxylic acid (16 mg, 0.0178 mmol, 100% yield) without any further purification.

LC/MS m/z calculated for $[M+H]^+$ 898.5, found 898.5.

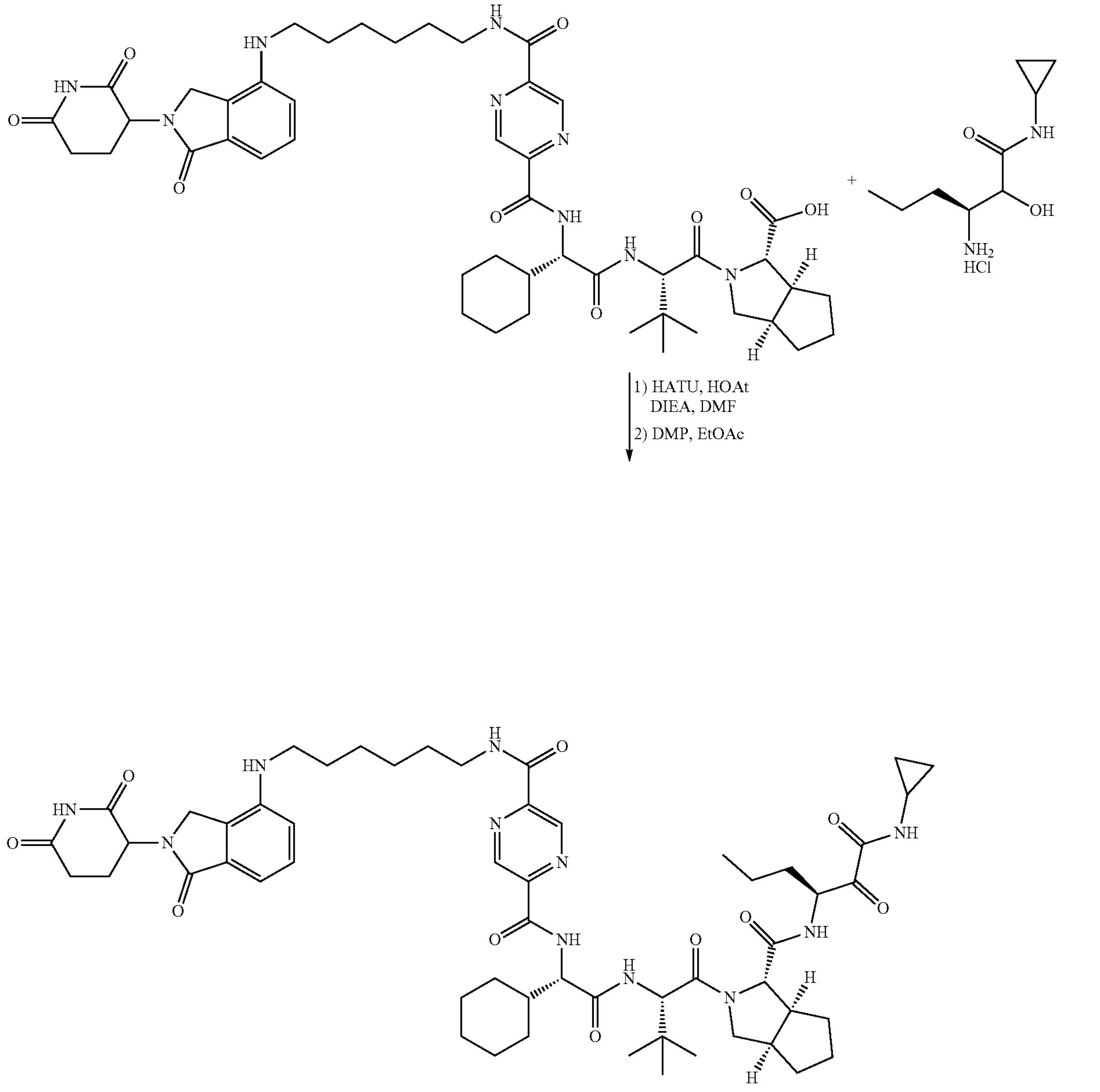

(1)

To a solution of (1S,3aR,6aS)-2-((2S)-2-((2S)-2-cyclohexyl-2-(5-(6-(2-(2,6-dioxopiperidin-3-yl)-1-oxoisoindolin-4-ylamino)hexylcarbamoyl)pyrazine-2-carboxamido)acetamido)-3, 3-dimethylbutanoyl)octahydrocyclopenta[c]pyrrole-1-carboxylic acid (16 mg, 0.0178 mmol) and (3S)-3-amino-N-cyclopropyl-2-hydroxyhexanamide HCl salt (4 mg, 0.0178 mmol) in DMF (1 mL), DIEA (12 mg, 0.089 mmol), HATU (13.5 mg, 0.0356 mmol) and HOAт (0.5 mg, 0.00356 mmol) were added at 0° C. The reaction was stirred for 10 minutes. The solvent was evaporated under vacuum to obtain the crude product without any further purification. The residue was dissolved in ethyl acetate (1 mL). Dess-Martin periodinane (DMP) (10 mg, 0.023 mmol) was added to the mixture at 0° C. The reaction was stirred for 6 hours. After Celite® filtration and evaporation of the solvent, the crude product was purified with HPLC to obtain compound 1 (3.6 mg, 0.0034 mmol, 19% yield in two steps).

LC/MS m/z calculated for $[M+H]^+$ 1064.6, found 1064.6.

Example 2: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(2,6-dioxopiperidin-3-yl)-1-oxoisoindolin-4-ylamino)ethoxy)ethoxy)ethyl)pyrazine-2,5-dicarboxamide (2)

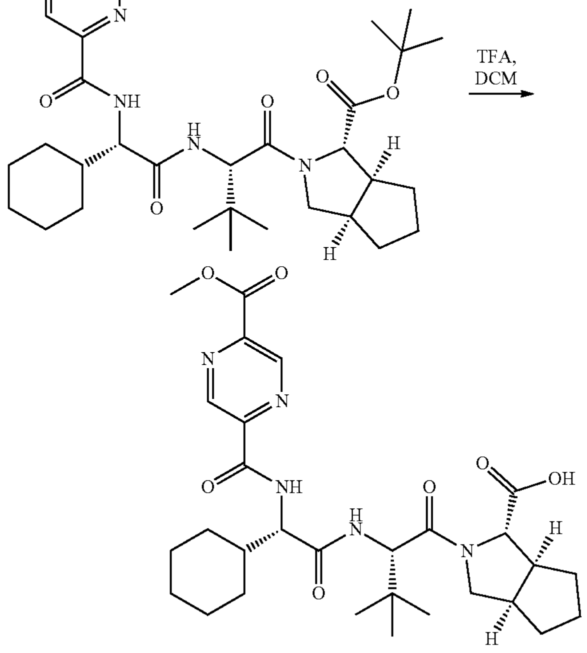

To a solution of (1S,3aR,6aS)-tert-butyl 2-((S)-2-((S)-2-cyclohexyl-2-(5-(methoxycarbonyl)pyrazine-2-carboxamido)acetamido)-3,3-dimethylbutanoyl)octahydrocyclopenta[c]pyrrole-1-carboxylate (560 mg, 0.89 mmol) in DCM (5 mL), TFA (2 mL) was added at room temperature. The reaction was stirred for 1 hour. The solvent was removed under vacuum to obtain (1S,3aR,6aS)-2-((S)-2-((S)-2-cyclohexyl-2-(5-(methoxycarbonyl)pyrazine-2-carboxamido)acetamido)-3,3-dimethylbutanoyl)octahydrocyclopenta[c]pyrrole-1-carboxylic acid (510 mg, 0.89 mmol, 100% yield) without any further purification.

LC/MS m/z calculated for $[M+H]^+$ 572.3, found 572.3.

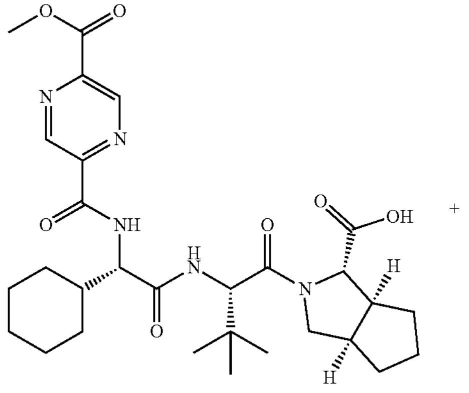

-continued

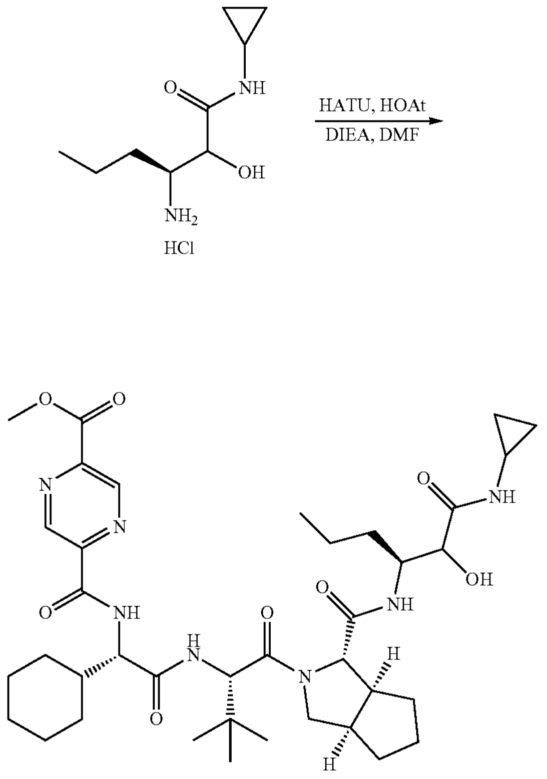

To a solution of (1S,3aR,6aS)-2-((S)-2-((S)-2-cyclohexyl-2-(5-(methoxycarbonyl)pyrazine-2-carboxamido)acetamido)-3,3-dimethylbutanoyl)octahydrocyclopenta[c]pyrrole-1-carboxylic acid (510 mg, 0.89 mmol) and (3S)-3-amino-N-cyclopropyl-2-hydroxyhexanamide HCl salt (198 mg, 0.89 mmol) in DMF (5 mL), DIEA (575 mg, 4.45 mmol), HATU (677 mg, 1.78 mmol) and HOAτ (24 mg, 0.178 mmol) were added at 0° C. The reaction was stirred for 10 minutes and then quenched with ice water. The mixture was stirred for 30 minutes at 0° C. The resulting white precipitate was filtered off and washed with ice water. The white solid was dried under vacuum to get methyl 5-((1S)-1-cyclohexyl-2-((2S)-1-((1S,3aR,6aS)-1-((3 S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylate (590 mg, 0.80 mmol, 90% yield).

LC/MS m/z calculated for $[M+H]^+$ 740.4, found 740.4.

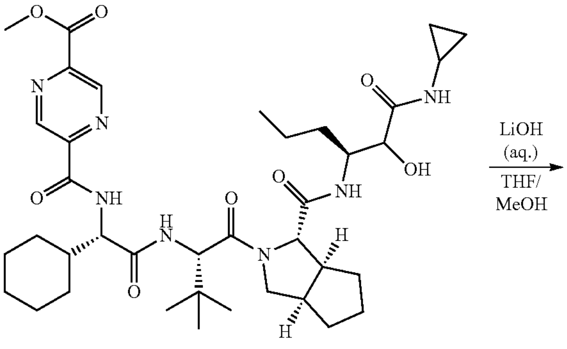

-continued

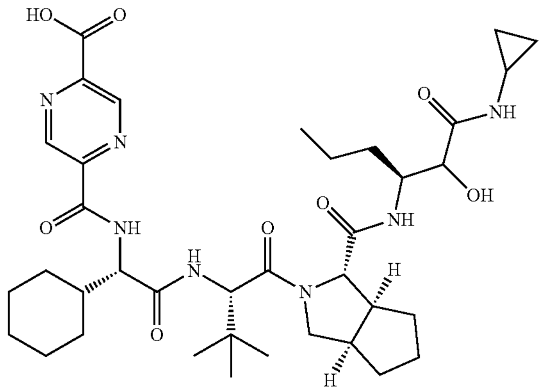

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylate (590 mg, 0.80 mmol) in THF/MeOH (5 mL/0.3 mL), LiOH (aq., 1.6 mL, 1.60 mmol, 1 M) was added at room temperature. The reaction was stirred overnight. To the mixture, HCl (aq. 2 M) was added to acidify the solution to pH 3. The mixture was extracted with EtOAc (20 mL×3). The combined organic layers were evaporated under vacuum to get 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (568 mg, 0.784 mmol, 98% yield) without any further purification.

LC/MS m/z calculated for $[M+H]^+$ 726.4, found 726.4.

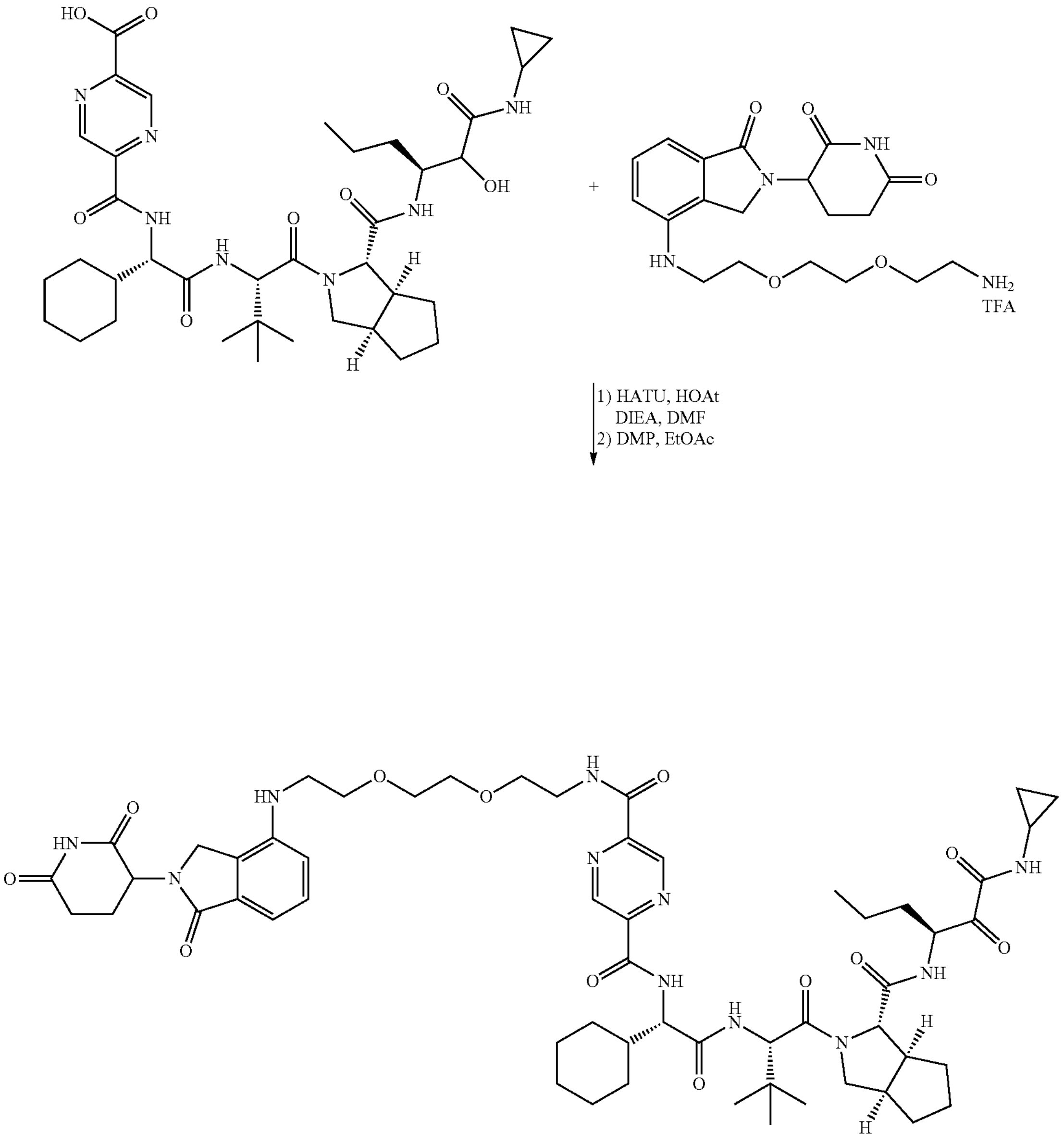

(2)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (50 mg, 0.069 mmol) and 3-(4-(2-(2-(2-aminoethoxy)ethoxy)ethylamino)-1-oxoisoindolin-2-yl)piperidine-2,6-dione TFA salt (27 mg, 0.069 mmol) in DMF (1 mL), DIEA (45 mg, 0.0345 mmol), HATU (52.4 mg, 0.138 mmol) and HOAт (1.9 mg, 0.0138 mmol) were added at 0° C. The reaction was stirred for 10 minutes. The solvent was evaporated under vacuum to obtain the crude product without any further purification. The residue was dissolved in ethyl acetate (1 mL). DMP (16 mg, 0.038 mmol) was added to the mixture at 0° C. The reaction was stirred for 6 hours. After Celite® filtration and evaporation of the solvent, the crude product was purified with HPLC to get compound 2 (6.3 mg, 0.0057 mmol, 83% yield in two steps).

LC/MS m/z calculated for $[M+H]^+$ 1096.6, found 1096.6.

Example 3: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(2,6-dioxopiperidin-3-yl)-1,3-dioxoisoindolin-4-ylamino)ethoxy)ethoxy)ethyl)pyrazine-2,5-dicarboxamide (3)

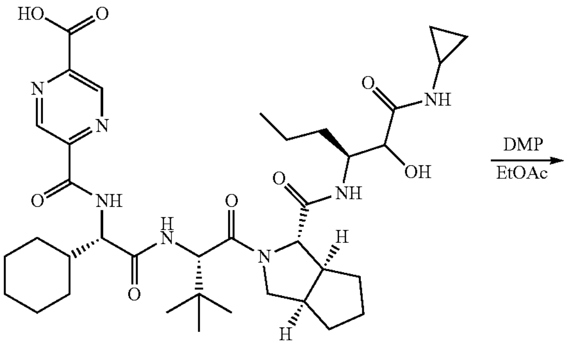

-continued

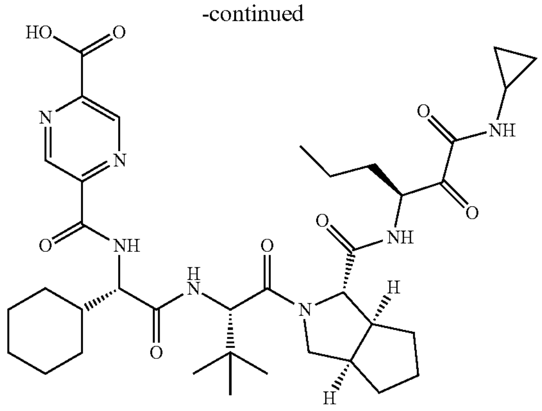

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.027 mmol) in ethyl acetate (1 mL), DMP (23.4 mg, 0.055 mmol) was added at 0° C. The mixture was stirred at 0° C. for 6 hours. The reaction was filtered with Celite® and the filtrate was concentrated under vacuum. The residue was purified with ISCO CombiFlash© chromatography to get 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (13 mg, 0.018 mmol, 67% yield).

LC/MS m/z calculated for [M+H]+ 724.4, found 724.4.

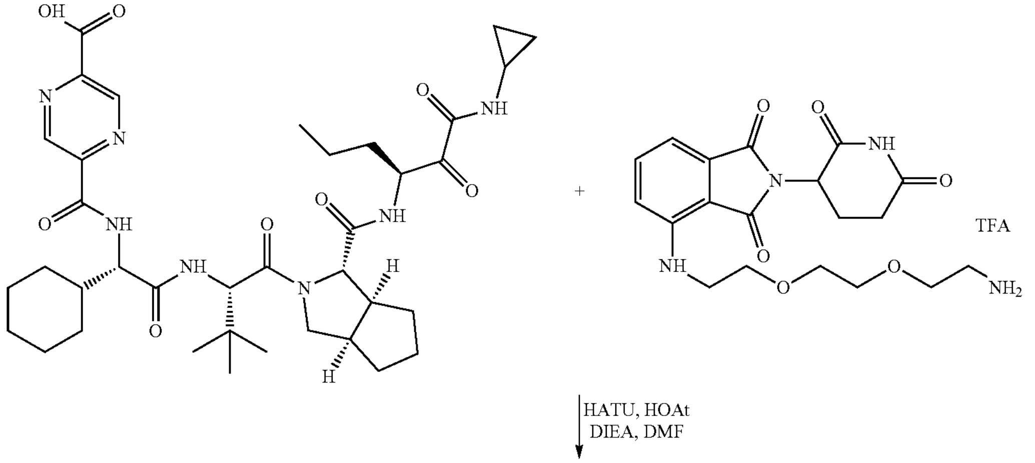

-continued

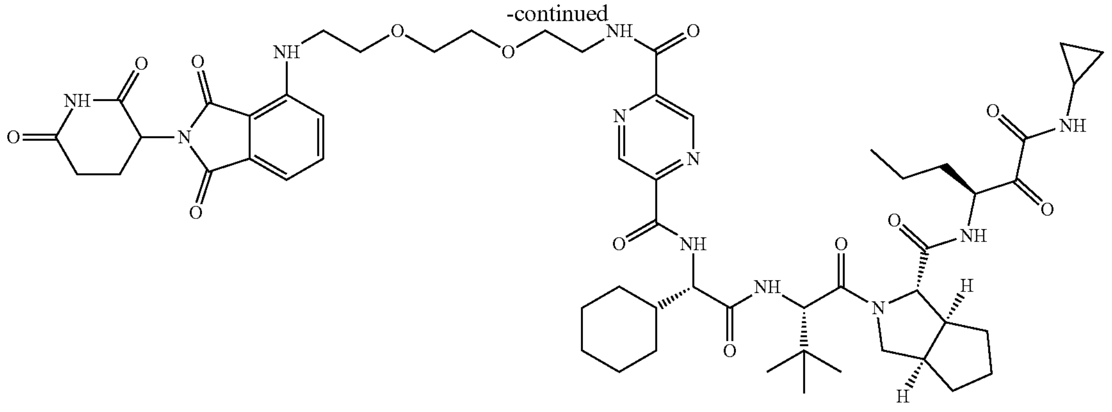

(3)

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (10 mg, 0.0138 mmol) and 4-(2-(2-(2-aminoethoxy)ethoxy)ethylamino)-2-(2,6-dioxopiperidin-3-yl)isoindoline-1,3-dione TFA salt (7 mg, 0.0138 mmol) in DMF (1 mL), DIEA (9 mg, 0.069 mmol), HATU (10.5 mg, 0.0276 mmol) and HOAt (0.4 mg, 0.00276 mmol) were added at 0° C. The reaction was stirred for 10 minutes. The reaction mixture was purified with HPLC to get compound 3 (12 mg, 0.0108 mmol, 78% yield).

LC/MS m/z calculated for $[M+H]^+$ 1110.6, found 1110.6.

Example 4: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(8-(2-(2,6-dioxopiperidin-3-yl)-1-oxoisoindolin-4-ylamino)-8-oxooctyl)pyrazine-2,5-dicarboxamide (4)

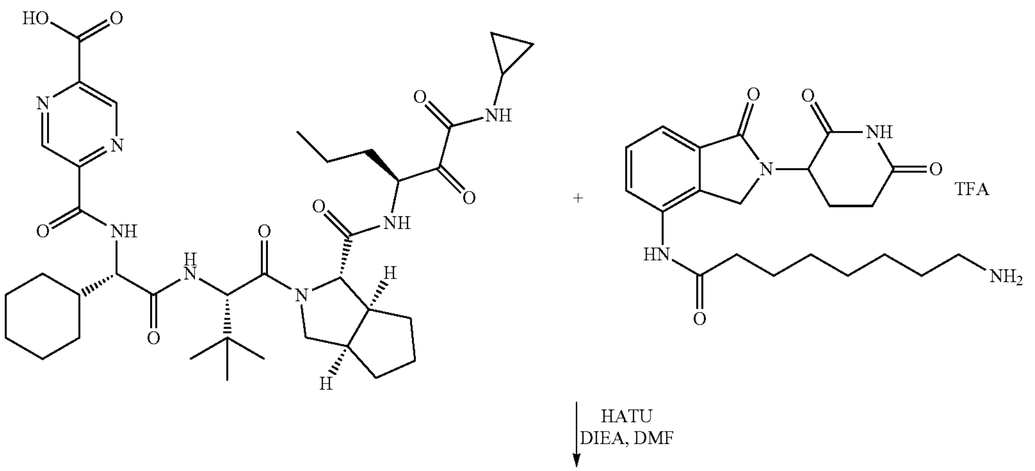

-continued

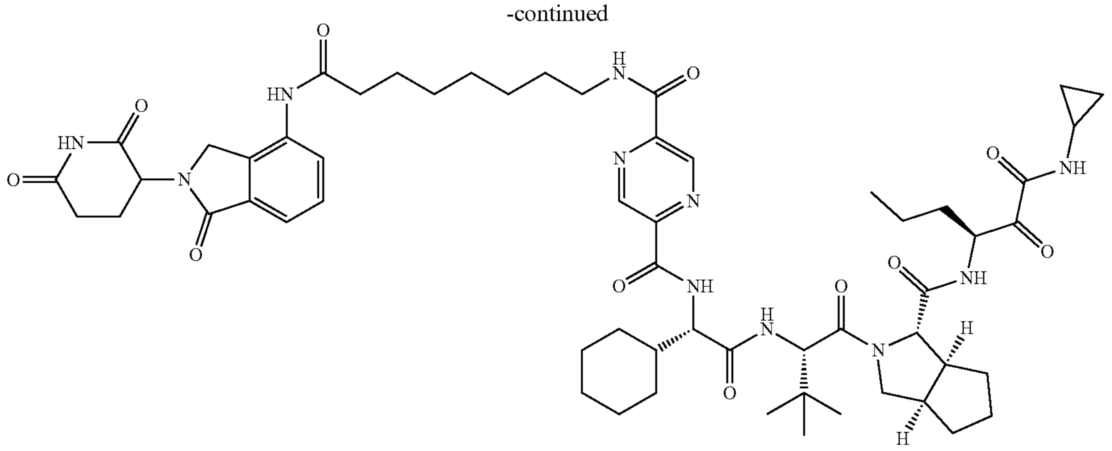

(4)

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl) pyrazine-2-carboxylic acid (43.3 mg, 0.060 mmol) and 4-(2-(2-(2-aminoethoxy)ethoxy)ethylamino)-2-(1-methyl-2,6-dioxopiperidin-3-yl)isoindoline-1,3-dione TFA salt (29.8 mg, 0.060 mmol) in DMF (1 mL), DIEA (38.8 mg, 0.30 mmol) and HATU (45.6 mg, 0.12 mmol) were added at 0° C. The reaction was stirred for 10 minutes. The reaction mixture was purified with HPLC to get compound 4 (23 mg, 0.021 mmol, 35% yield).

LC/MS m/z calculated for $[M+H]^+$ 1106.6, found 1106.6.

Example 5: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(8-(2-(2-(2,6-dioxopiperidin-3-yl)-1,3-dioxoisoindolin-4-ylamino)acetamido)octyl)pyrazine-2,5-dicarboxamide (5)

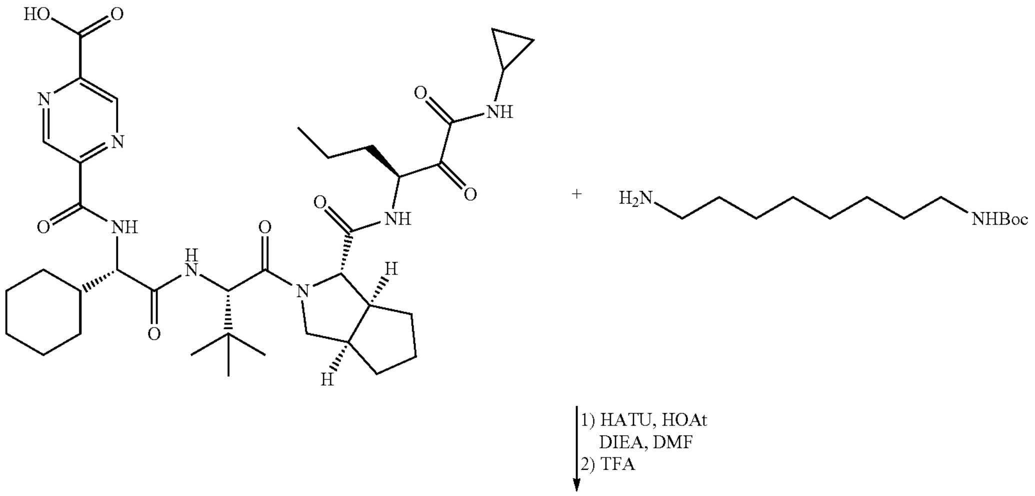

-continued

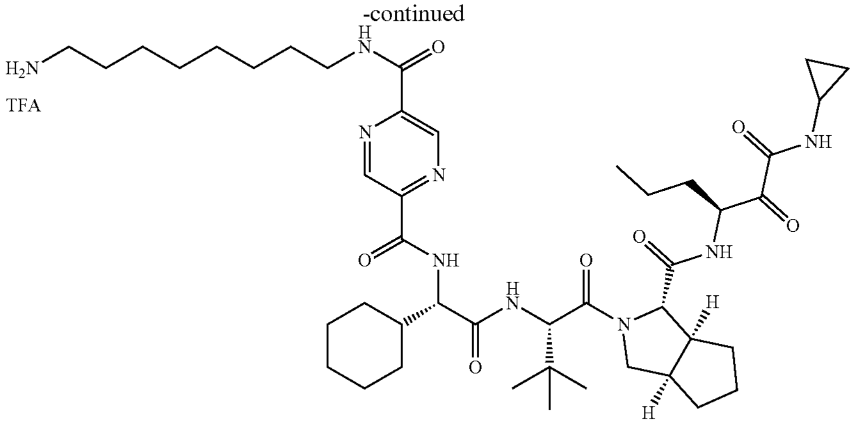

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (120 mg, 0.166 mmol) and tert-butyl 8-aminooctylcarbamate (40.6 mg, 0.166 mmol) in DMF (1 mL), DIEA (107 mg, 0.83 mmol), HATU (126 mg, 0.332 mmol) and HOAt (4.5 mg, 0.0332 mmol) were added at 0° C. The reaction was stirred for 10 minutes. The reaction mixture was purified with HPLC to get tert-butyl 8-(5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxamido)octylcarbamate. The residue was dissolved in DCM (1 mL), and then TFA (1 mL) was added to the solution. The mixture was stirred at room temperature for 1 hour. The solvent was evaporated under vacuum to get the crude product N2-(8-aminooctyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (141 mg, 0.15 mmol, 90%) without any further purification.

LC/MS m/z calculated for $[M+H]^+$ 850.5, found 850.5.

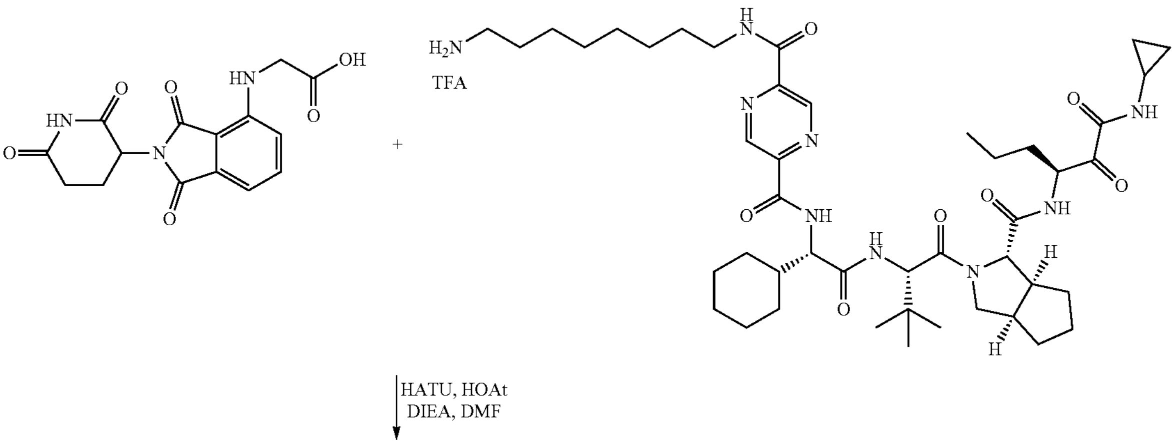

-continued

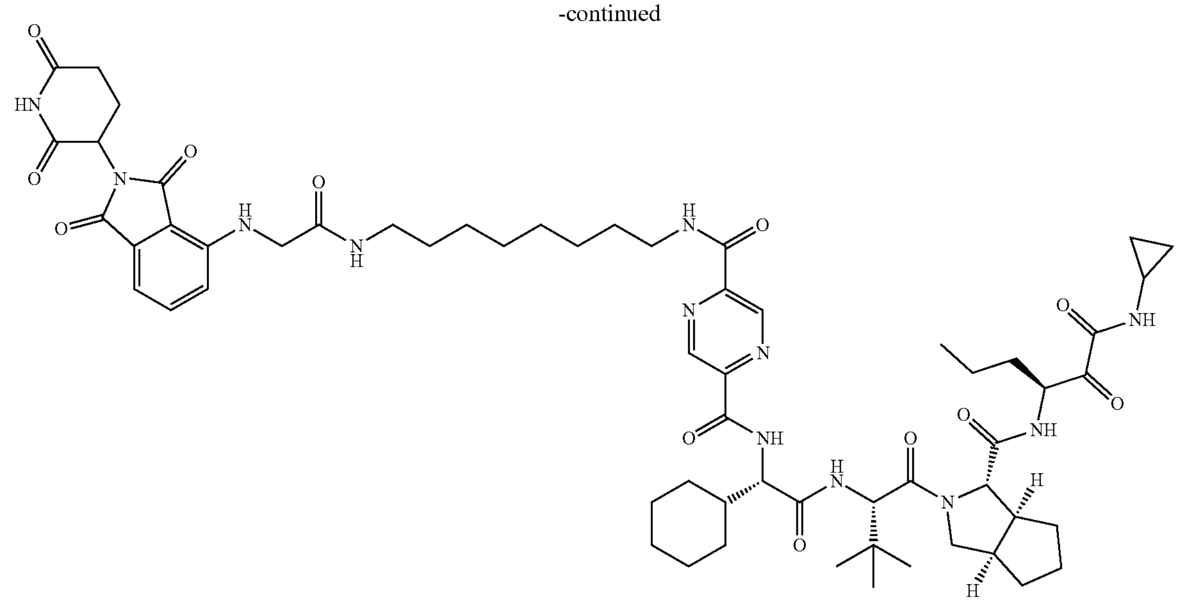

(5)

To a solution of N2-(8-aminooctyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.052 mmol) and 2-(2-(2,6-dioxopiperidin-3-yl)-1,3-dioxoisoindolin-4-ylamino)acetic acid (17.2 mg, 0.052 mmol) in DMF (1 mL), DIEA (33.6 mg, 0.26 mmol), HATU (39.5 mg, 0.104 mmol) and HOAт (1.4 mg, 0.0104 mmol) were added at 0° C. The reaction was stirred for 10 minutes. The reaction mixture was purified with HPLC to get compound 5 (46 mg, 0.040 mmol, 77% yield).

LC/MS m/z calculated for $[M+H]^+$ 1163.6, found 1163.6.

Example 6: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(8-(3-(2-(2-(2-(2,6-dioxopiperidin-3-yl)-1,3-dioxoisoindolin-4-ylamino)ethoxy)ethoxy)propanamido)octyl)pyrazine-2,5-dicarboxamide (6)

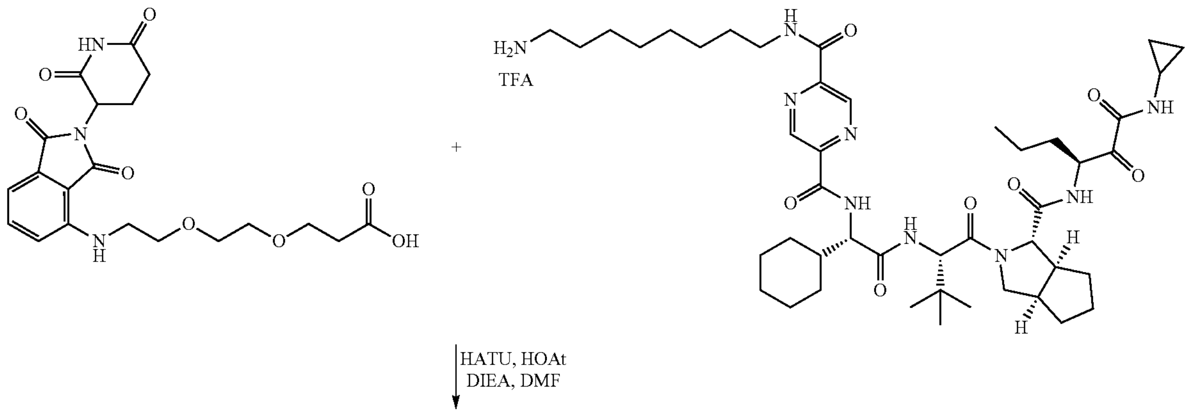

-continued

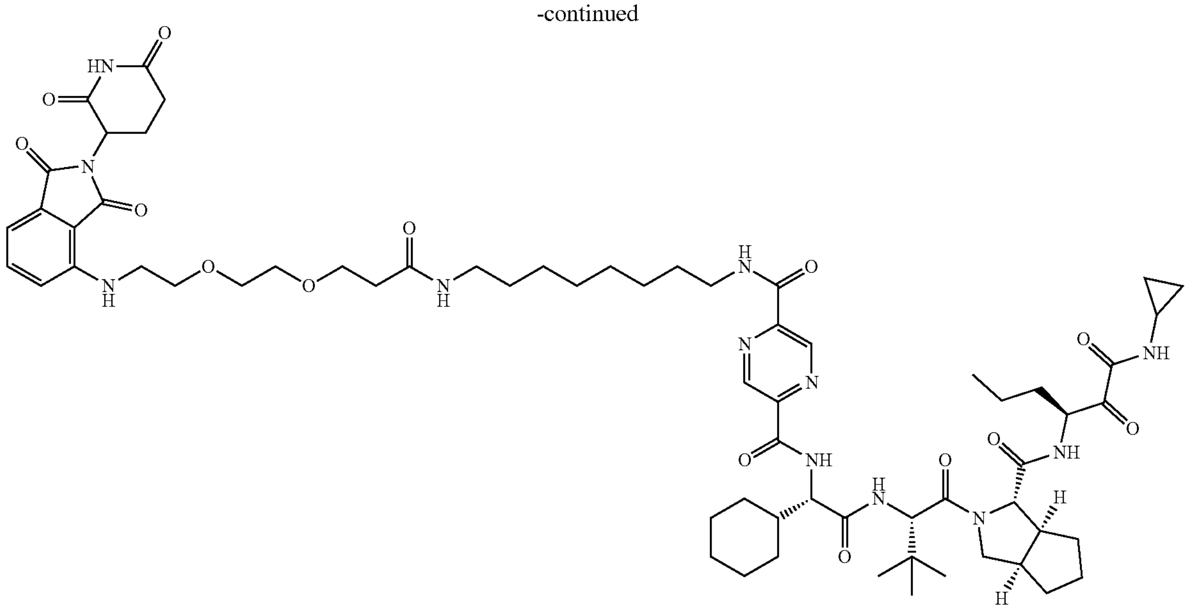

(6)

To a solution of N2-(8-aminooctyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.052 mmol) and 3-(2-(2-(2-(2,6-dioxopiperidin-3-yl)-1,3-dioxoisoindolin-4-ylamino)ethoxy)ethoxy)propanoic acid (22 mg, 0.052 mmol) in DMF (1 mL), DIEA (33.6 mg, 0.26 mmol), HATU (39.5 mg, 0.104 mmol) and HOAT (1.4 mg, 0.0104 mmol) were added at 0° C. The mixture was stirred for 10 minutes. The reaction mixture was purified with HPLC to get compound 6 (40 mg, 0.032 mmol, 61% yield). LC/MS m/z calculated for $[M+H]^+$ 1265.7, found 1265.7.

Example 7: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(1-(2-(2,6-dioxopiperidin-3-yl)-1-oxoisoindolin-4-ylamino)-15-oxo-3,6,9,12-tetraoxa-16-azatetracosan-24-yl)pyrazine-2,5-dicarboxamide (7)

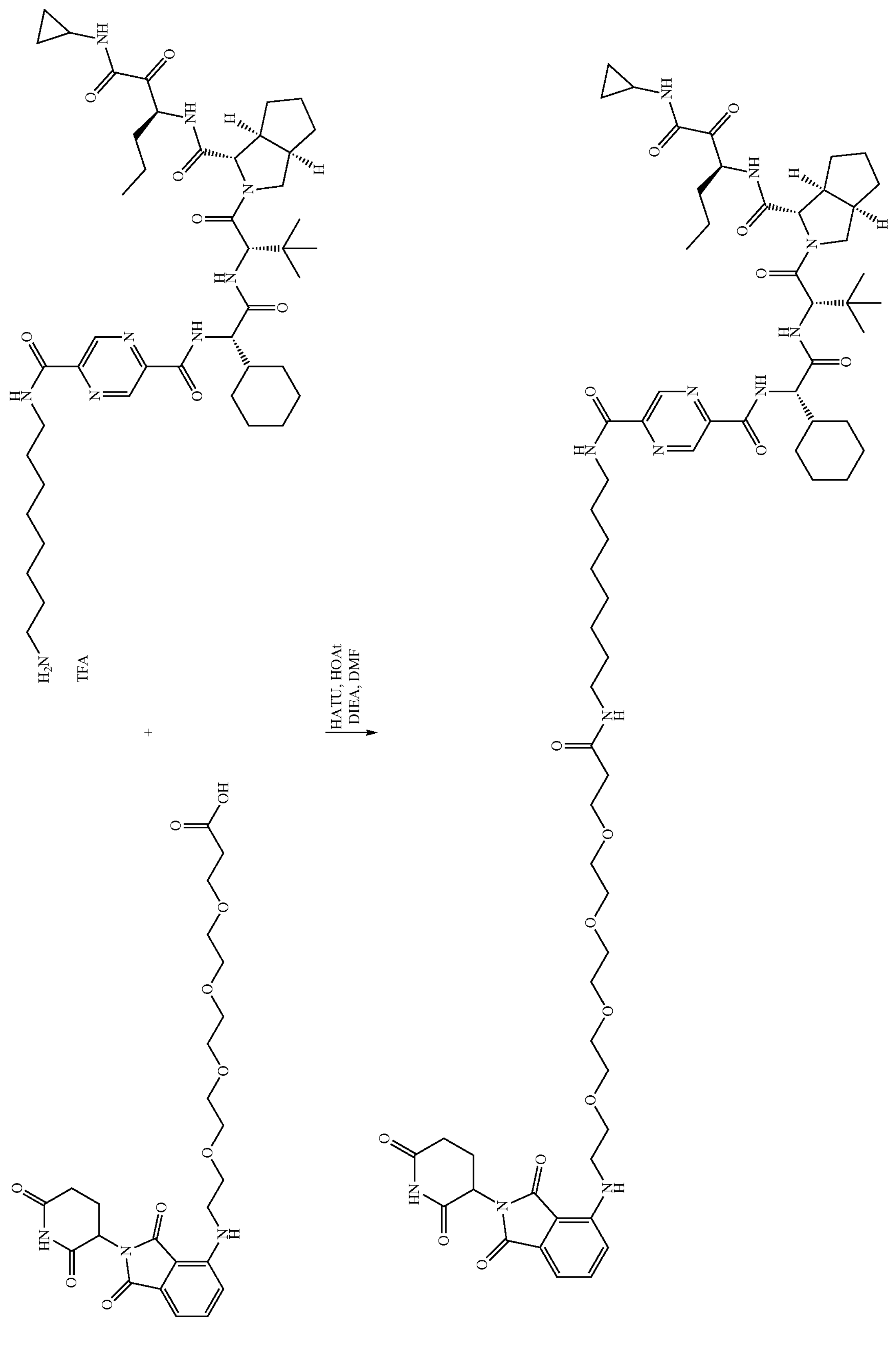
(7)

To a solution of N2-(8-aminooctyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.052 mmol) and Len-PEG4-acid (26.4 mg, 0.052 mmol) in DMF (1 mL), DIEA (33.6 mg, 0.26 mmol), HATU (39.5 mg, 0.104 mmol) and HOAτ (1.4 mg, 0.0104 mmol) were at 0° C. The reaction was stirred for 10 minutes. The reaction mixture was purified with HPLC to get compound 7 (37 mg, 0.0276 mmol, 53% yield).

LC/MS m/z calculated for $[M+H]^+$ 1339.8, found 1339.8.

Example 8: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(2-(2,6-dioxopiperidin-3-yl)-1,3-dioxoisoindolin-4-ylamino)acetamido)ethoxy)ethoxy)ethyl)pyrazine-2,5-dicarboxamide (8)

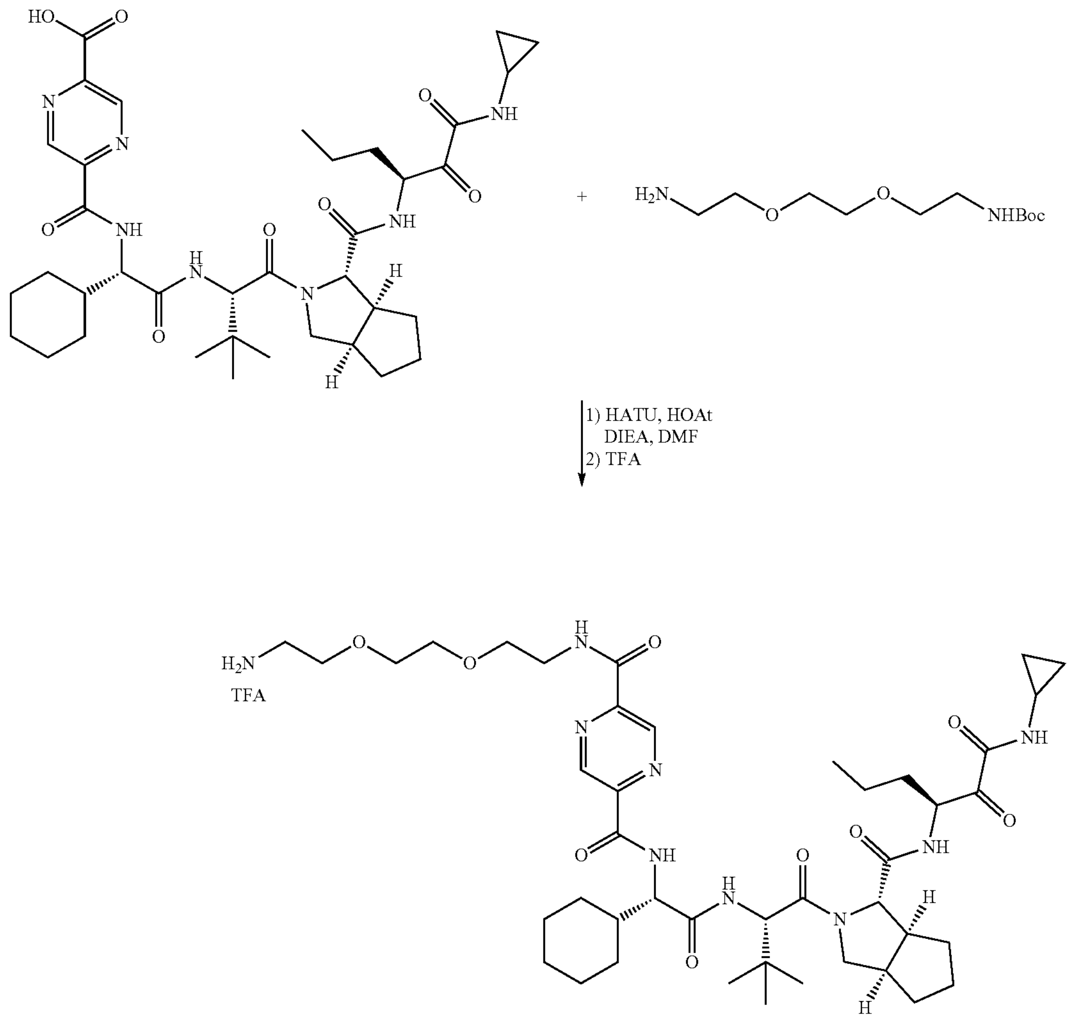

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (210 mg, 0.29 mmol) and tert-butyl 2-(2-(2-aminoethoxy)ethoxy)ethylcarbamate (72 mg, 0.29 mmol) in DMF (2 mL), DIEA (187 mg, 1.45 mmol), HATU (220 mg, 0.58 mmol) and HOAτ (7.9 mg, 0.058 mmol) were added at 0° C. The reaction was stirred for 10 minutes. The reaction mixture was purified with HPLC to get tert-butyl 2-(2-(2-(5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxamido)ethoxy)ethoxy)ethylcarbamate. The residue was dissolved in DCM (2 mL), and then TFA (2 mL) was added to the solution. The reaction was stirred at room temperature for 1 hour. The solvent was evaporated under vacuum to get N2-(2-(2-(2-aminoethoxy)ethoxy)ethyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (246 mg, 0.255 mmol, 88% yield) without any further purification.

LC/MS m/z calculated for $[M+H]^+$ 854.5, found 854.5.

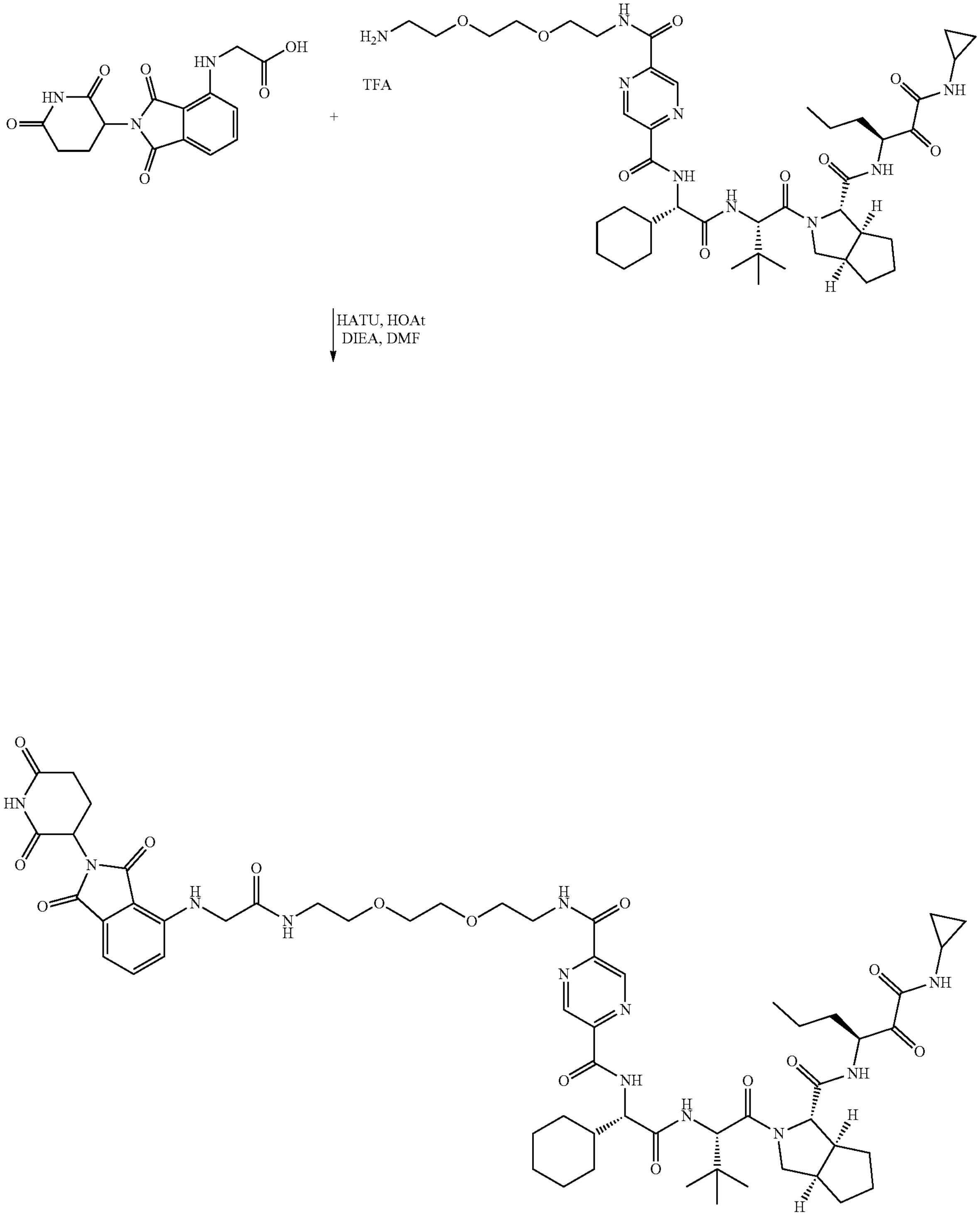

(8)

To a solution of N2-(2-(2-(2-aminoethoxy)ethoxy)ethyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.059 mmol) and 2-(2-(2,6-dioxopiperidin-3-yl)-1,3-dioxoisoindolin-4-ylamino)acetic acid (19.4 mg, 0.059 mmol) in DMF (1 mL), DIEA (38 mg, 0.295 mmol), HATU (45 mg, 0.118 mmol) and HOAτ (1.6 mg, 0.0118 mmol) were added at 0° C. The reaction was stirred for 10 minutes. The reaction mixture was purified with HPLC to get compound 8 (27 mg, 0.023 mmol, 39% yield).

LC/MS m/z calculated for $[M+H]^+$ 1167.6, found 1167.6.

Example 9: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(18-(2-(2,6-dioxopiperidin-3-yl)-1,3-dioxoisoindolin-4-ylamino)-10-oxo-3,6,13,16-tetraoxa-9-azaoctadecyl)pyrazine-2,5-dicarboxamide (9)

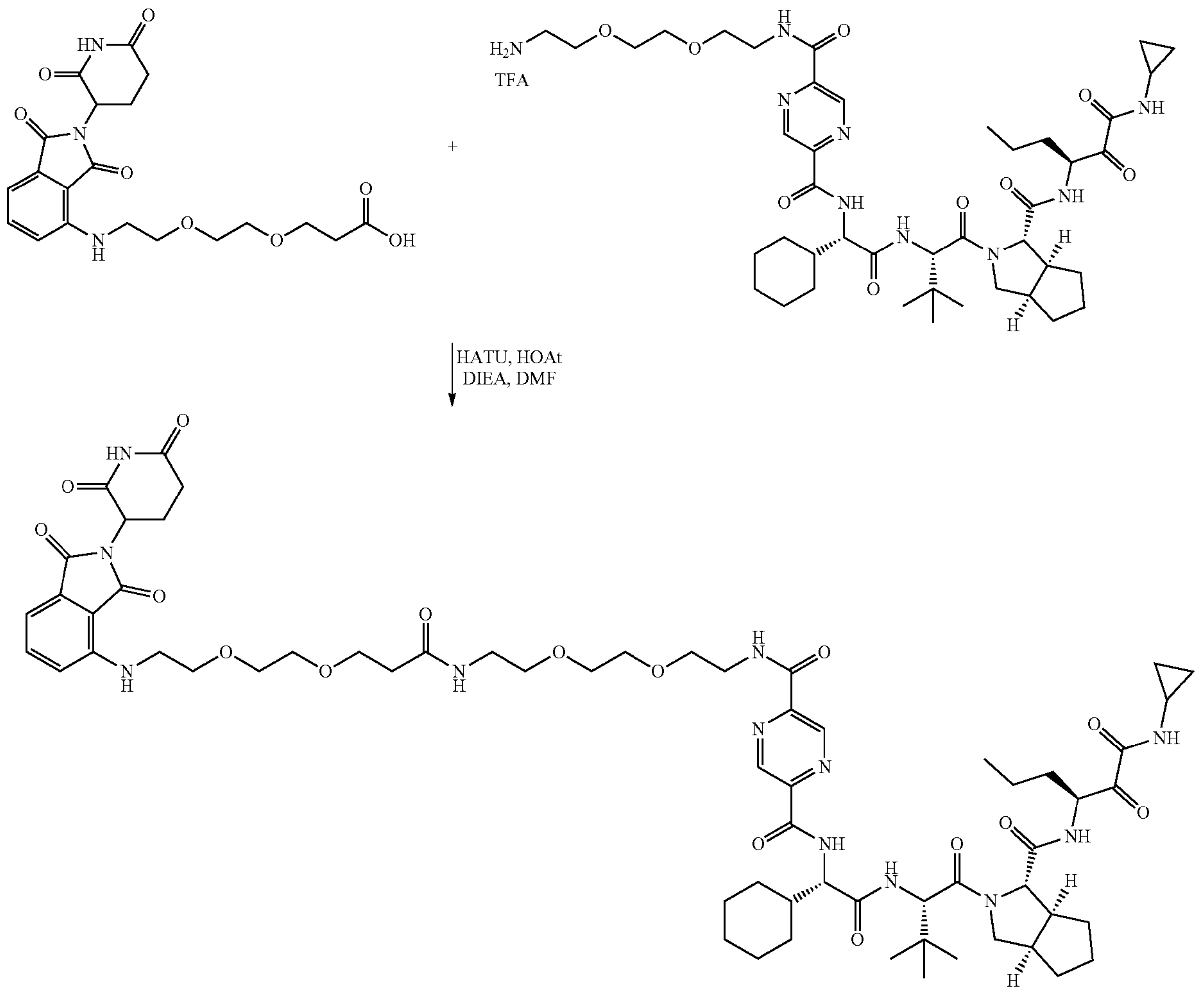

(9)

To a solution of N2-(2-(2-(2-aminoethoxy)ethoxy)ethyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.059 mmol) and 3-(2-(2-(2-(2,6-dioxopiperidin-3-yl)-1,3-dioxoisoindolin-4-ylamino)ethoxy)ethoxy)propanoic acid (25.5 mg, 0.059 mmol) in DMF (1 mL), DIEA (38 mg, 0.295 mmol), HATU (45 mg, 0.118 mmol) and HOAτ (1.6 mg, 0.0118 mmol) were added at 0° C. The reaction was stirred for 10 minutes. The reaction mixture was purified with HPLC to get compound 9 (33 mg, 0.026 mmol, 44% yield).

LC/MS m/z calculated for $[M+H]^+$ 1269.6, found 1269.6.

Example 10: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(1-(2-(2,6-dioxopiperidin-3-yl)-1-oxoisoindolin-4-ylamino)-15-oxo-3,6,9,12,19,22-hexaoxa-16-azatetracosan-24-yl)pyrazine-2,5-dicarboxamide (10)

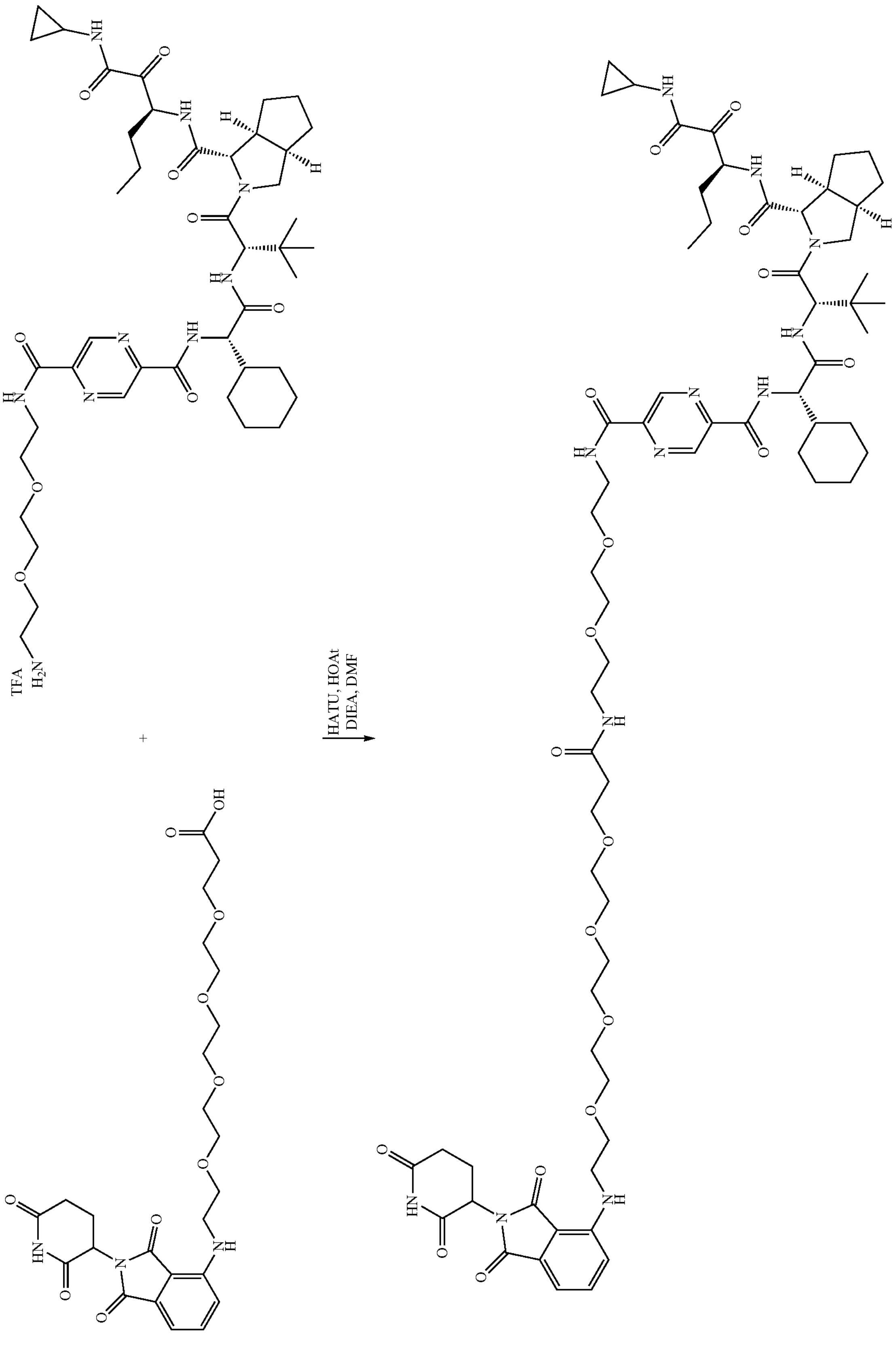
(10)

To a solution of N2-(2-(2-(2-aminoethoxy)ethoxy)ethyl)-N5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)pyrazine-2,5-dicarboxamide TFA salt (50 mg, 0.059 mmol) and Len-PEG4-acid (30 mg, 0.059 mmol) in DMF (1 mL), DIEA (38 mg, 0.295 mmol), HATU (45 mg, 0.118 mmol) and HOAt (1.6 mg, 0.0118 mmol) were added at 0° C. The mixture was stirred for 10 minutes. The reaction mixture was purified with HPLC to get compound 10 (33 mg, 0.026 mmol, 44% yield).

LC/MS m/z calculated for $[M+H]^+$ 1343.7, found 1343.7.

Example 11: Synthesis of N2-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(2,6-dioxopiperidin-3-yl)-1,3-dioxoisoindolin-4-ylamino)ethoxy)ethoxy)ethyl)pyrazine-2,5-dicarboxamide (11)

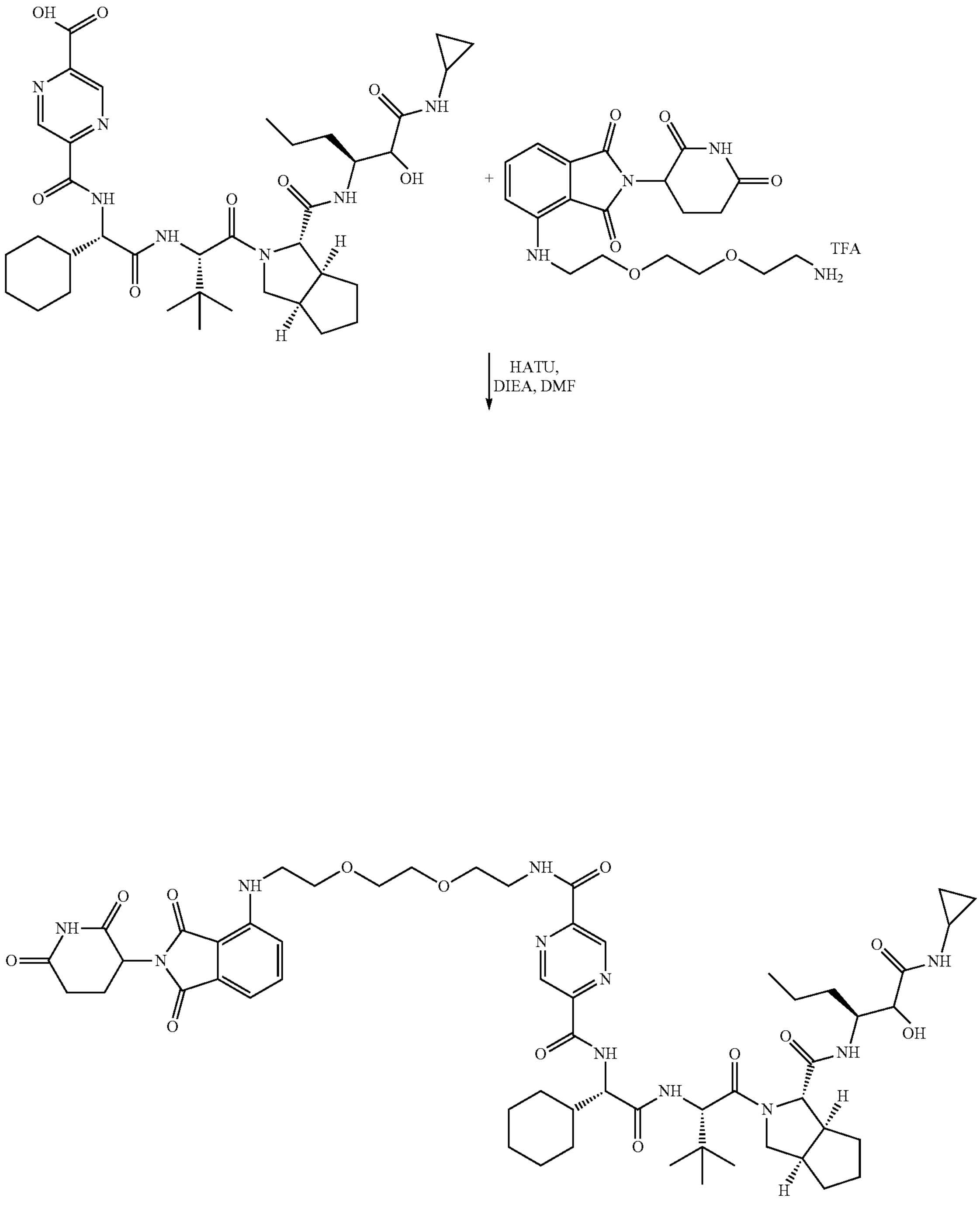

(11)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (21 mg, 0.029 mmol) and 4-(2-(2-(2-aminoethoxy)ethoxy)ethylamino)-2-(2,6-dioxopiperidin-3-yl)isoindoline-1,3-dione TFA salt (15 mg, 0.029 mmol) in DMF (1 mL), DIEA (19 mg, 0.145 mmol) and HATU (22 mg, 0.058 mmol) were added at 0° C. The mixture was stirred for 10 minutes. The reaction mixture was purified with HPLC to get compound 11 (12 mg, 0.0107 mmol, 38% yield).

LC/MS m/z calculated for $[M+H]^+$ 1112.6, found 1112.6.

Example 12: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(5-(2-(2,6-dioxopiperidin-3-yl)-1,3-dioxo-2,3-dihydro-1H-benzo[de]isoquinolin-5-yloxy)pentyl)pyrazine-2,5-dicarboxamide (12)

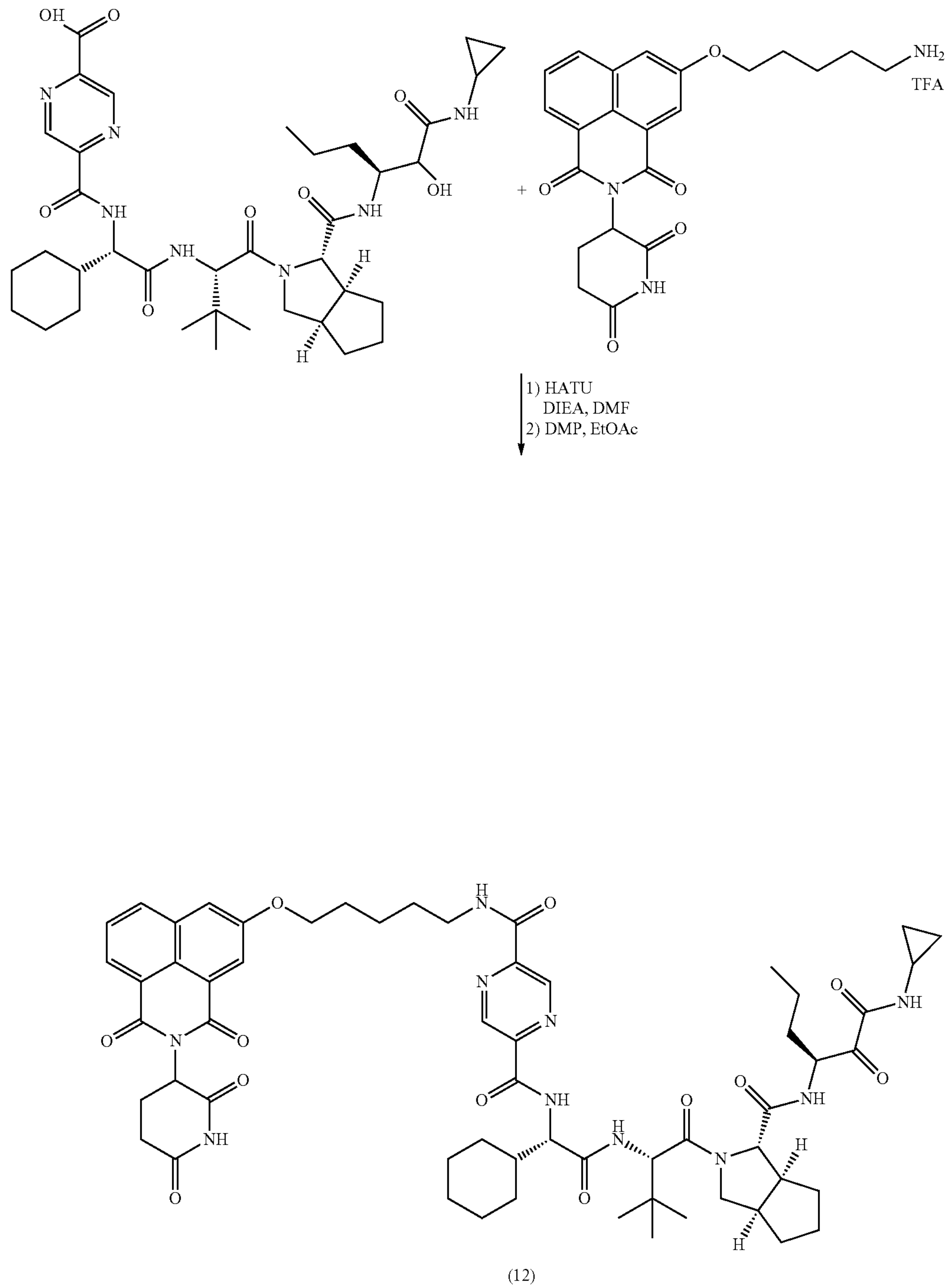

(12)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.028 mmol) and 5-(5-aminopentyloxy)-2-(2,6-dioxopiperidin-3-yl)-1H-benzo[de]isoquinoline-1,3(2H)-dioneTFA salt (15 mg, 0.028 mmol) in DMF (1 mL), DIEA (18 mg, 0.14 mmol) and HATU (21 mg, 0.056 mmol) were added at 0° C. The reaction was stirred for 10 minutes. The solvent was evaporated under vacuum to get crude product without any further purification. The residue was dissolved in ethyl acetate (1 mL). DMP (24 mg, 0.056 mmol) was added to the mixture at 0° C. The reaction was stirred for 6 hours. After Celite® filtration and evaporation of the solvent, the crude product was purified with HPLC to get compound 12 (7.1 mg, 0.0064 mmol, 23% yield in two steps).

LC/MS m/z calculated for $[M+H]^+$ 1115.5, found 1115.5.

Example 13: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(2,6-dioxopiperidin-3-yl)-1,3-dioxo-2,3-dihydro-1H-benzo[de]isoquinolin-5-yloxy)ethoxy)ethoxy)ethyl)pyrazine-2,5-dicarboxamide (13)

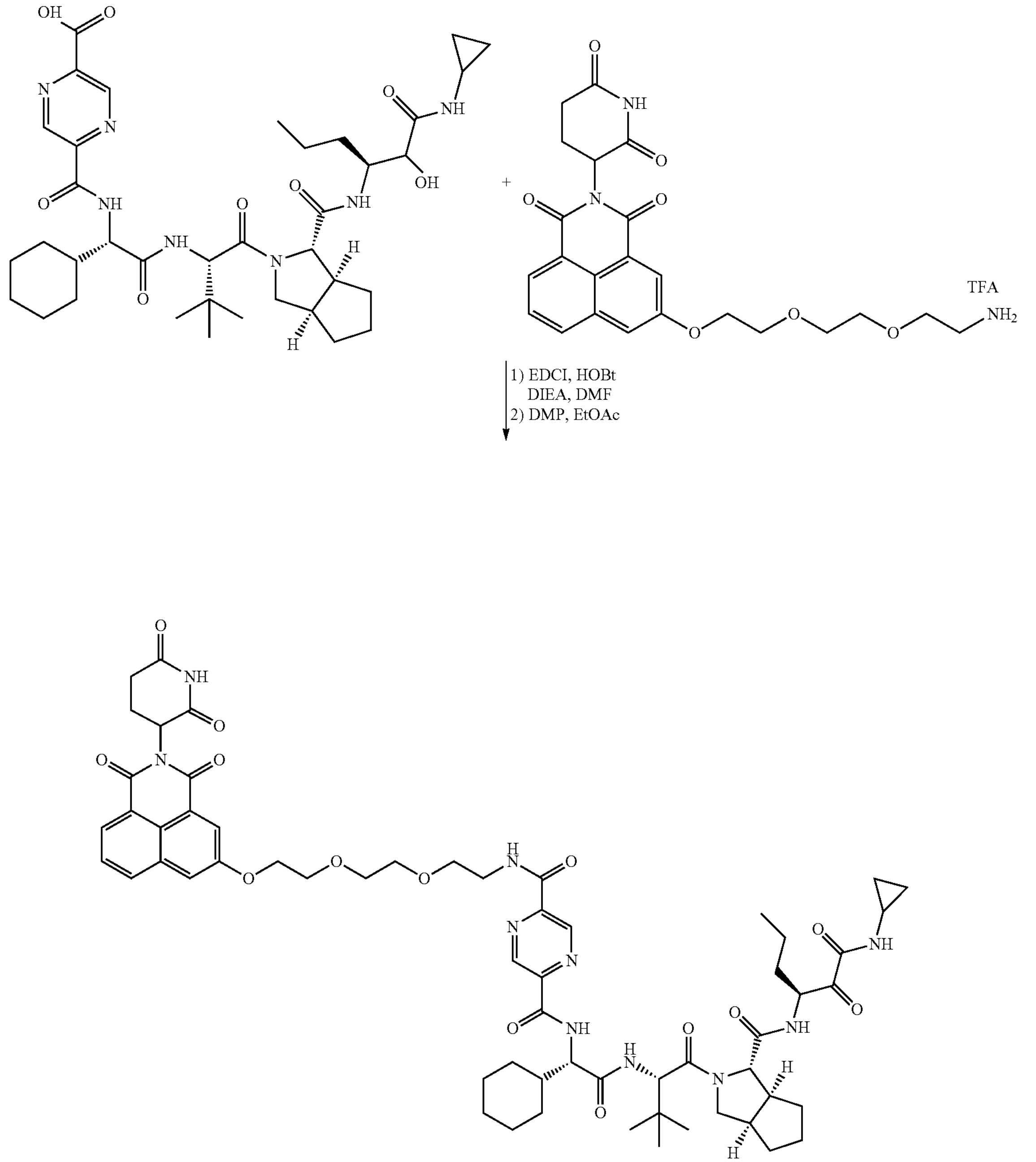

(13)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (29 mg, 0.039 mmol) and 5-(5-aminopentyloxy)-2-(2,6-dioxopiperidin-3-yl)-1H-benzo[de]isoquinoline-1,3(2H)-dioneTFA salt (18 mg, 0.039 mmol) in DMF (1 mL), DIEA (25 mg, 0.195 mmol), EDCI (15 mg, 0.078 mmol) and HOBt (11 mg, 0.078 mmol) were added at 0° C. The reaction was stirred for overnight. The solvent was evaporated under vacuum to get crude product without any further purification. The residue was dissolved in ethyl acetate (1 mL). DMP (29 mg, 0.069 mmol) was added to the mixture at 0° C. The reaction was stirred for 6 hours. After Celite® filtration and evaporation of the solvent, the crude product was purified with HPLC to get compound 13 (3.6 mg, 0.0031 mmol, 8% yield in two steps).

LC/MS m/z calculated for $[M+H]^+$ 1161.5, found 1161.5.

Example 14: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(6-(2,6-dioxopiperidin-3-ylcarbamoyl)pyridin-2-ylamino)ethoxy)ethoxy)ethyl)pyrazine-2,5-dicarboxamide (14)

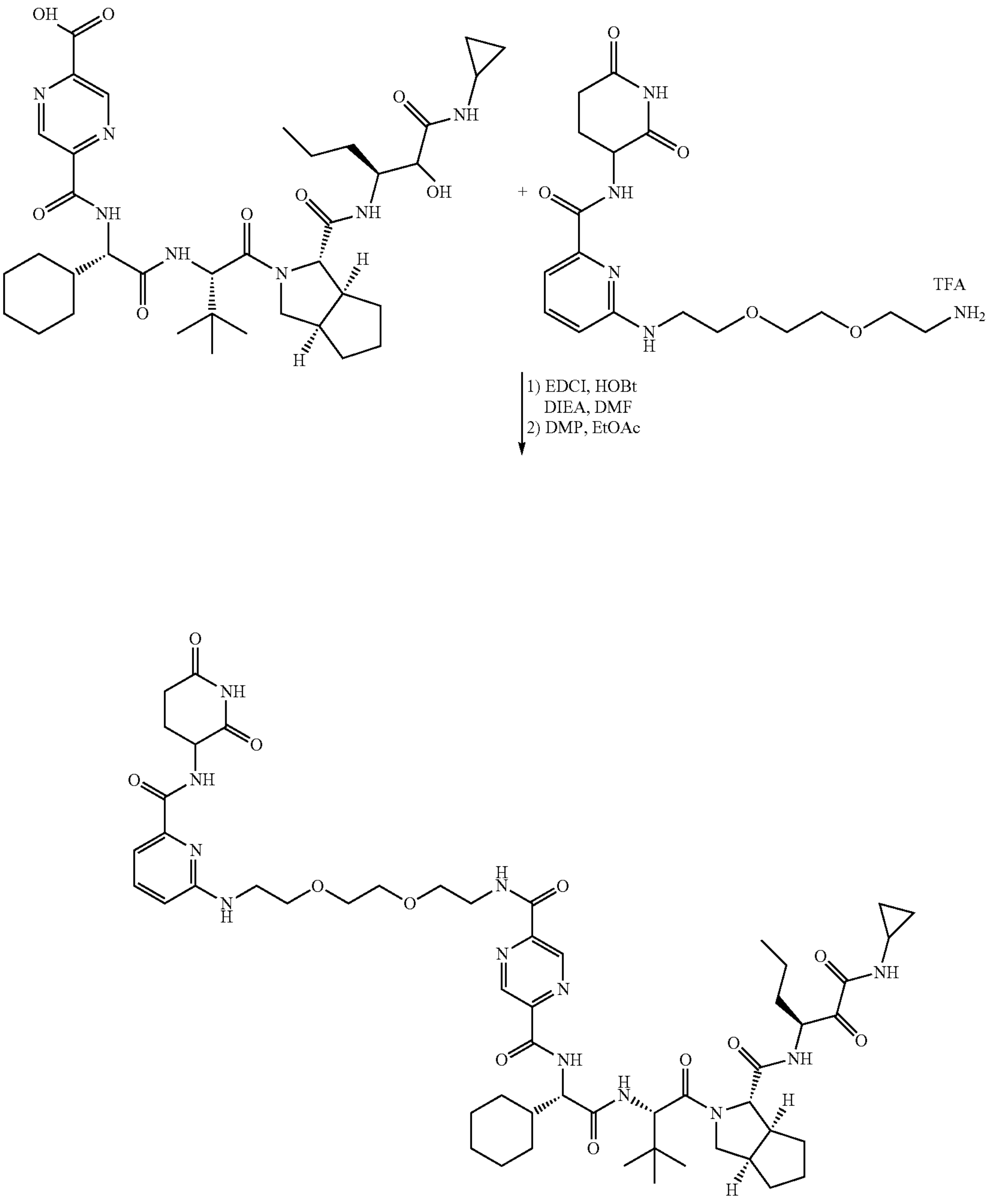

(14)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (40 mg, 0.055 mmol) and 6-(2-(2-(2-aminoethoxy)ethoxy)ethylamino)-N-(2,6-dioxopiperidin-3-yl)picolinamide TFA salt (21 mg, 0.055 mmol) in DMF (1 mL), DIEA (28 mg, 0.195 mmol), EDCI (21 mg, 0.11 mmol) and HOBt (15 mg, 0.11 mmol) were added at 0° C. The reaction was stirred overnight. The solvent was evaporated under vacuum to get crude product without any further purification. The residue was dissolved in ethyl acetate (1 mL). DMP (20 mg, 0.048 mmol) was added to the mixture at 0° C. The reaction was stirred for 6 hours. After Celite® filtration and evaporation of the solvent, the crude product was purified with HPLC to get compound 14 (23 mg, 0.021 mmol, 38% yield in two steps).

LC/MS m/z calculated for $[M+H]^+$ 1085.6, found 1085.6.

Example 15: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(3-((3-(2-(2,6-dioxopiperidin-3-yl)-1-oxoisoindolin-4-ylamino)propyl)(methyl)amino)propyl)pyrazine-2,5-dicarboxamide (15)

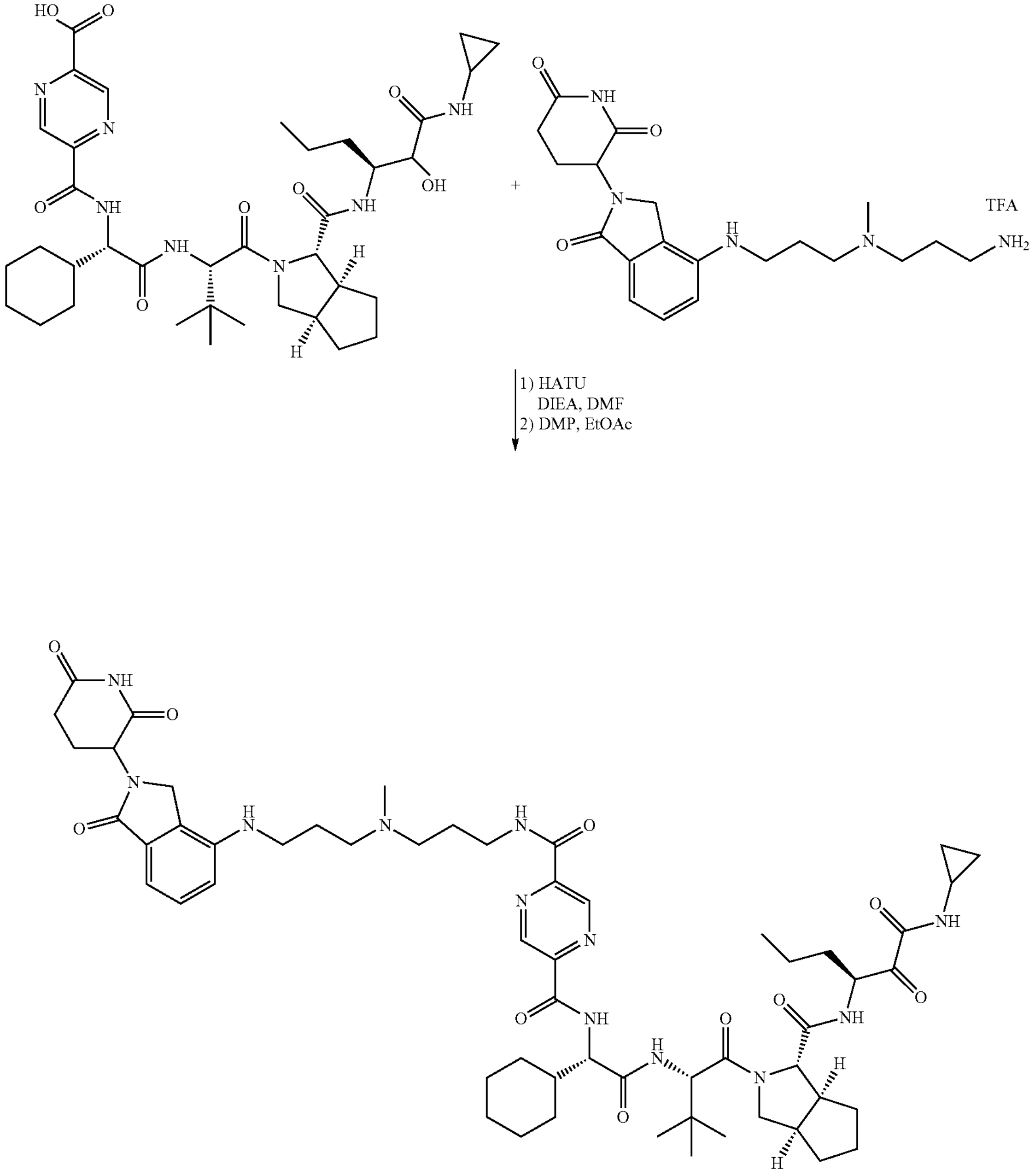

(15)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.027 mmol) and 3-(4-(3-((3-aminopropyl)(methyl)amino)propylamino)-1-oxoisoindolin-2-yl)piperidine-2,6-dione TFA salt (11.3 mg, 0.027 mmol) in DMF (1 mL), DIEA (18 mg, 0.138 mmol) and HATU (21 mg, 0.054 mmol) were added at 0° C. The reaction was stirred for 10 minutes. The solvent was evaporated under vacuum to get crude product without any further purification. The residue was dissolved in ethyl acetate (1 mL). DMP (32 mg, 0.076 mmol) was added to the mixture at 0° C. The reaction was stirred for 6 hours. After Celite® filtration and evaporation of the solvent, the crude product was purified with HPLC to get compound 15 (5.3 mg, 0.0048 mmol, 18% yield in two steps).

LC/MS m/z calculated for $[M+H]^+$ 1093.6, found 1093.6.

Example 16: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(12-(2-(2,6-dioxopiperidin-3-yl)-1,3-dioxoisoindolin-4-ylamino)dodecyl)pyrazine-2,5-dicarboxamide (16)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.027 mmol) and 4-(12-aminododecylamino)-2-(2,6-dioxopiperidin-3-yl)isoindoline-1,3-dione TFA salt (15 mg, 0.027 mmol) in DMF (1 mL), DIEA (18 mg, 0.138 mmol) and HATU (21 mg, 0.054 mmol) were added at 0° C. The reaction was stirred for 10 min. The solvent was evaporated under vacuum to get crude product without any further purification. The residue was dissolved in ethyl acetate (1 mL). DMP (32 mg, 0.076 mmol) was added to the mixture at 0° C. The reaction was stirred for 6 hours. After Celite® filtration and evaporation of the solvent, the crude product was purified with HPLC to get compound 16 (5.9 mg, 0.0051 mmol, 19% yield in two steps).

LC/MS m/z calculated for $[M+H]^+$ 1162.7, found 1162.7.

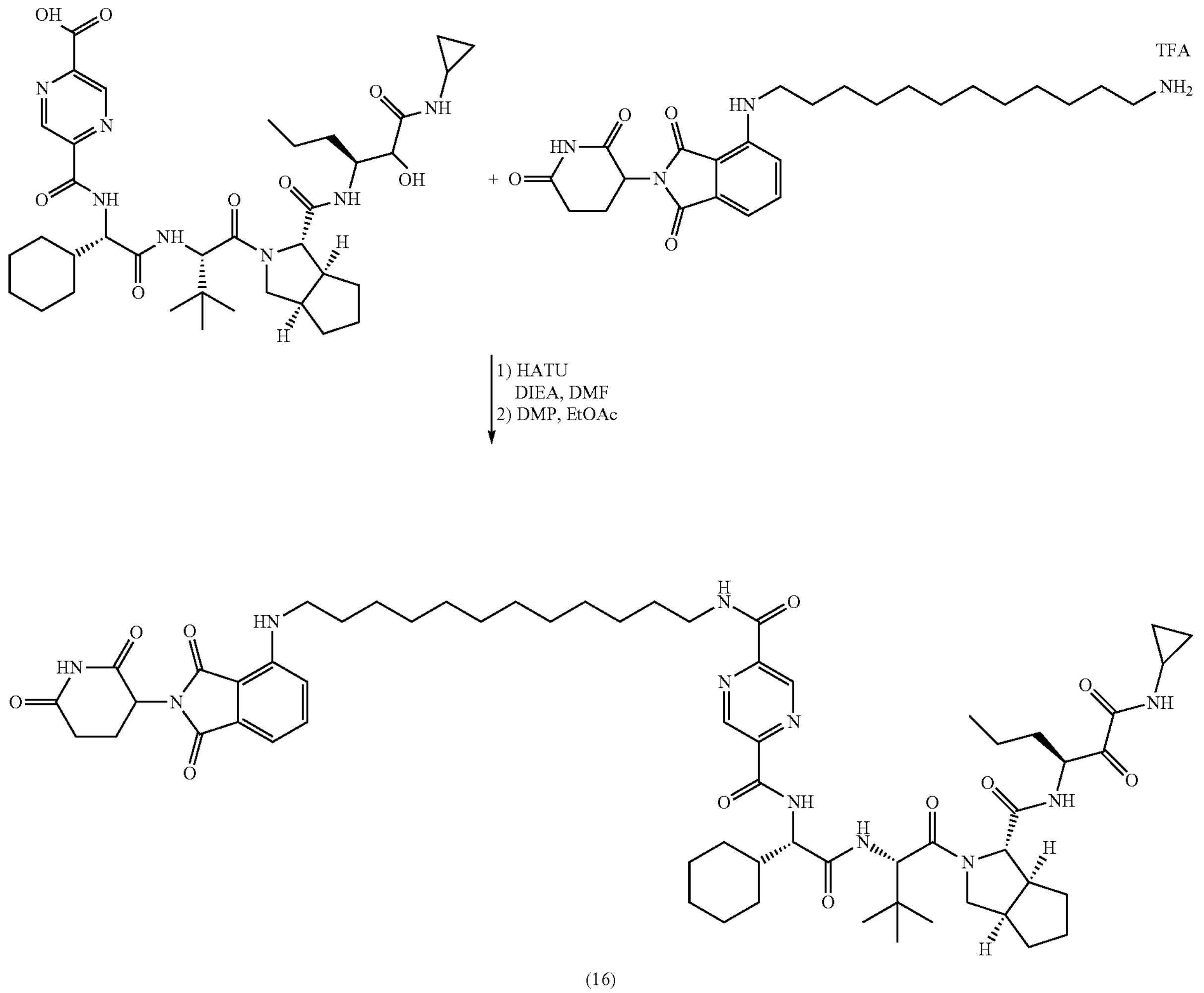

(16)

Example 17: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(3-(2-(2,6-dioxopiperidin-3-yl)-1,3-dioxo-2,3-dihydro-1H-benzo[de]isoquinolin-5-yloxy)propyl)pyrazine-2,5-dicarboxamide (17)
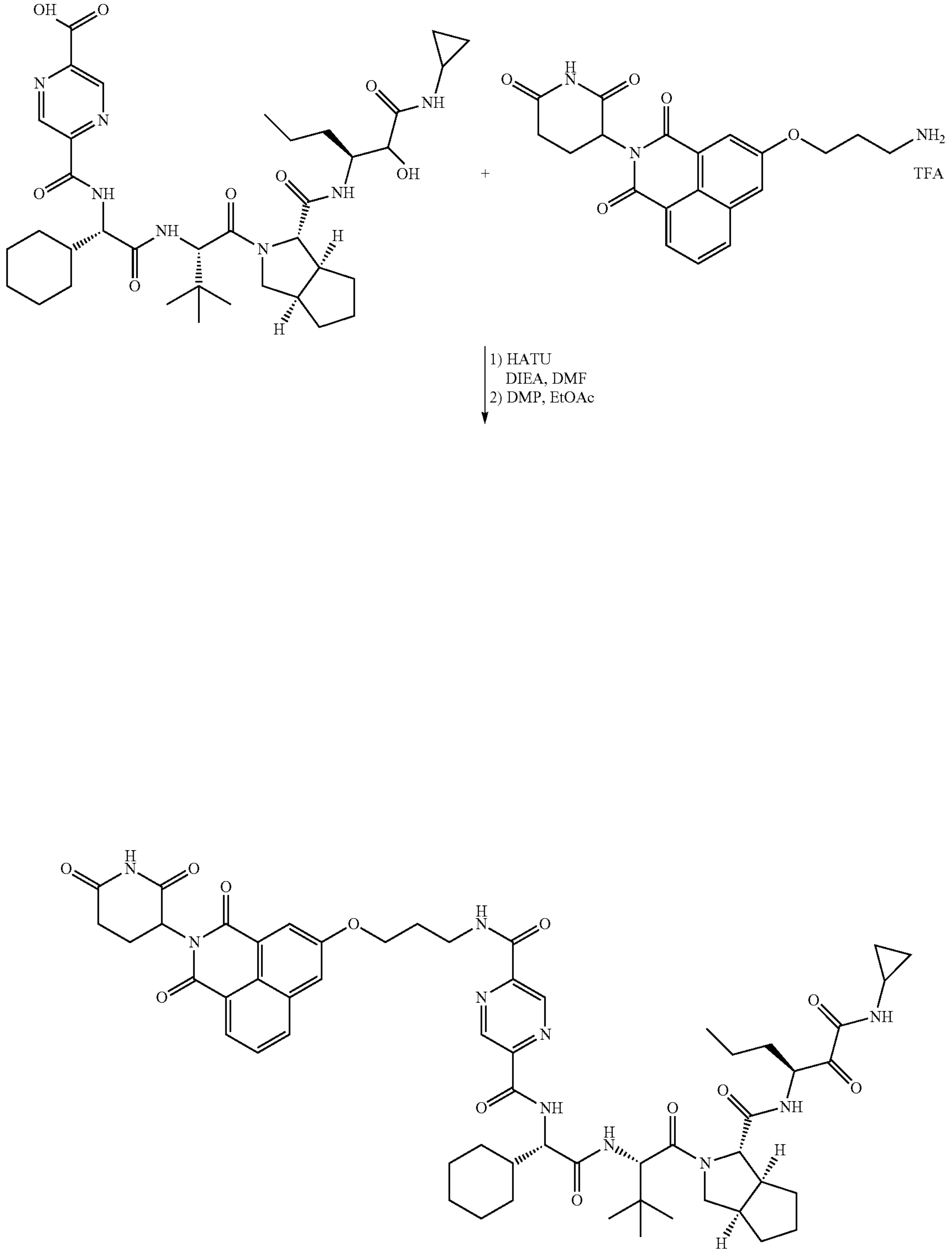
(17)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.027 mmol) and 5-(3-aminopropoxy)-2-(2,6-dioxopiperidin-3-yl)-1H-benzo[de]isoquinoline-1,3(2H)-dione TFA salt (10.5 mg, 0.027 mmol) in DMF (1 mL), DIEA (18 mg, 0.138 mmol) and HATU (21 mg, 0.054 mmol) were added at 0° C. The reaction was stirred for 10 min. The solvent was evaporated under vacuum to get crude product without any further purification. The residue was dissolved in ethyl acetate (1 mL). DMP (32 mg, 0.076 mmol) was added to the mixture at 0° C. The reaction was stirred for 6 hours. After Celite® filtration and evaporation of the solvent, the crude product was purified with HPLC to get compound 17 (4.8 mg, 0.0044 mmol, 16% yield in two steps).

LC/MS m/z calculated for $[M+H]^+$ 1087.5, found 1087.5.

Example 18: Synthesis of (1S,3aR,6aS)-2-((2S)-2-((2S)-2-cyclohexyl-2-(5-(2-(2-(2-(2-(2,6-dioxopiperidin-3-yl)-1-oxoisoindolin-4-ylamino)ethoxy)ethoxy)ethylamino)pyrazine-2-carboxamido)acetamido)-3,3-dimethylbutanol)-N-((3S)-1-(cyclopropylamino)-2-hydroxy-1-oxohexan-3-yl)octahydrocyclopenta[c]pyrrole-1-carboxamide (18)

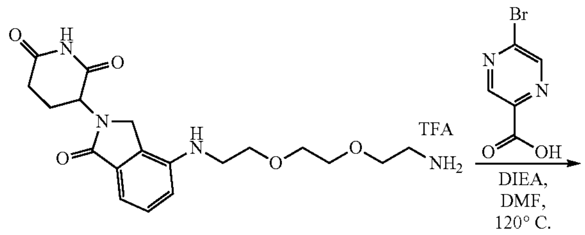

-continued

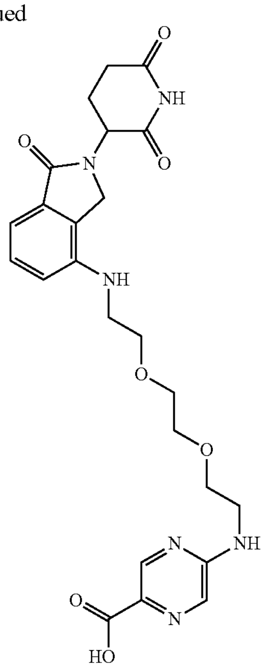

To a solution of 5-bromopyrazine-2-carboxylic acid (27 mg, 0.13 mmol) in DMF (1 mL), DIEA (167 mg, 1.30 mmol) and 3-(4-(2-(2-(2-aminoethoxy)ethoxy)ethylamino)-1-oxoisoindolin-2-yl)piperidine-2,6-dione (100 mg, 0.20 mmol) were added at room temperature. The mixture was heated up to 120° C. for 12 hours. The solvent was removed under vacuum to get crude product 5-(2-(2-(2-(2-(2,6-dioxopiperidin-3-yl)-1-oxoisoindolin-4-ylamino)ethoxy)ethoxy)ethylamino)pyrazine-2-carboxylic acid without any further purification.

LC/MS m/z calculated for $[M+H]^+$ 513.2, found 513.2.

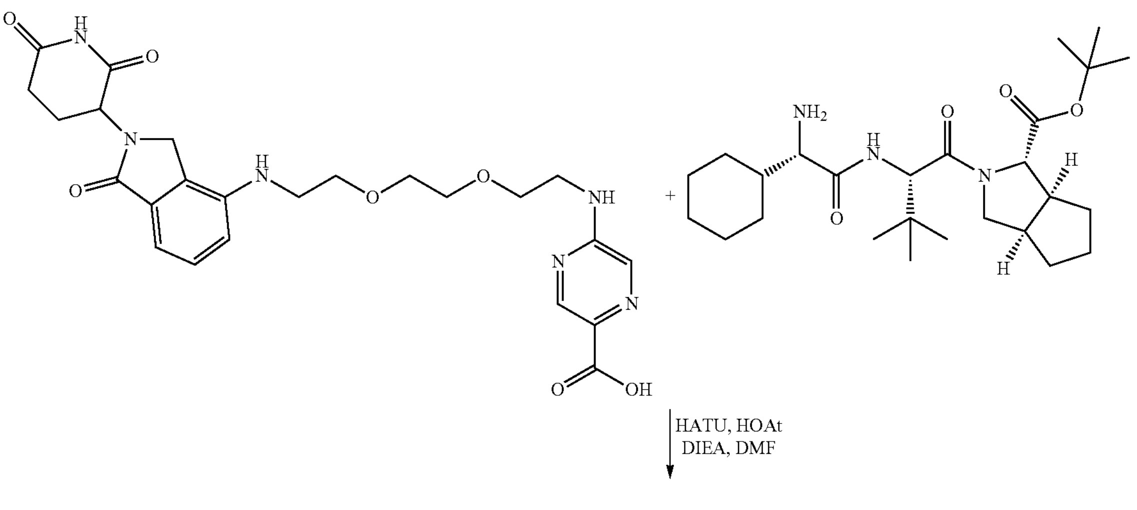

-continued

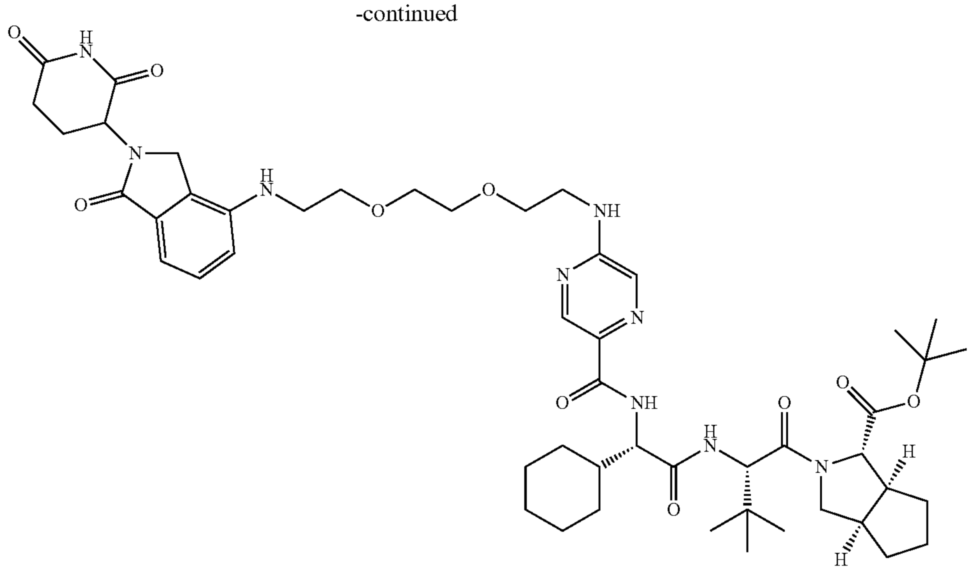

To a solution of 5-(2-(2-(2-(2-(2,6-dioxopiperidin-3-yl)-1-oxoisoindolin-4-ylamino)ethoxy)ethoxy)ethylamino) pyrazine-2-carboxylic acid (66 mg, 0.13 mmol) and (1 S,3 aR,6aS)-tert-butyl 2-((S)-2-((S)-2-amino-2-cyclohexylacetamido)-3,3-dimethylbutanoyl)octahydrocyclopenta[c]pyrrole-1-carboxylate (60 mg, 0.13 mmol) in DMF (2 mL), DIEA (84 mg, 0.65 mmol), HATU (99 mg, 0.26 mmol) and HOAτ (3.5 mg, 0.026 mmol) were added under ice bath. The reaction was stirred for 10 minutes, and the crude product was purified with HPLC to get (1S,3aR,6aS)-tert-butyl 2-((2S)-2-((2S)-2-cyclohexyl-2-(5-(2-(2-(2-(2-(2,6-dioxopiperidin-3-yl)-1-oxoisoindolin-4-ylamino)ethoxy)ethoxy) ethylamino)pyrazine-2-carboxamido)acetamido)-3,3-dimethylbutanoyl)octahydrocyclopenta[c]pyrrole-1-carboxylate (10 mg, 0.010 mmol, 800 yield in two steps).

LC/MS m/z calculated for $[M+H]^+$ 958.5, found 958.5.

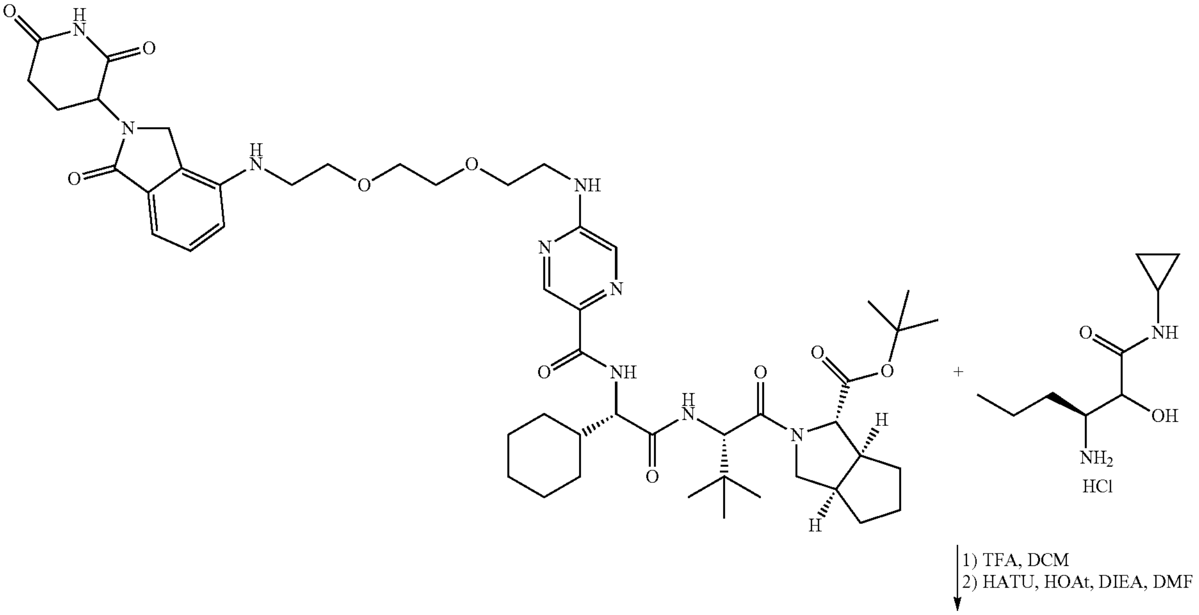

-continued

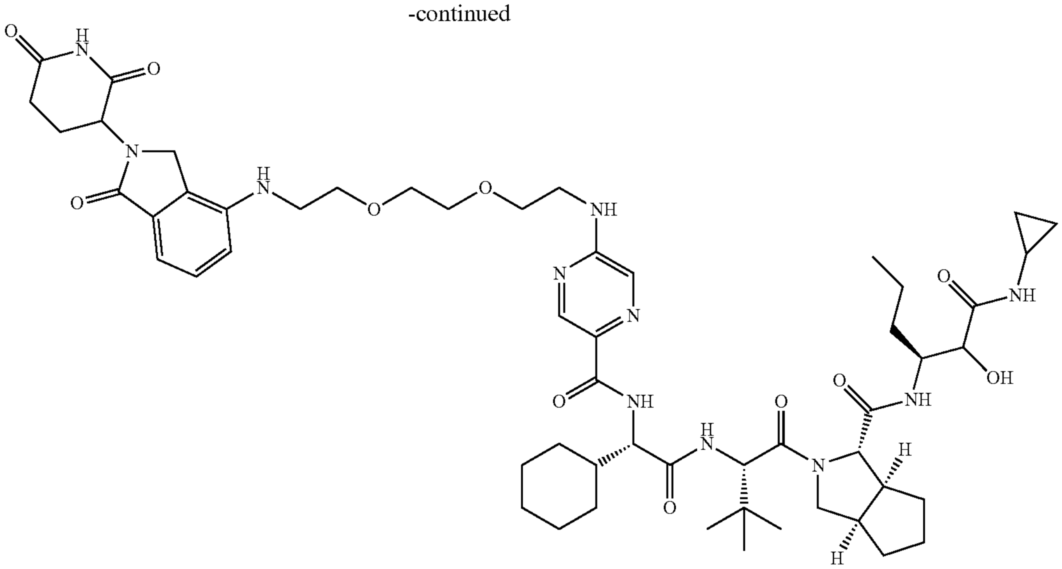

(18)

To a solution of (1S,3aR,6aS)-tert-butyl 2-((2S)-2-((2S)-2-cyclohexyl-2-(5-(2-(2-(2-(2-(2,6-dioxopiperidin-3-yl)-1-oxoisoindolin-4-ylamino)ethoxy)ethoxy)ethylamino)pyrazine-2-carboxamido)acetamido)-3,3-dimethylbutanoyl)octahydrocyclopenta[c]pyrrole-1-carboxylate (10 mg, 0.010 mmol) in DCM (1 mL), TFA (1 mL) was added at room temperature. The reaction was stirred for 1 hour. The solvent was removed under vacuum to obtain crude product without any further purification. To a solution of residue in DMF (1 mL), (3S)-3-amino-N-cyclopropyl-2-hydroxyhexanamide HCl salt (2.2 mg, 0.010 mmol), DIEA (7 mg, 0.050 mmol), HATU (7.6 mg, 0.020 mmol) and HOAt (0.3 mg, 0.0020 mmol) were added at 0° C. The mixture was stirred for 10 minutes. The reaction mixture was purified with HPLC to get compound 18 (3.3 mg, 0.040 mmol, 77% yield).

LC/MS m/z calculated for $[M+H]^+$ 1070.6, found 1070.6.

Example 19: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(1-methyl-2,6-dioxopiperidin-3-yl)-1,3-dioxoisoindolin-4-ylamino)ethoxy)ethoxy)ethyl)pyrazine-2,5-dicarboxamide (19)

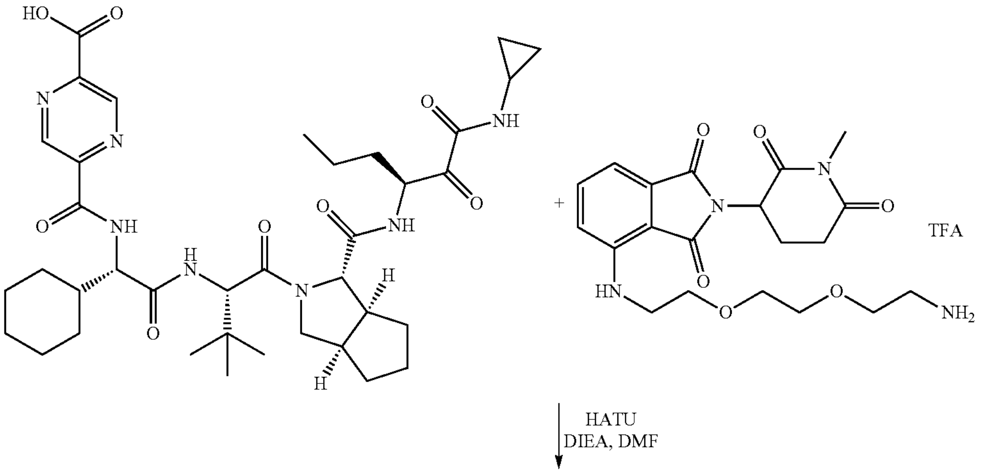

-continued

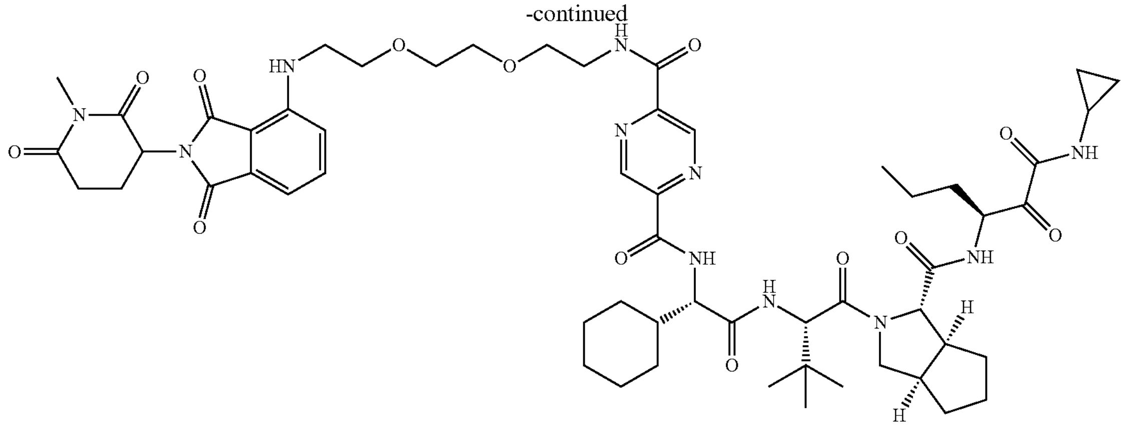

(19)

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (10 mg, 0.0138 mmol) and 4-(2-(2-(2-aminoethoxy)ethoxy)ethylamino)-2-(1-methyl-2,6-dioxopiperidin-3-yl)isoindoline-1,3-dione TFA salt (7 mg, 0.0138 mmol) in DMF (1 mL), DIEA (9 mg, 0.069 mmol) and HATU (10.5 mg, 0.0276 mmol) were added at 0° C. The mixture was stirred for 10 minutes. The reaction mixture was purified with HPLC to get compound 19 (9.8 mg, 0.0087 mmol, 63% yield).

LC/MS m/z calculated for $[M+H]^+$ 1124.6, found 1124.6.

Example 20: Synthesis of N2-((S)-1-cyclohexyl-2-((S)-1-((1S,3aR,6aS)-1-((S)-1-cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(1-methyl-2,6-dioxopiperidin-3-yl)-1,3-dioxoisoindolin-4-ylamino)ethoxy)ethoxy)ethyl)pyrazine-2,5-dicarboxamide (20)

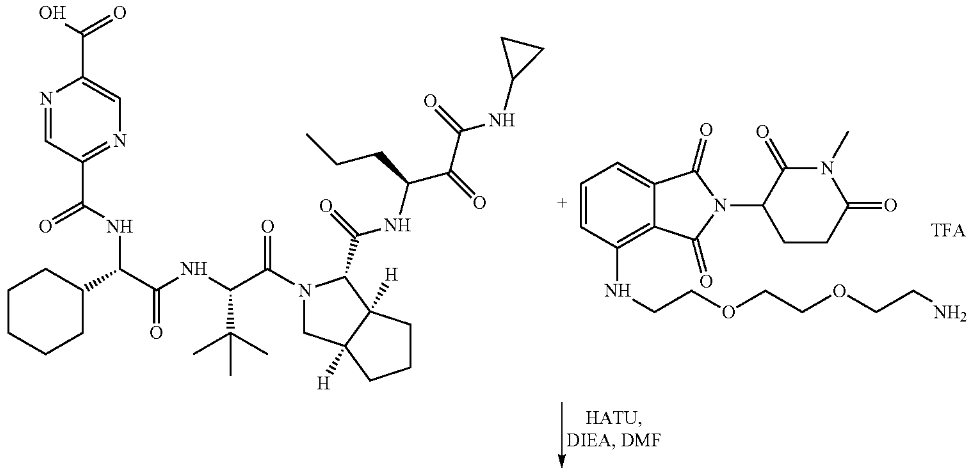

-continued

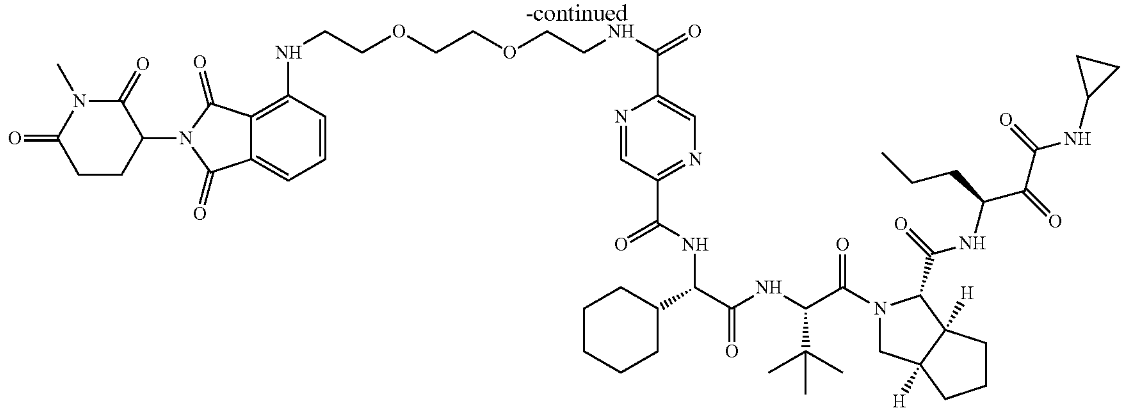

(20)

To a solution of 5-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.028 mmol) and 4-(2-(2-(2-aminoethoxy)ethoxy)ethylamino)-2-(1-methyl-2,6-dioxopiperidin-3-yl)isoindoline-1,3-dione TFA salt (15 mg, 0.028 mmol) in DMF (1 mL), DIEA (18 mg, 0.14 mmol) and HATU (21 mg, 0.055 mmol) were added at 0° C. The reaction was stirred for 10 minutes. The reaction mixture was purified with HPLC to get compound 20 (12 mg, 0.0107 mmol, 38% yield).

LC/MS m/z calculated for $[M+H]^+$ 1124.6, found 1124.6.

Example 21: The Synthesis of N2-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(1-methyl-2,6-dioxopiperidin-3-yl)-1,3-dioxoisoindolin-4-ylamino)ethoxy)ethoxy)ethyl)pyrazine-2,5-dicarboxamide (21)

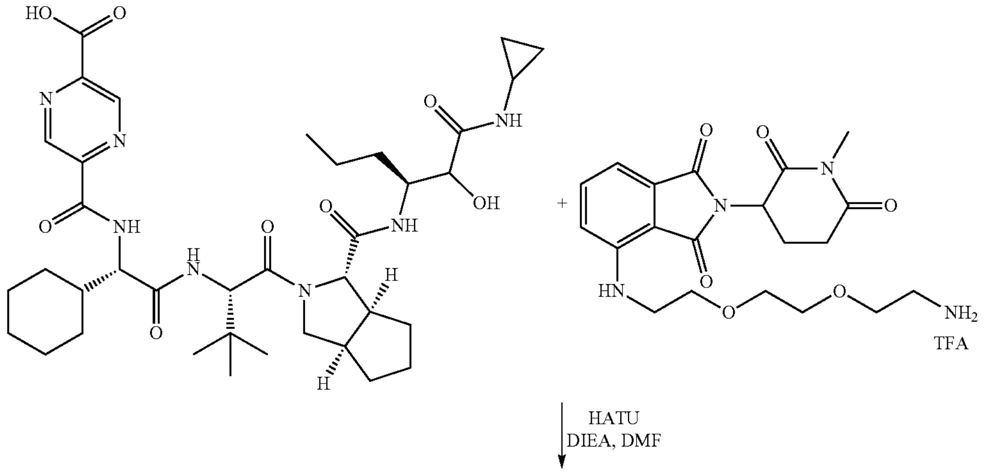

-continued

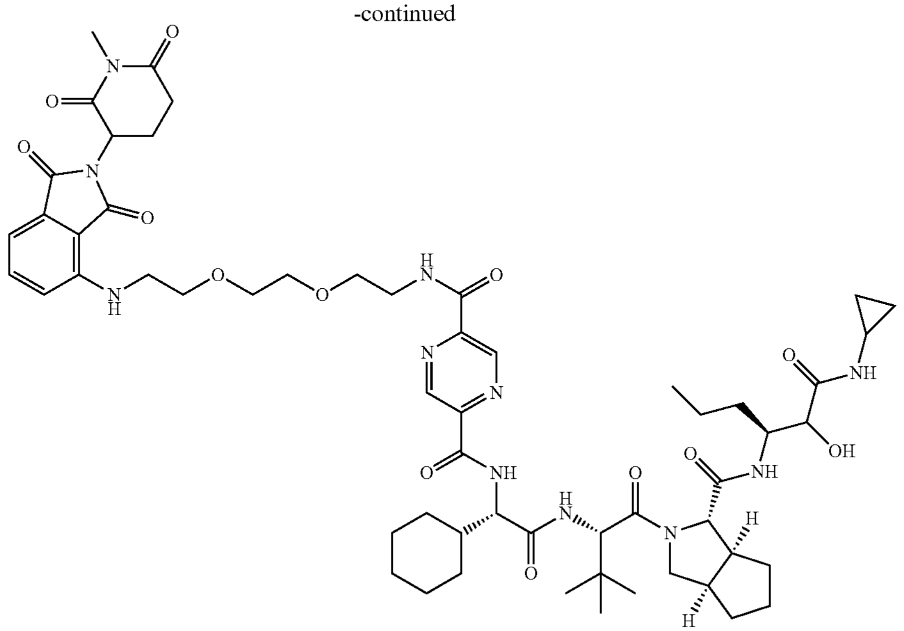

(21)

To a solution of 5-((1S)-1-cyclohexyl-2-((2S)-1-((1S,3aR,6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (10 mg, 0.0138 mmol) and 4-(2-(2-(2-aminoethoxy)ethoxy)ethylamino)-2-(1-methyl-2,6-dioxopiperidin-3-yl)isoindoline-1,3-dione TFA salt (7.3 mg, 0.0138 mmol) in DMF (1 mL), DIEA (9 mg, 0.069 mmol) and HATU (10.5 mg, 0.0276 mmol) were added at 0° C. The mixture was stirred for 10 minutes. The reaction mixture was purified with HPLC to get compound 21 (7.9 mg, 0.0070 mmol, 51% yield).

LC/MS m/z calculated for $[M+H]^+$ 1126.6, found 1126.6.

Example 22: Synthesis of N2-((S)-1-cyclohexyl-2-((S)-1-((1S,3aR,6aS)-1-((S)-1-(cyclopropylamino)-1,2-dioxohexan-3-ylcarbamoyl)hexahydrocyclopenta[c]pyrrol-2(1H)-yl)-3,3-dimethyl-1-oxobutan-2-ylamino)-2-oxoethyl)-N5-(2-(2-(2-(2-(1-methyl-2,6-dioxopiperidin-3-yl)-1,3-dioxo-2,3-dihydro-1H-benzo[de]isoquinolin-5-yloxy)ethoxy)ethoxy)ethyl)pyrazine-2,5-dicarboxamide (22)

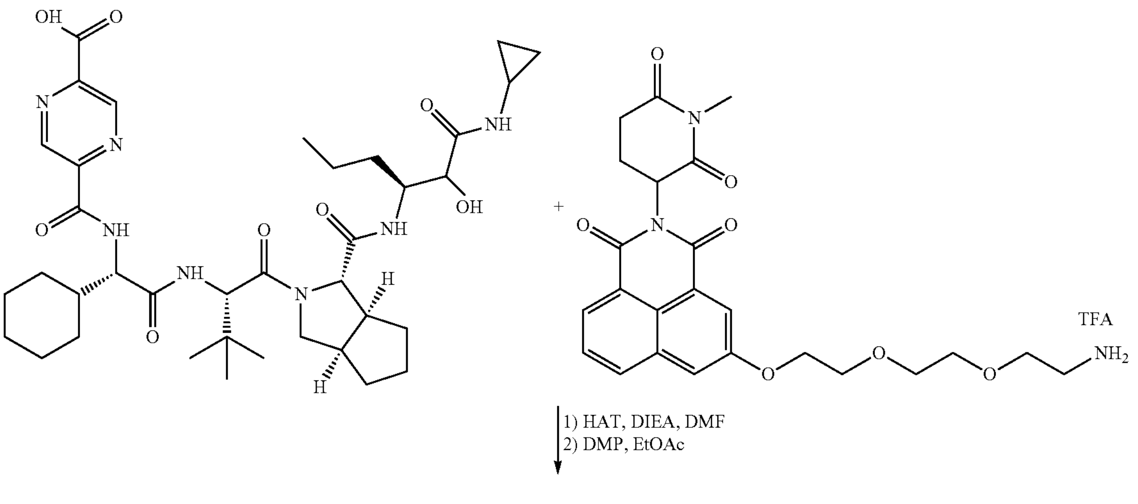

-continued

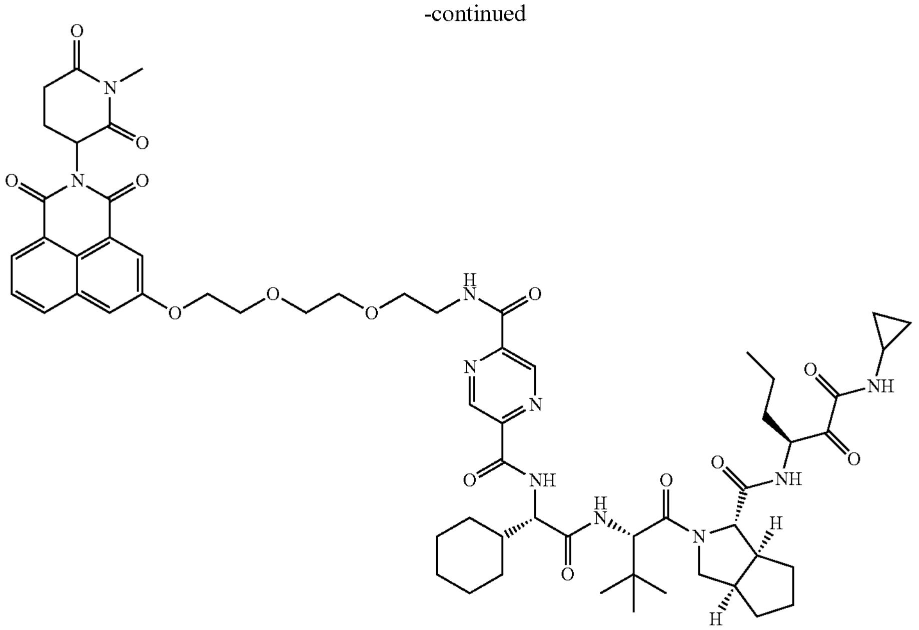

(22)

To a solution of 5-((1S)-1-cyclohexyl-2-((2S)-1-((1S,3aR, 6aS)-1-((3S)-1-(cyclopropylamino)-2-hydroxy-1-oxohexan-3-ylcarbamoyl)hexahydrocyclopenta[c]pyrrol-2(1H)-yl)-3,3-dimethyl-1-oxobutan-2-ylamino)-2-oxoethylcarbamoyl)pyrazine-2-carboxylic acid (20 mg, 0.027 mmol) and 5-(2-(2-(2-aminoethoxy)ethoxy)ethoxy)-2-(1-methyl-2, 6-dioxopiperidin-3-yl)-1H-benzo[de]isoquinoline-1,3(2H)-dione TFA salt (16 mg, 0.027 mmol) in DMF (1 mL), DIEA (18 mg, 0.138 mmol) and HATU (21 mg, 0.054 mmol) were added at 0° C. The reaction was stirred for 10 min. The solvent was evaporated under vacuum to obtain a crude product. Without any purification, the residue was dissolved in ethyl acetate (1 mL). DMP (32 mg, 0.076 mmol) was added to the mixture at 0° C. The reaction was stirred for 6 hours. After Celite® filtration and evaporation of the solvent, the crude product was purified with HPLC to get compound 22 (6.7 mg, 0.0057 mmol, 21% yield in two steps).

LC/MS m/z calculated for $[M+H]^+$ 1175.6, found 1175.6.

Example 23: Transient Cellular HCV NS3 Degradation Assay

A system was set up to monitor NS3 degradation in the absence of other processes of the infectious viral cycle. An inducible cell line expressing the full-length HCV NS3 protein fused to eGFP and linked to mCherry protein via a linker containing the FMVD 2A self-cleavage sequence was constructed. Expressed in the absence of its cofactor, NS4A, the NS3 protein lacks any enzymatic activity, and the abundance of the NS3-eGFP fusion protein can be reliably monitored by eGFP fluorescence. Since the mCherry portion of the fusion protein is cleaved off during translation, its abundance in cells is not affected by small molecule-induced degradation of NS3-eGFP, and thus it serves as a control for protein expression. The constructed cell line was used to screen all of the telaprevir-derived degronimids and identified compounds that triggered degradation of the HCV NS3 target.

Figure 2:
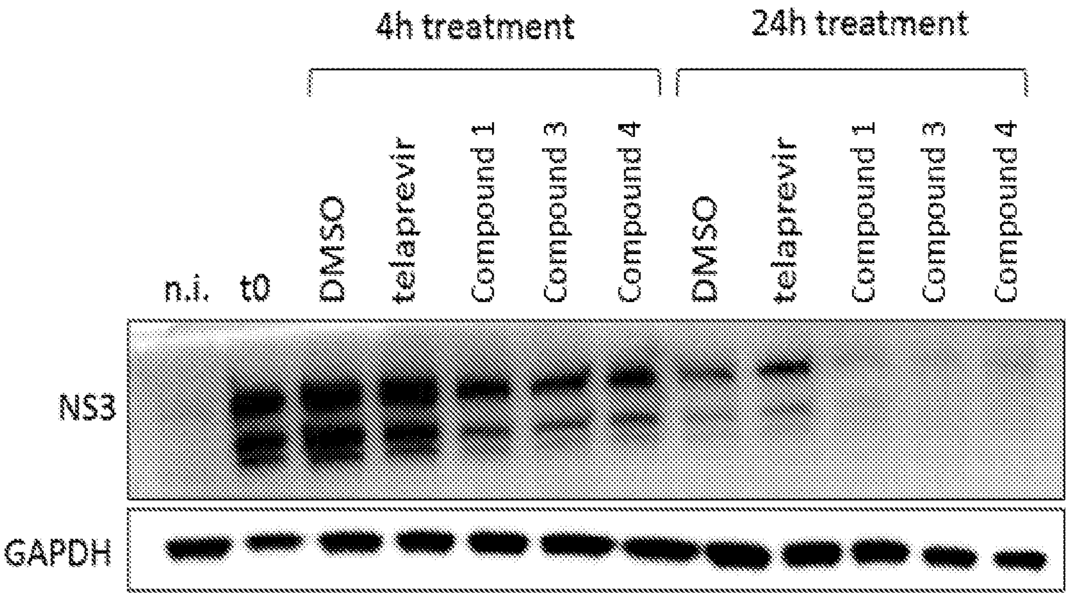
FIG. 2 is a photograph of a Western blot showing degradation of HCV NS3 after 4 hour and 24 hour treatments with telaprevir, and inventive compounds 1, 3 and 4.

Results of the transient cellular HCV NS3 degradation assay are shown in FIG. 1 and FIG. 2. FIG. 1 is a graph showing transient cellular HCV NS3 degradation by treatment with compounds 1 ($IC_{50}$=669 nM), 3 ($IC_{50}$=489 nM), 4 ($IC_{50}$=2680 nM), and 13 ($IC_{50}$=50 nM). FIG. 1 shows that a 4 hour treatment with increasing concentrations of each small molecule degrader led to a decrease in the NS3 eGFP fusion protein steady-state abundance in cells, and that this activity was not observed with parental compound, telaprevir. The NS3-eGPF and mCherry positive cells were quantified by flow cytometry and the concentration that led to a 50% reduction in NS3-eGFP accumulation ($IC_{50}$) was determined by nonlinear regression.

FIG. 2 is a photograph of a Western blot showing degradation of HCV NS3 after 4-hour and 24-hour treatments with telaprevir and inventive compounds 1, 3 and 4. It shows that treatments with the degrader small molecules caused a specific reduction in steady-state abundance of the NS3-eGFP and NS3-eGFP-mCherry fusion proteins in cells.

Example 24: NS3 Degradation Competition Assay

The expression of the NS3 fusion protein was induced prior to the treatment of the NS3 expressing cells with an excess of the cereblon ligand lenalidomide. This treatment consistently blocked small molecule-induced degradation of HCV NS3, most likely by competing with the degraders for binding to cereblon.

Figure 3A:
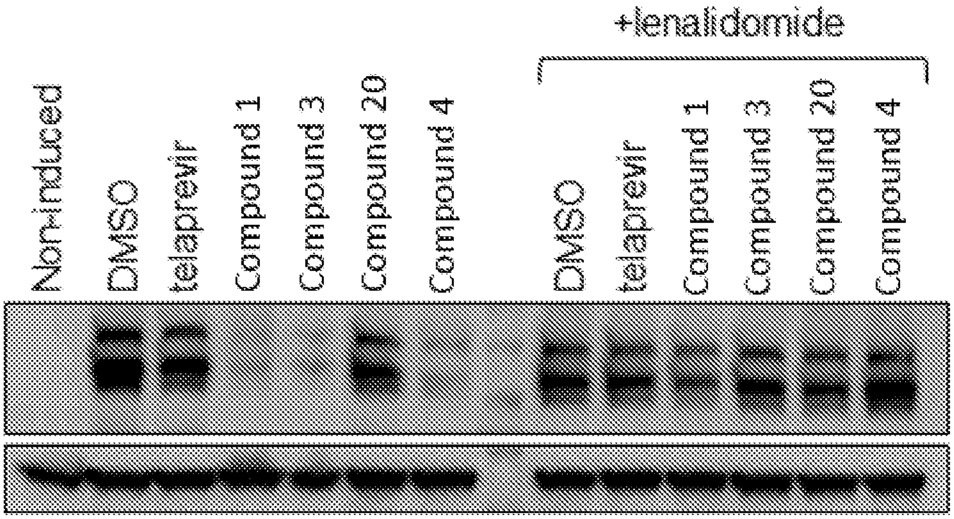
FIG. 3A-FIG. 3B are photographs of Western blots showing degradation of HCV NS3 in the absence and presence of lenalidomide.
Figure 3B:
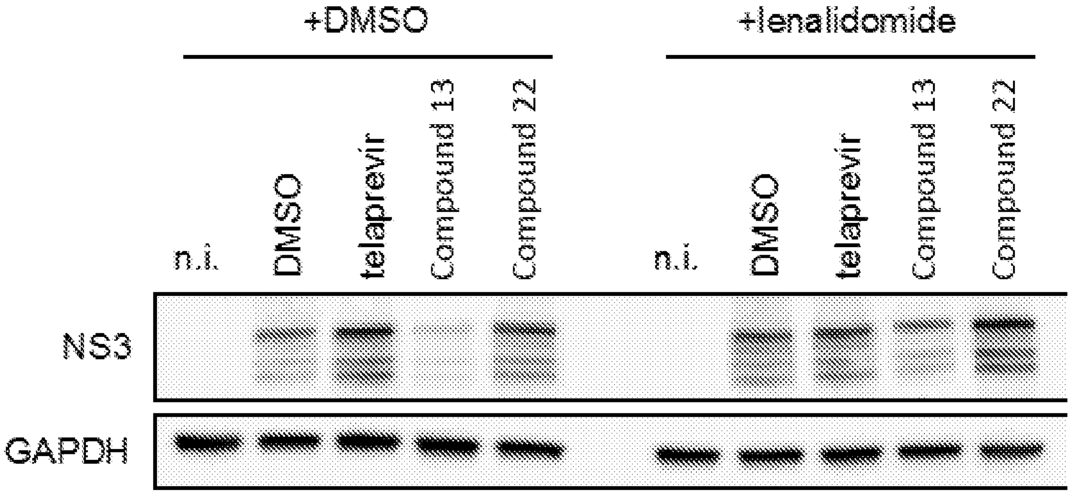

Results of the competition assay are shown in FIG. 3. FIG. 3 is a photograph of a Western blot showing degradation of HCV NS3 in the absence and presence of lenalidomide. Lenalidomide inhibited degradation of NS3 by inventive compounds 1, 3, 4 and 13, indicating competition for E3 ligase. Compounds 20 and 22 are negative controls that do not bind the E3 ligase and thus showed no significant degradation of NS3 in the presence or absence of lenalidomide.

Negative Controls for the Degrader Compounds of the Present Application

Figure 4:
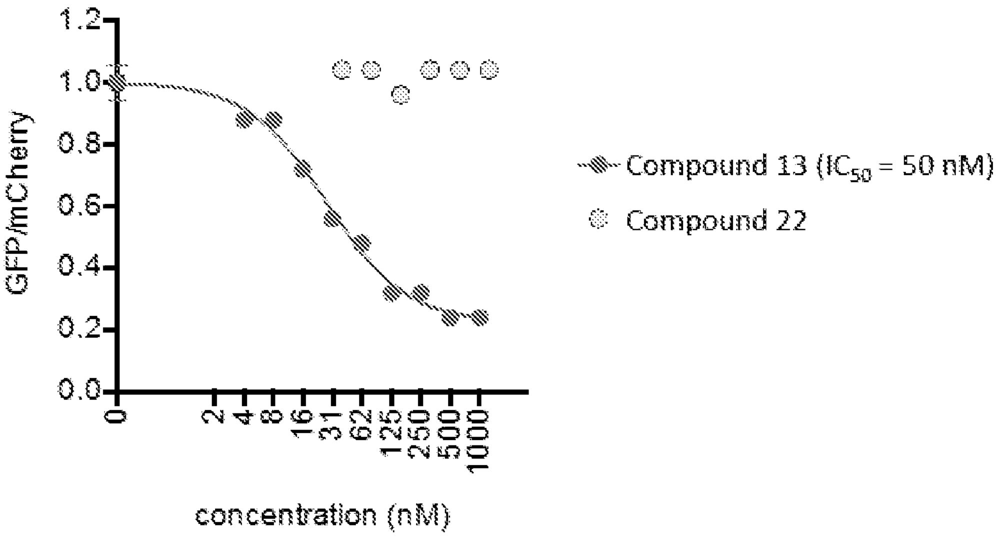
FIG. 4 is a graph showing the results of a transient cellular HCV NS3 degradation assay with inventive compound 13 ($IC_{50}$=50 nM) and 22 (negative control).
Figure 5:
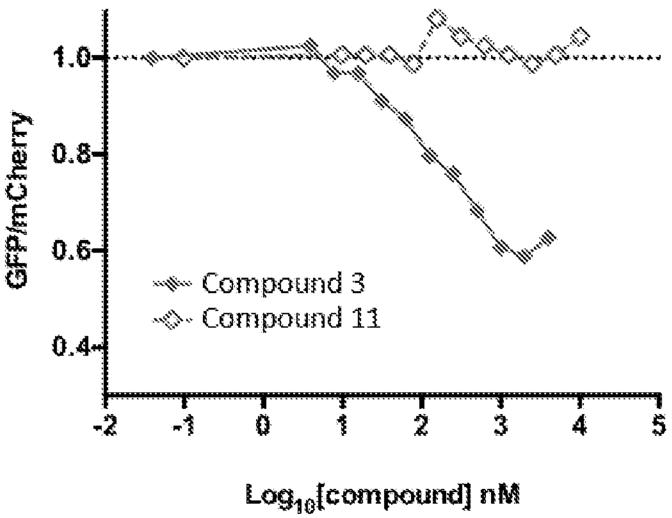
FIG. 5 is a graph showing the results of a transient cellular HCV NS3 degradation assay with inventive compounds 3 and 11.

Compound 22 is a negative control for inventive compound 13 and thus it is predicted to be unable to bind cereblon due to methylation of the glutarimide. FIG. 4 shows the results of a transient cellular HCV NS3 degradation assay. The NS3 expressing cells were treated with increasing concentrations of compounds 13 and 22 for 4 hours. As hypothesized, the negative control (22) was unable to bind cereblon and consequently did not degrade HCV NS3 (FIG. 4). Compound 11 is an alpha-hydroxylamide analog of compound 13 that cannot form a covalent bond with the catalytic serine of the HCV NS3/4A protease due to a modification of the α-ketoamide group. FIG. 5 shows the results of a transient cellular HCV NS3 degradation assay. The NS3 expressing cells were treated with increasing concentrations of compounds for 4 hours. Compound 11 did not mediate degradation of the transiently expressed HCV NS3 protein, indicating that the formation of a covalent complex with the viral protein is essential for targeted degradation.

A methyl substitution on the nitrogen of the pyridinyl group of the degron portion of compounds 19-22 abolished binding to cereblon (e.g., compound 22 in FIG. 4).

Example 25: Antiviral Assays

The antiviral activity of the degraders was evaluated in cell culture in a subgenomic replicon assay and an infectious assay. In the subgenomic replicon assay, the hepatoma cell line Huh7.5 was transfected with a HCV subgenomic replicon and treated with small molecules. The luciferase activity encoded by the subgenomic replicon served as a measure for viral replication. In the infectious assay, Huh7.5 cells were infected with HCV, and treated with small molecules. The amount of infectious virus released to the supernatants after treatment with the small molecule degraders served as a measure for their antiviral activity. While most of the candidate degraders exhibited decreased antiviral activity versus telaprevir, inventive compound 13 exhibited antiviral potency close to that of the parental compound. The activity of the compounds described herein is dependent on protein degradation mediated by the cereblon E3 ligase, as HCV NS3 levels are partially rescued in the cereblon-deficient Huh7.5 cell line.

Figure 6:
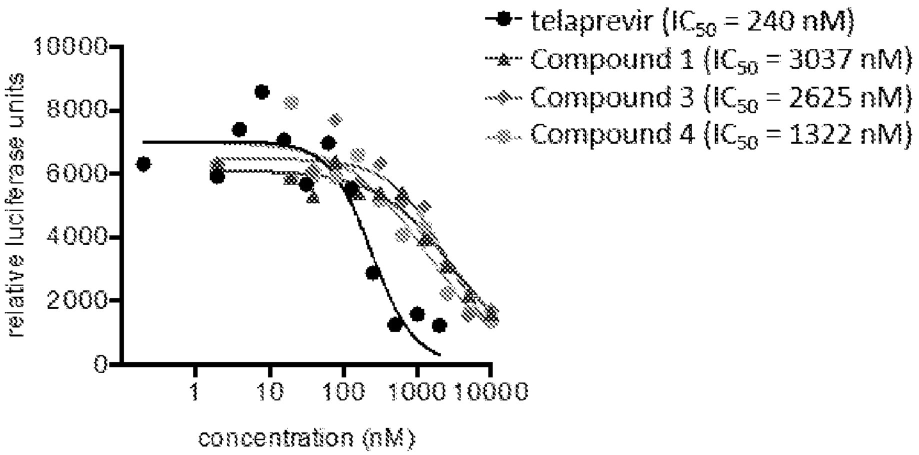
FIG. 6 is a graph showing the results of an antiviral subgenomic replicon assay with telaprevir ($IC_{50}$=240 nM) and inventive compounds 1 ($IC_{50}$=3037 nM) 3 ($IC_{50}$=2625 nM) and 4 ($IC_{50}$=1322 nM).

Results of the antiviral subgenomic replicon assay are shown in FIG. 6. Huh7.5 cells were electroporated with the HCV subgenomic replicon and treated after 24 hours with a range of small molecule concentrations. The luciferase activity encoded by the replicon was measured in cells at 48 hours post-electroporation/24 hours post-treatment. The concentration of compound that led to a 50% reduction in reporter expression levels ($IC_{50}$) was determined by non-linear regression.

Figure 7:
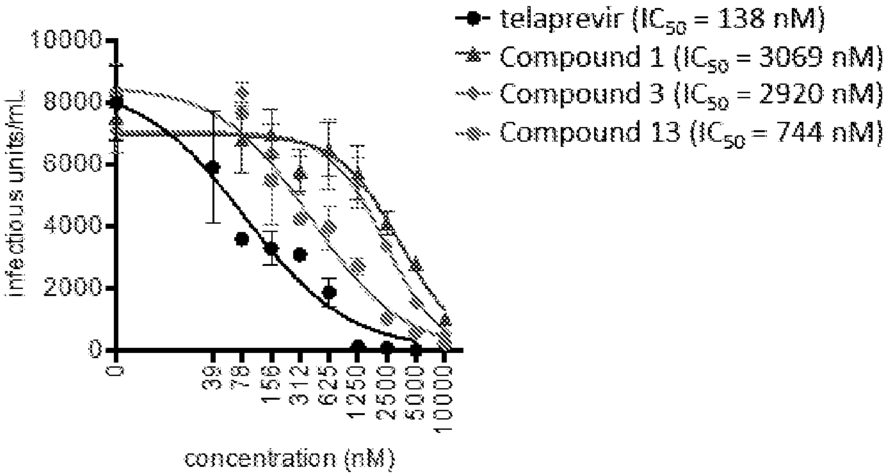
FIG. 7 is a graph showing the results of an antiviral infectious assay with telaprevir ($IC_{50}$=138 nM) and inventive compounds 1 ($IC_{50}$=3069 nM), 3 ($IC_{50}$=2920 nM) and 13 ($IC_{50}$=744 nM).
Figure 8A:
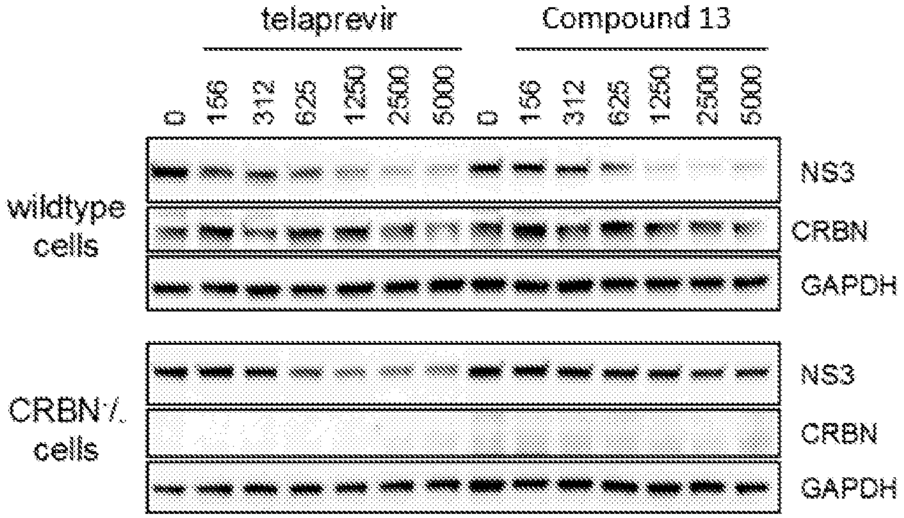
FIG. 8A is a photograph of a Western blot of accumulated HCV NS3 proteins in wild-type Huh7.5 and Huh7.5 CRBN−/− cells that were infected with HCV and treated after 24 hours with a range of telaprevir and inventive compound 13 concentrations. GAPDH was used as a loading control.
Figure 8B:
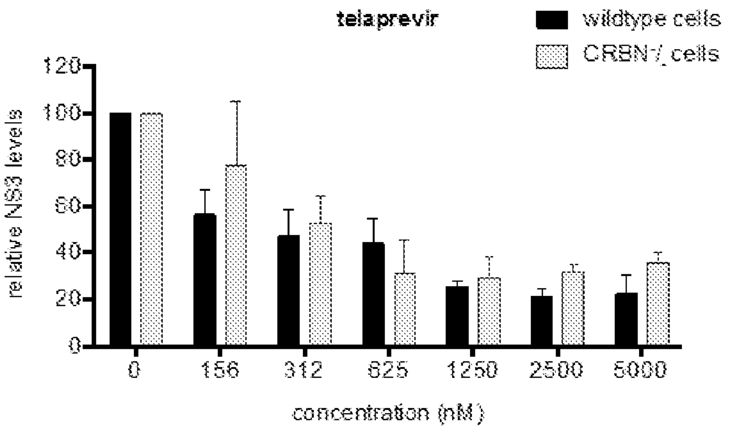
FIG. 8B and FIG. 8C are graphs showing quantification of HCV NS3 accumulation in wild-type Huh7.5 and Huh7.5 CRBN−/− cells treated with different concentrations of telaprevir and inventive compound 13, respectively.
Figure 8C:
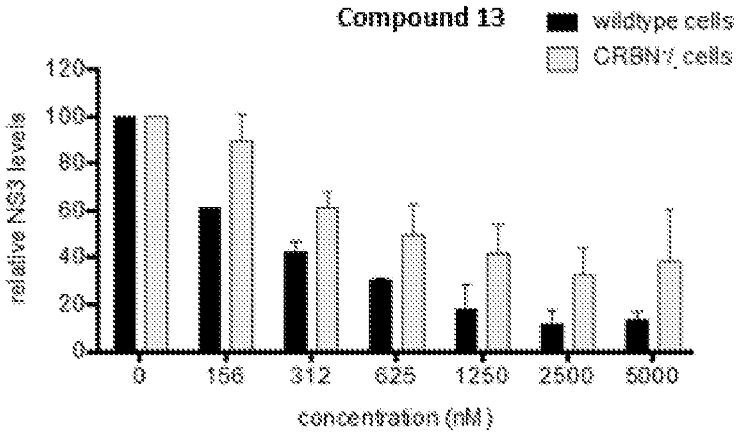
Figure 8D:
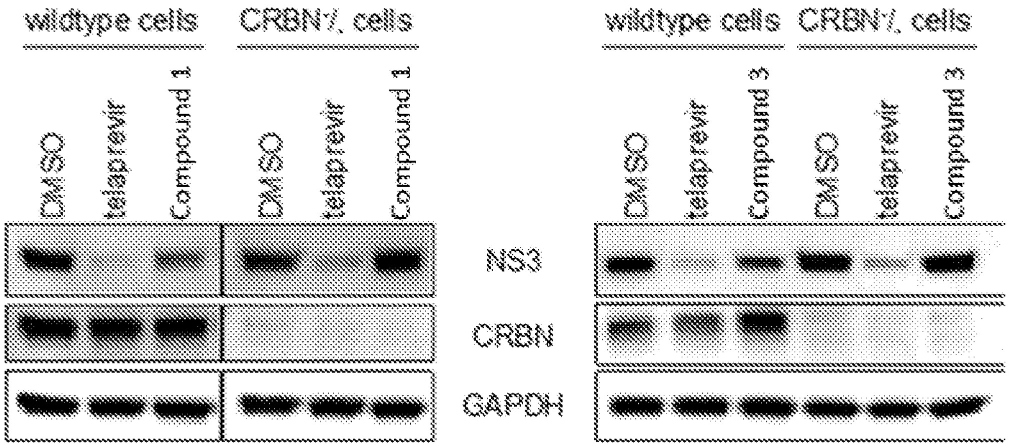
FIG. 8D is a photograph of a Western blot of accumulated HCV NS3 proteins in wild-type Huh7.5 and Huh7.5 CRBN−/− cells that were infected with HCV and treated after 24 hours with telaprevir and inventive compounds 1 and 3. GAPDH was used as a loading control.
Figure 8E:
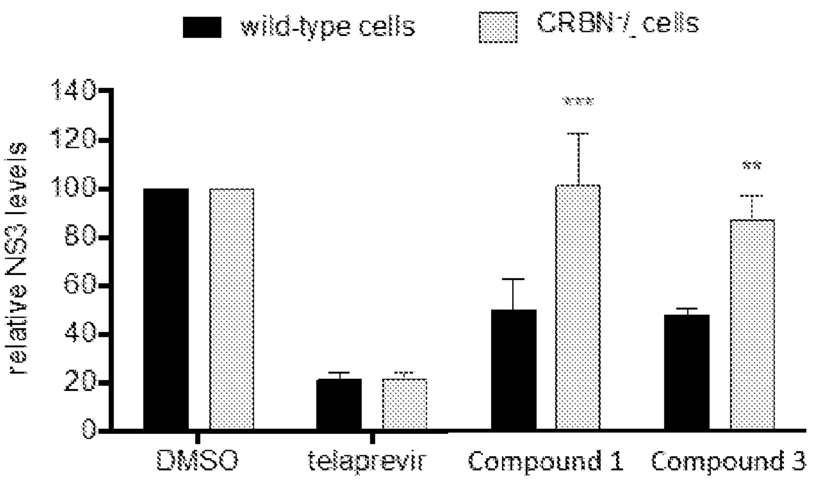
FIG. 8E is a graph showing quantification of relative HCV NS3 accumulation in wild-type Huh7.5 and Huh7.5 CRBN−/− cells treated with telaprevir and inventive compounds 1 and 3.

Results of the antiviral infectious assay are shown in FIG. 7. Huh7.5 cells were infected with HCV and treated after 24 hours with a range of small molecule concentrations. The amount of infectious virus released to the supernatants at 48 hours post-infection/24 hours post-treatment was measured using a 50% tissue infectious dose ($TCID_{50}$) assay. The concentration of compound that led to a 50% reduction in viral titers ($IC_{50}$) was determined by non-linear regression.

Results showing dependence on cereblon for antiviral activity are shown in FIG. 8. A cereblon knockout ($CRBN^{-/-}$) Huh7.5 cell line was engineered using CRISPR editing technology. Wild-type Huh7.5 and Huh7.5 $CRBN^{-/-}$ cells were infected with HCV and treated after 24 hours with a range of small molecule concentrations. The levels of HCV NS3 protein accumulation were evaluated by Western blotting, and GAPDH was used as a loading control. Quantification of the intracellular NS3 levels, relative to GAPDH levels, obtained from n≥2 experiments is shown. While the antiviral activity of the degraders was not completely alleviated in cereblon-deficient cells, a significant rescue in HCV NS3 intracellular accumulation was observed for all degraders. Results obtained with inventive compound 13 are shown in FIG. 8A-FIG. 8C. Results obtained with inventive compounds 1 and 3 are shown in FIG. 8D and FIG. 8E. These data demonstrate that part of the antiviral activity of the telaprevir-based degraders is cereblon-dependent.

Example 26: Viral Resistance Assay

Several resistance mutations have been shown to arise in patients and in cell culture during telaprevir treatment. Mutations A156S and V55A, two well-characterized resistance mutations that are located in the active site of the HCV NS3 protease where telaprevir binds, were selected. Infectious HCV clones bearing the NS3-V55A mutation or the NS3-A156S mutation were generated.

Figure 9A:
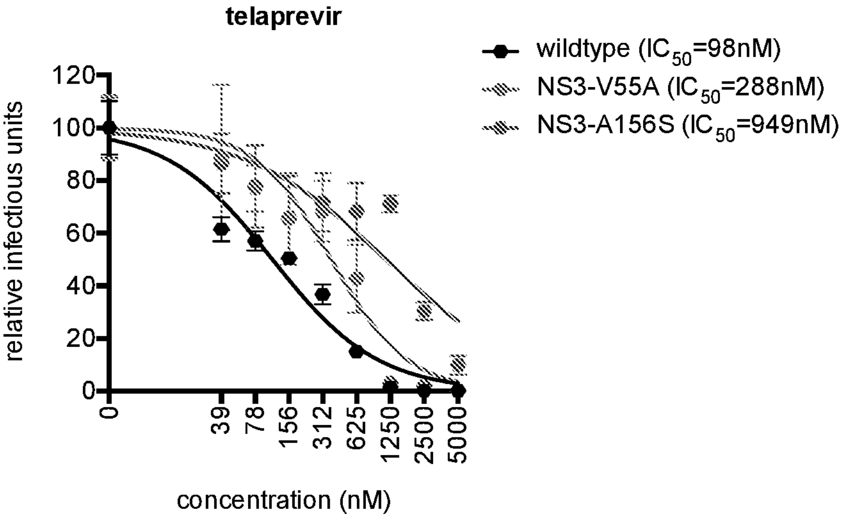
FIG. 9A is a graph showing the results of a viral resistance assay in Huh7.5 cells infected with wildtype HCV ($IC_{50}$=98 nM), or the telaprevir-resistant mutant viruses, HCV(NS3-V55A) ($IC_{50}$=288 nM) and HCV(NS3-A156S) ($IC_{50}$=949 nM) with telaprevir.
Figure 9B:
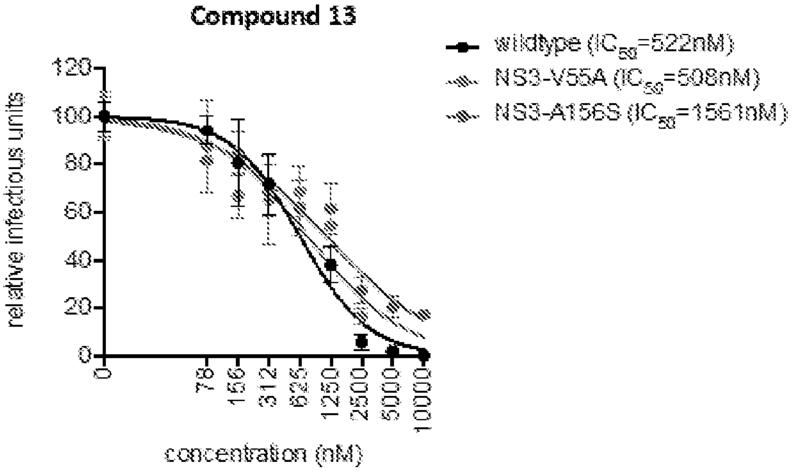
FIG. 9B is a graph showing the results of a viral resistance assay in Huh7.5 cells infected with wildtype HCV ($IC_{50}$=522 nM), or the telaprevir-resistant mutant viruses, HCV(NS3-V55A) ($IC_{50}$=508 nM) and HCV(NS3-A156S) ($IC_{50}$=1561 nM) with inventive compound 13.

Results of this viral resistance assay are shown in FIG. 9. Huh7.5 cells were infected with wildtype HCV, or the telaprevir-resistant mutant viruses, HCV(NS3-V55A) and HCV(NS3-A156S). Cells were treated 24 hours after infection with a range of small molecule concentrations. The amount of infectious virus released to the supernatants at 48 hours post-infection/24 hours post-treatment was measured using a 50% tissue infectious dose ($TCID_{50}$) assay. The concentration of compound that led to a 50% reduction in viral titers ($IC_{50}$) was determined by non-linear regression. While the NS3-A156S mutation still conferred resistance to inventive compound 13, the change in antiviral potency was only 3-fold (wildtype $IC_{50}$=522 nM; NS3-A156S $IC_{50}$=1561 nM), while it was 10-fold for telaprevir (wildtype $IC_{50}$=98 nM; NS3-A156S $IC_{50}$=949 nM). Remarkably, compound 13 had similar antiviral activities against the wildtype virus and the NS3-V55A mutant (wildtype $IC_{50}$=522 nM; NS3-V55A $IC_{50}$=508 nM), which had a more moderate resistance profile against telaprevir (3-fold change in antiviral potency: wildtype $IC_{50}$=98 nM; NS3-V55A $IC_{50}$=288 nM). Overall, the results show that inventive degrader compounds have superior antiviral activity against resistant viruses that arise upon treatment with direct-acting antivirals, and thus may have a higher barrier to resistance relative to traditional antivirals.

All patent publications and non-patent publications referred to herein are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:
1. A bifunctional compound having a structure represented by formula (I):
(I)
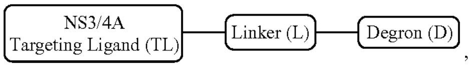
,
wherein
the NS3/4A targeting ligand is represented by structure TL1:
(TL1)
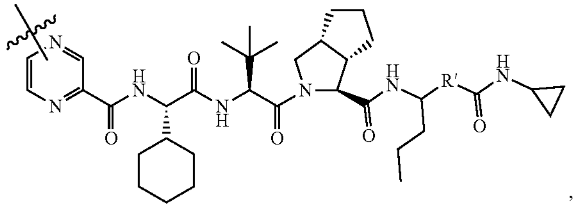
,
wherein R' is CH—OH or C═O,
the degron is represented by any one of structures D2a-D4a:
(D2-a)
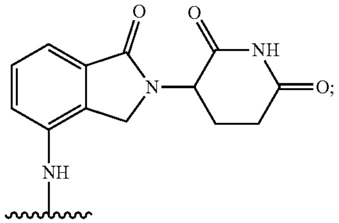
(D2-b)
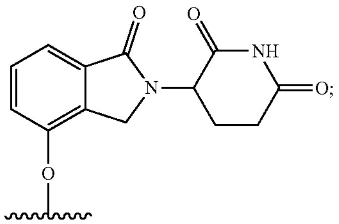
(D2-c)
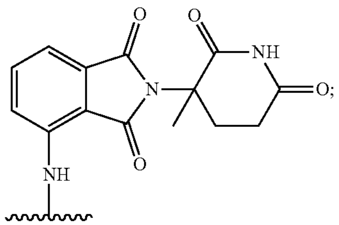
-continued
(D2-d)
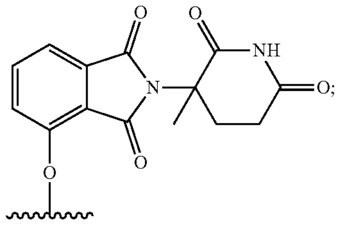
(D2-e)
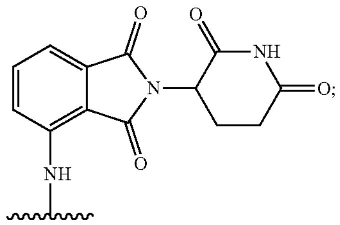
(D2-f)
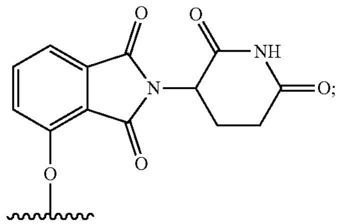
(D2-g)
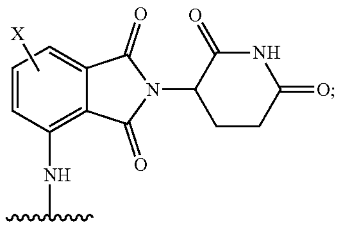
(D2-h)
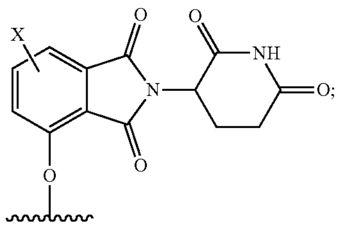
(D2-i)
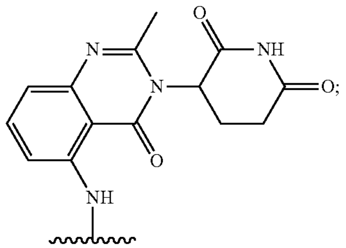

(D2-j)
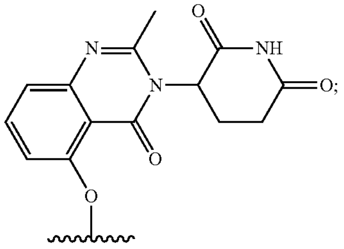
;
(D2-k)
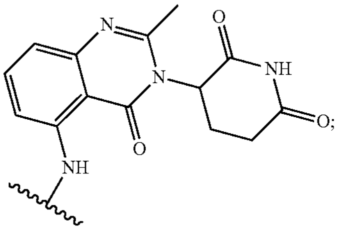
;
(D2-l)
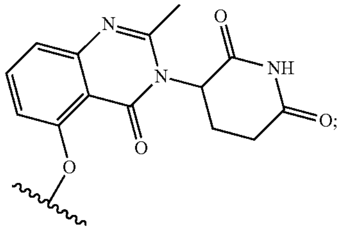
;
(D2-m)
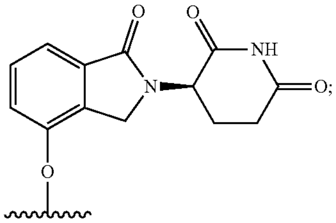
;
(D2-n)
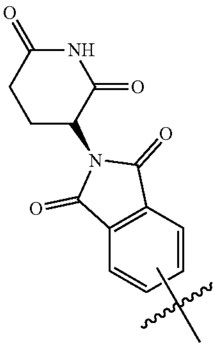
;
(D2-o)
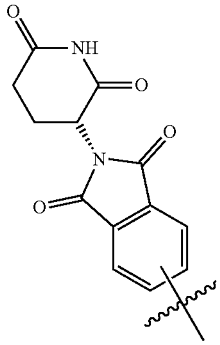
;
(D2-p)
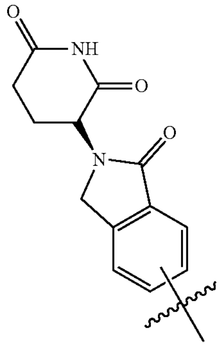
;
(D2-q)
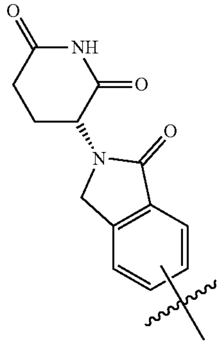
,
(D3-a)
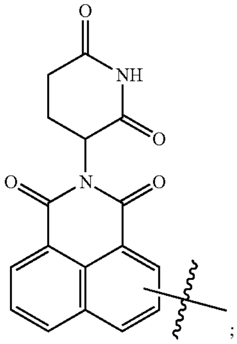
; and -continued (D4-a)

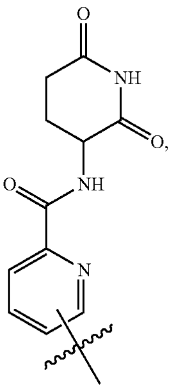

wherein X is halo, methyl, methoxy, CN, $CF_3$ or $OCF_3$, and the linker is an alkylene chain which may be interrupted by, and/or terminate (at either or both termini) at least one of —O—, —S—, —N(R")—, —C(O)—, —C(O)O—, —OC(O)—, —OC(O)O—, —C(NOR")—, —C(O)N(R")—, —C(O)N(R")C(O)—, —C(O)N(R")C(O)N(R")—, —N(R")C(O)—, —N(R")C(O)N(R")—, —N(R")C(O)O—, —OC(O)N(R")—, —C(NR")—, —N(R')C(NR")—, —C(NR")N(R")—, —N(R")C(NR")N(R")—, —$S(O)_2$—, —OS(O)—, —S(O)O—, —S(O)—, —$OS(O)_2$—, —$S(O)_2O$—, —N(R")$S(O)_2$—, —$S(O)_2$N(R")—, —N(R")S(O)—, —S(O)N(R")—, —N(R")$S(O)_2$N(R")—, —N(R')S(O)N(R')—, $C_{3-12}$ carbocyclene, 3- to 12-membered heterocyclene, 5- to 12-membered heteroarylene or any combination thereof, wherein R" is H or $C_1$-$C_6$ alkyl, wherein the one or both terminating groups may be the same or different, or a pharmaceutically acceptable salt or stereoisomer thereof.

2. The bifunctional compound of claim 1, wherein the NS3/4A targeting ligand is represented by structure:

(TL1a)

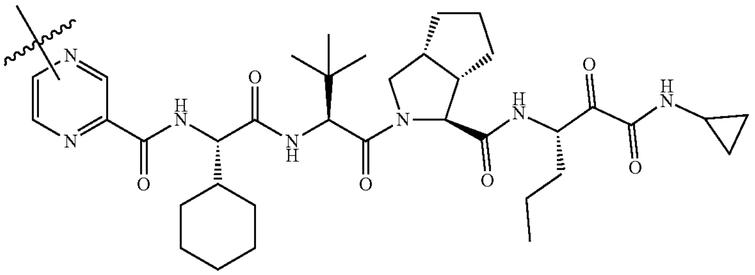

or a stereoisomer thereof.

3. The bifunctional compound of claim 1, wherein the linker is represented by a structure selected from the group consisting of:

(L10)

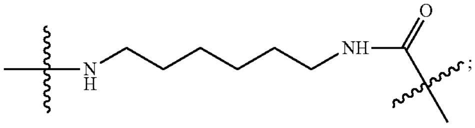

;

(L11)

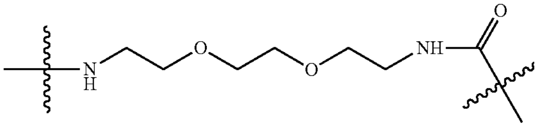

;

(L12)

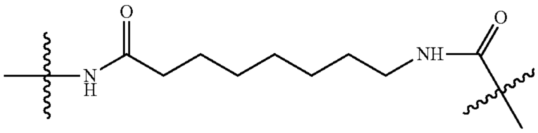

;

(L13)

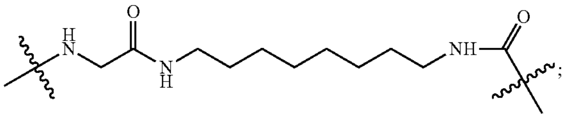

;

(L14)

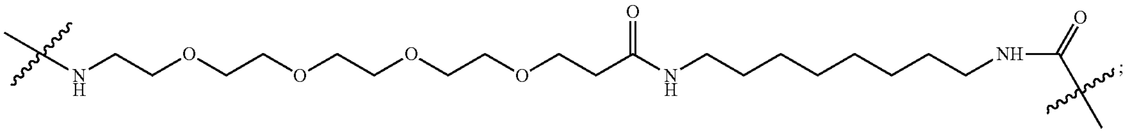

;

(L15)

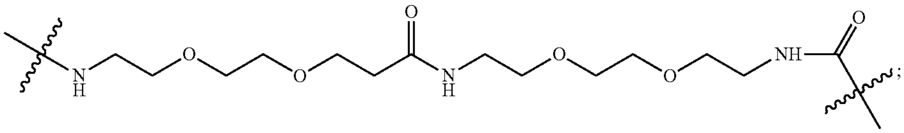

;

-continued
(L16)
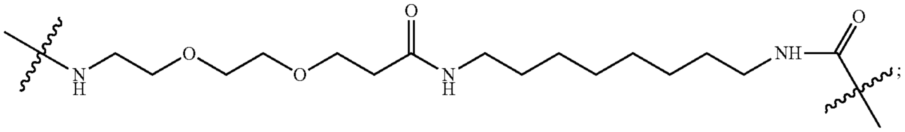
(L17)
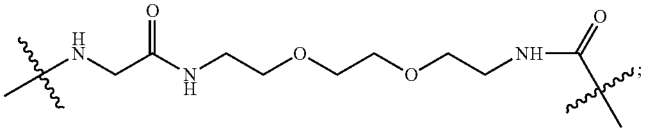
(L18)
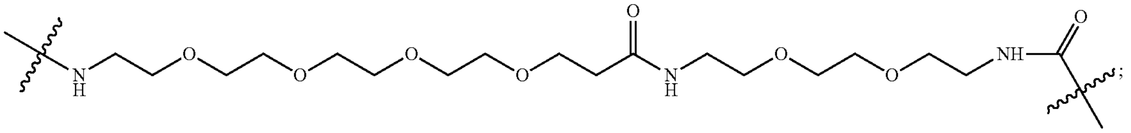
(L19)
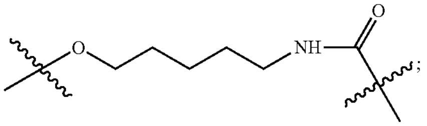
(L20)
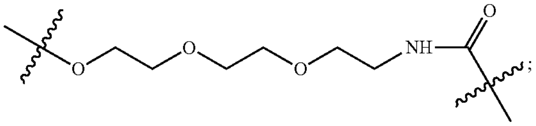
(L21)
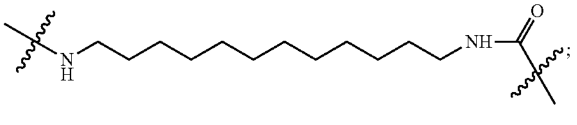
(L22)
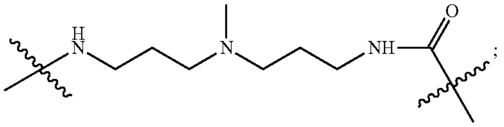
(L23)
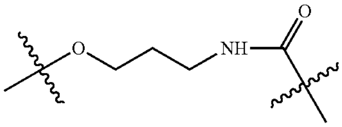
and
(L24)
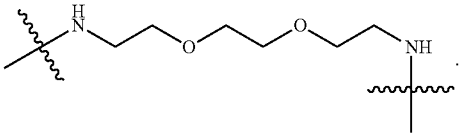
4. The bifunctional compound of claim 1, wherein the degron is represented by any one of the following structures:
(D2-a)
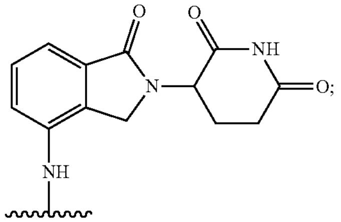
(D2-b)
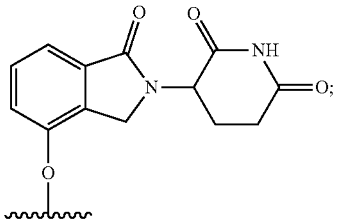
-continued
(D2-c)
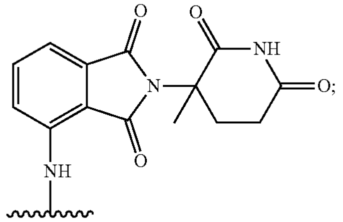
(D2-d)
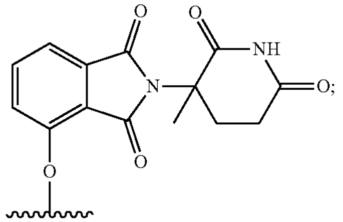

-continued
(D2-e)
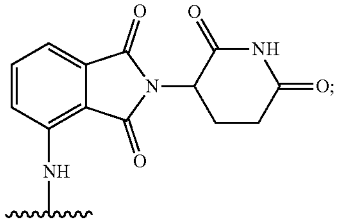
(D2-f)
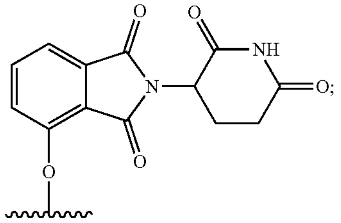
(D2-m)
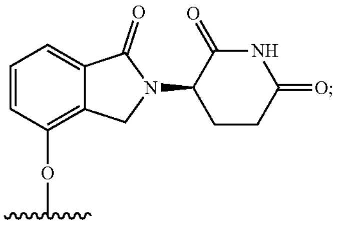
(D2-n)
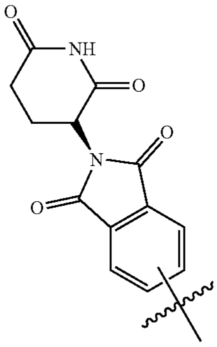
;
(D2-o)
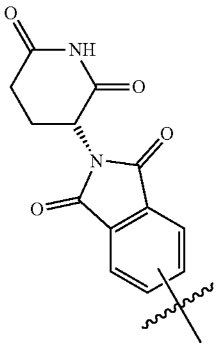
;
-continued
(D2-p)
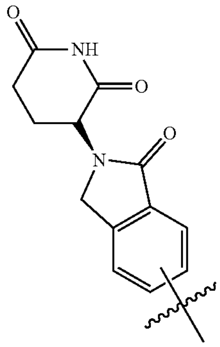
;
(D2-q)
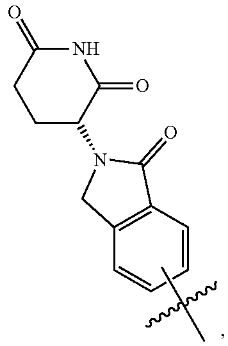
, and
(D3-a)
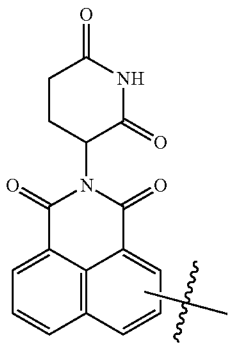
.
5. The bifunctional compound of claim 1, which is represented by a structure selected from the group consisting of:

(dg17)
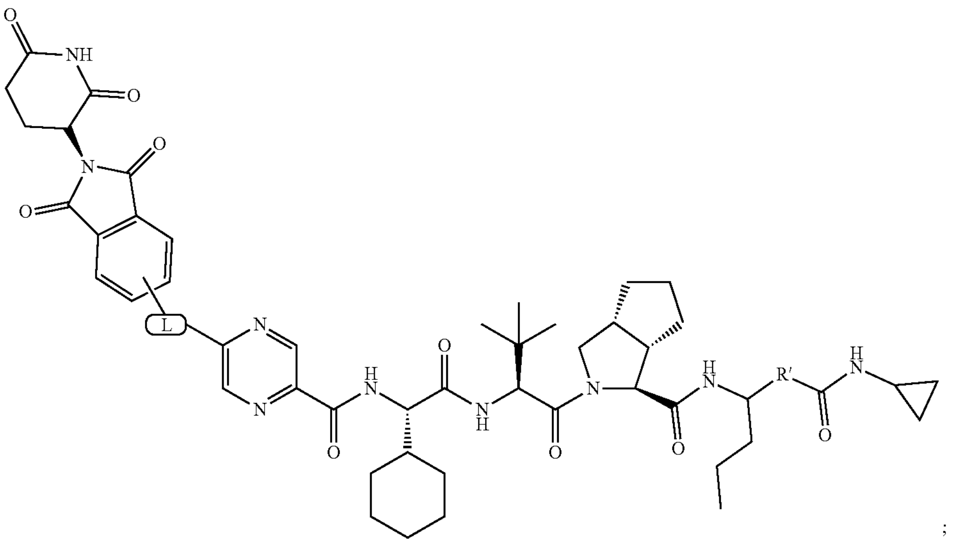
;
(dg18)
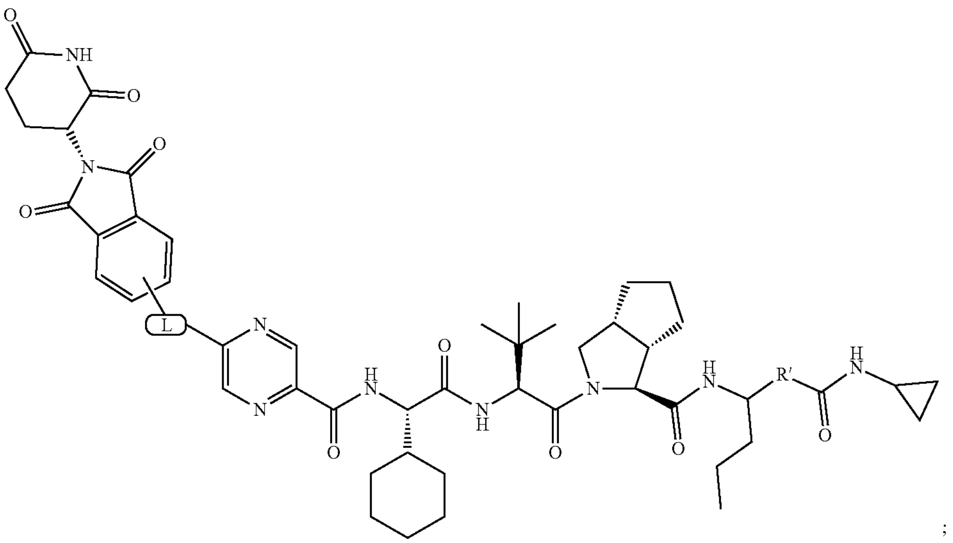
;
(dg19)
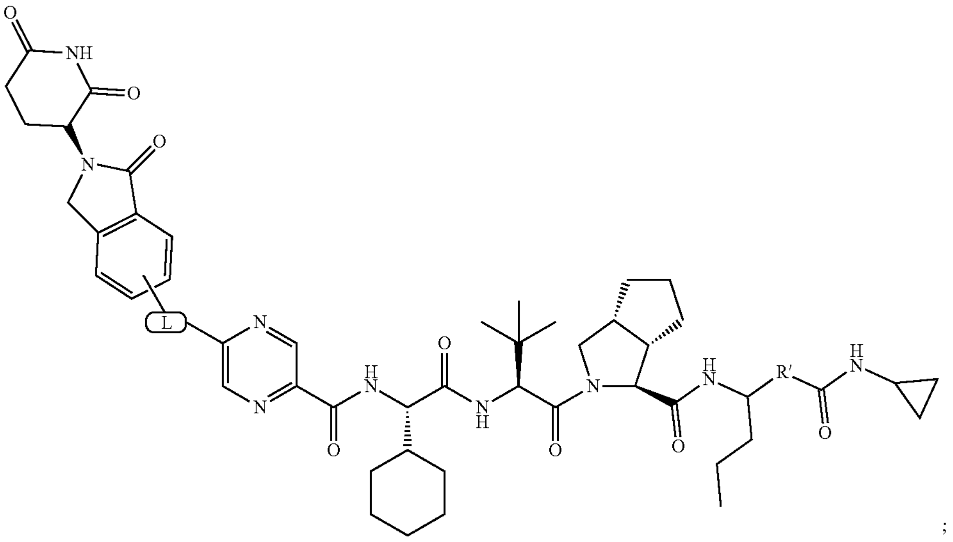
;

-continued
(dg25)
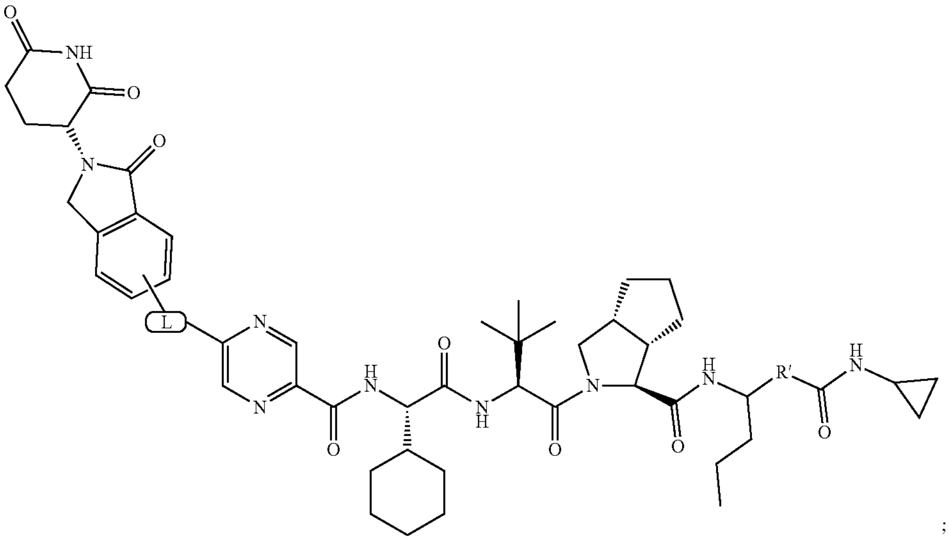
;
(dg20)
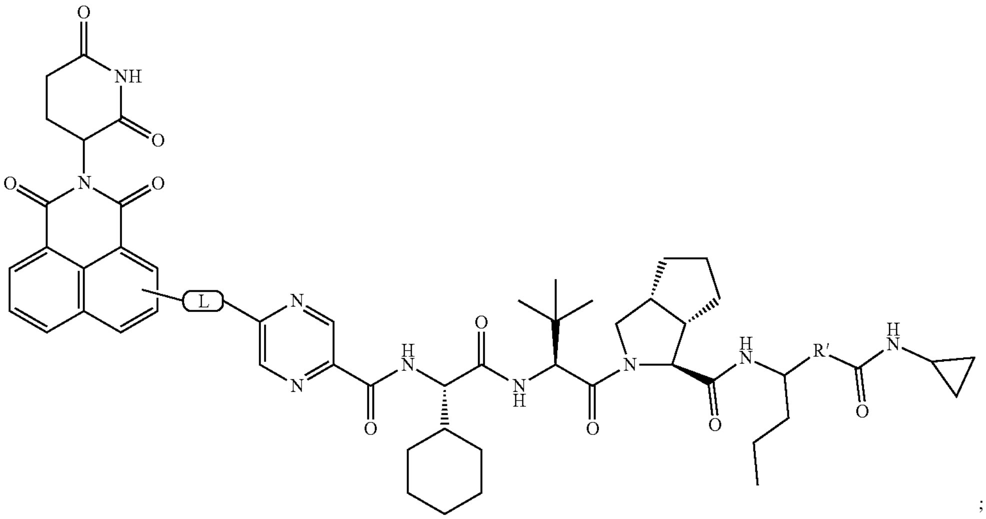
;
(dg21)
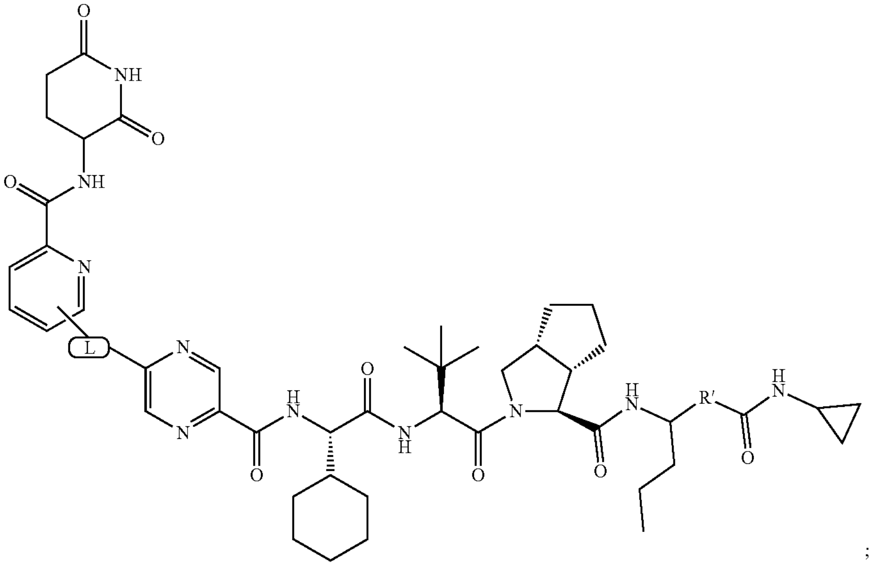
;

-continued
(dg17a)
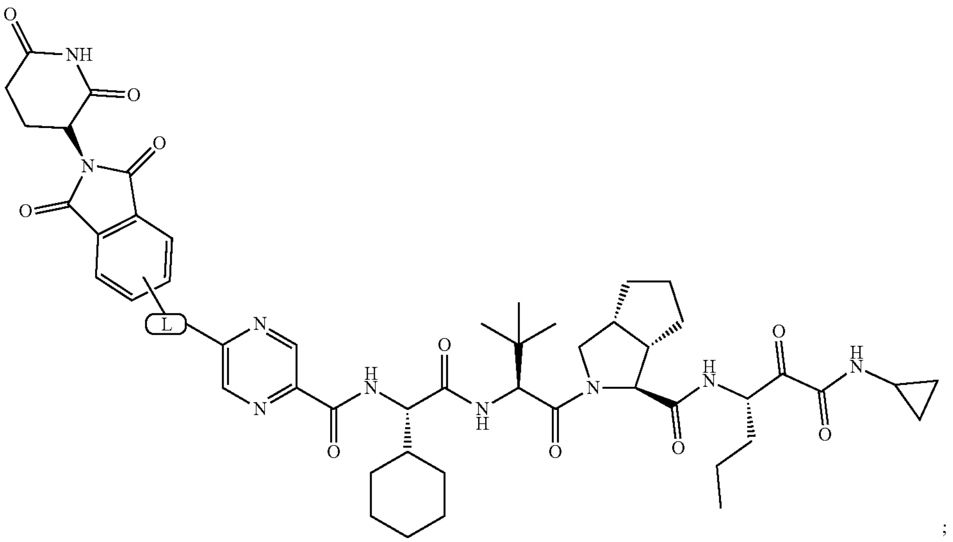
;
(dg18a)
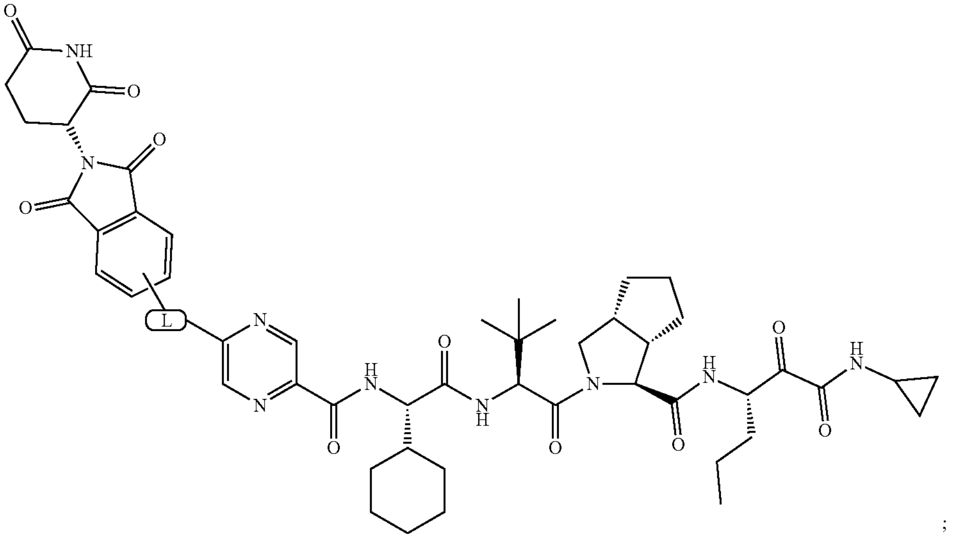
;
(dg19a)
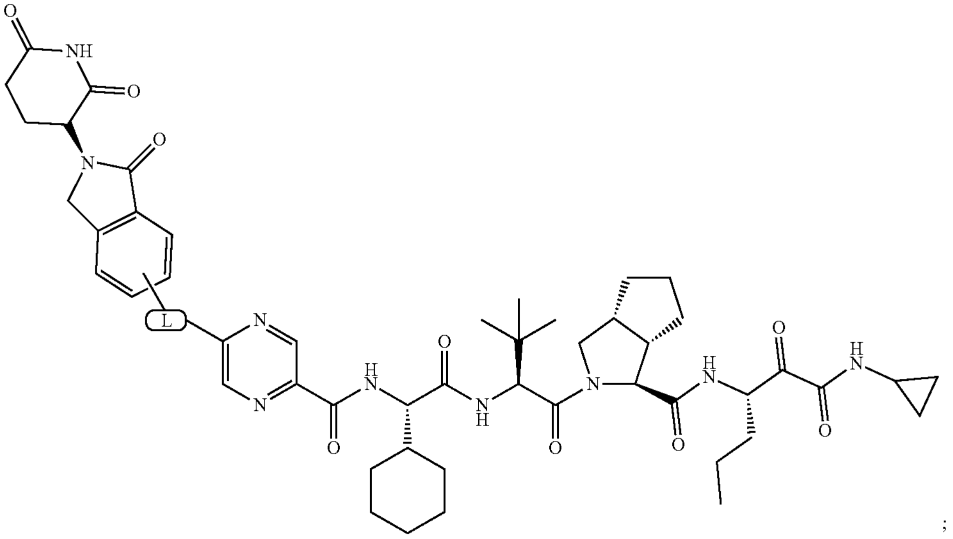
;

-continued
(dg20a)
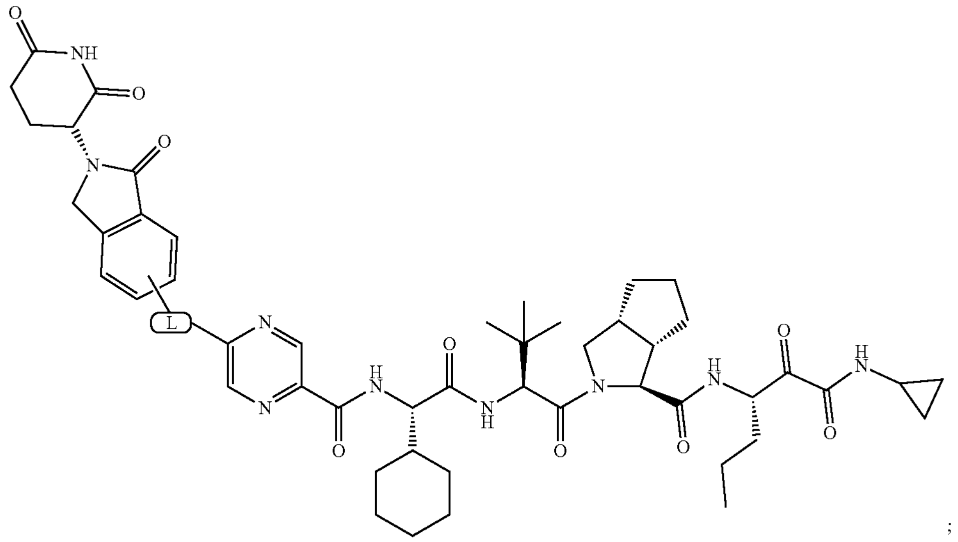
;
(dg21a)
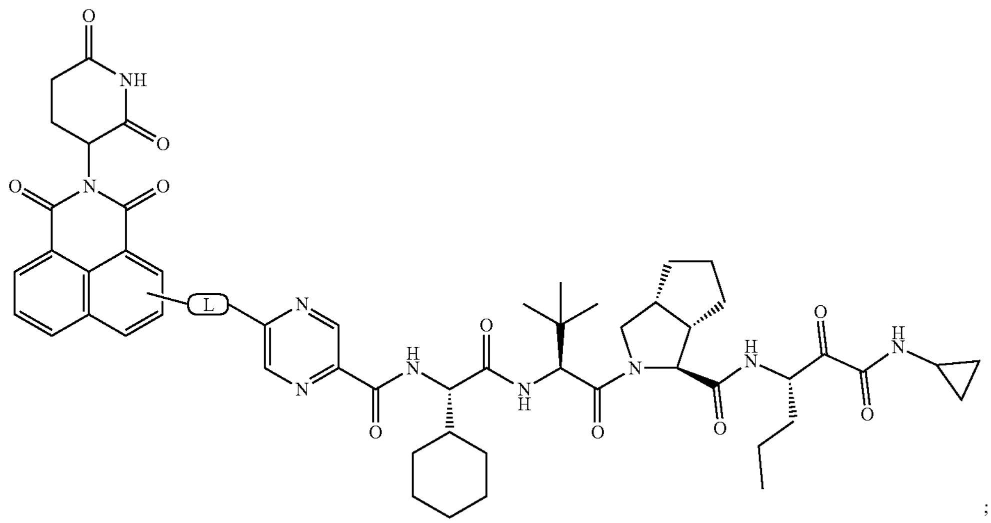
;
(dg22a)
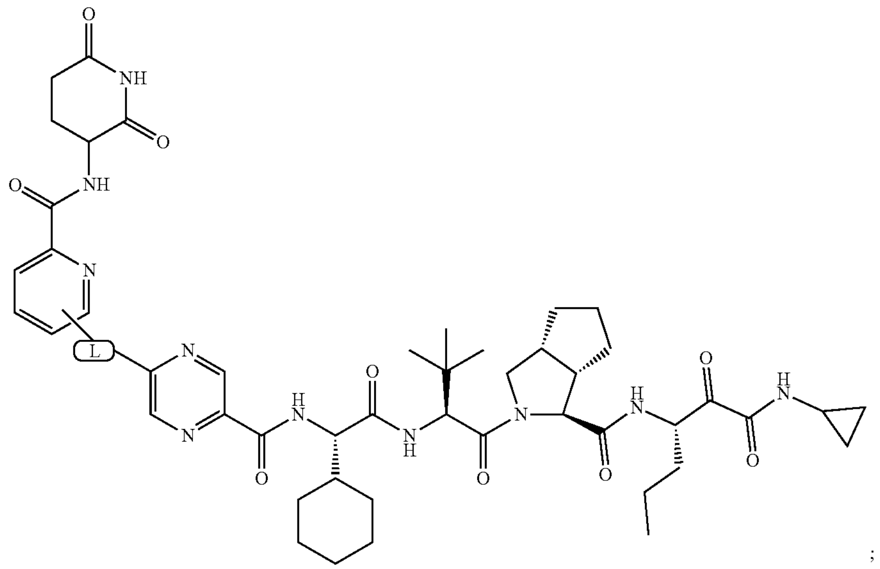
;

-continued
(dg17b)
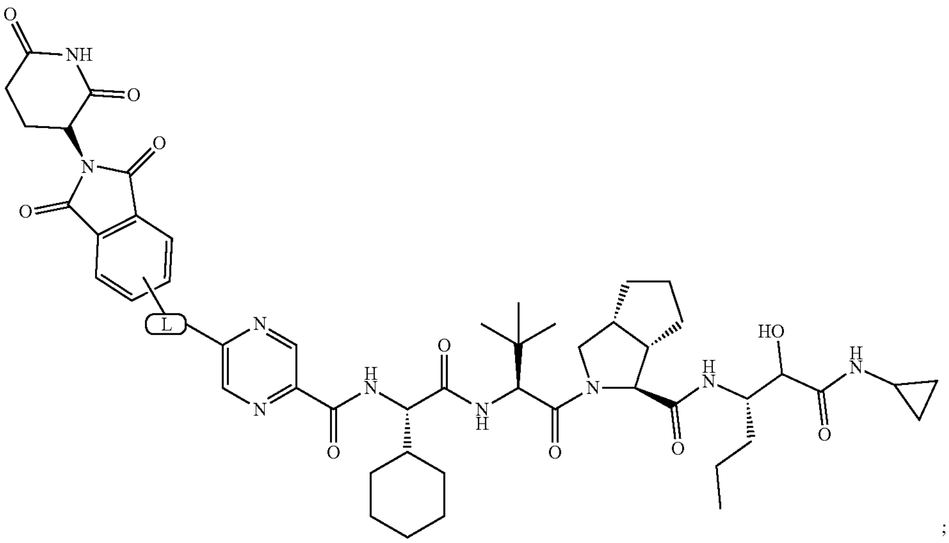
;
(dg18b)
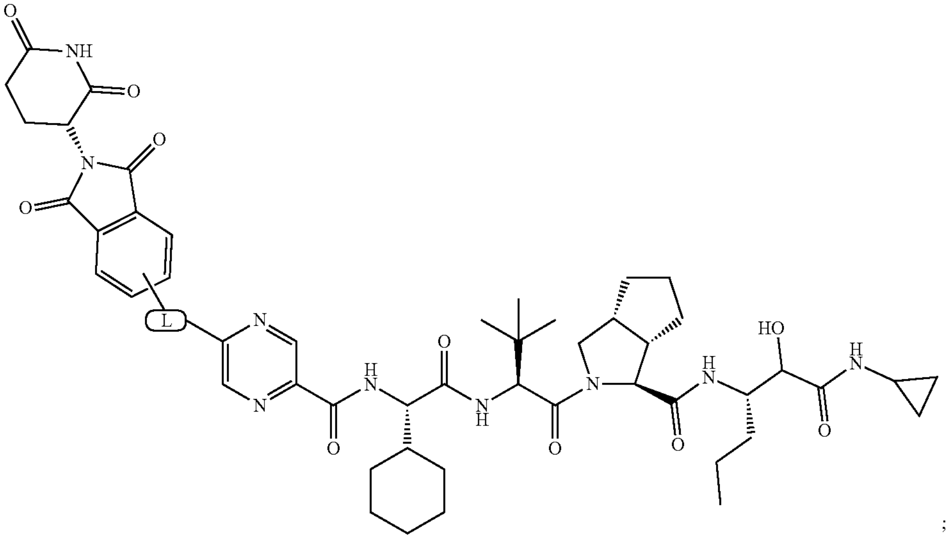
;
(dg19b)
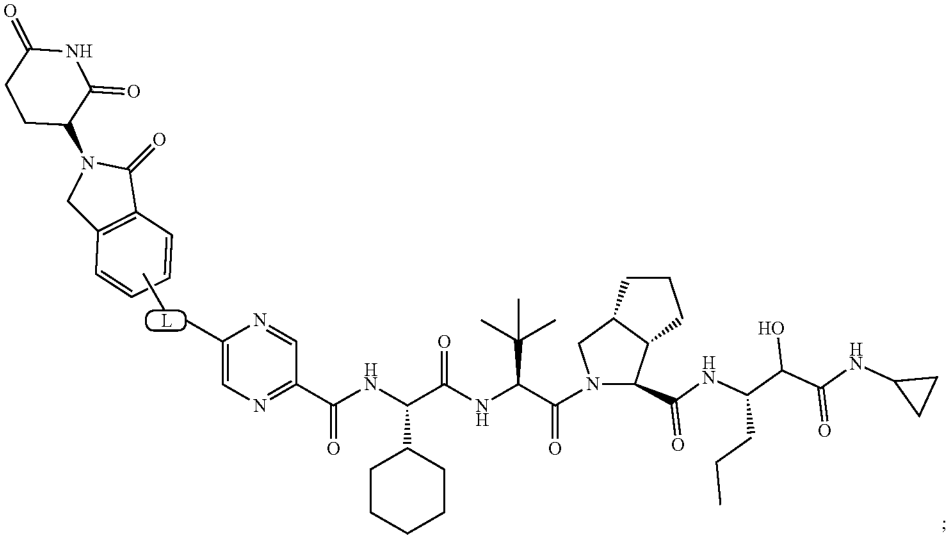
;

-continued
(dg20b)
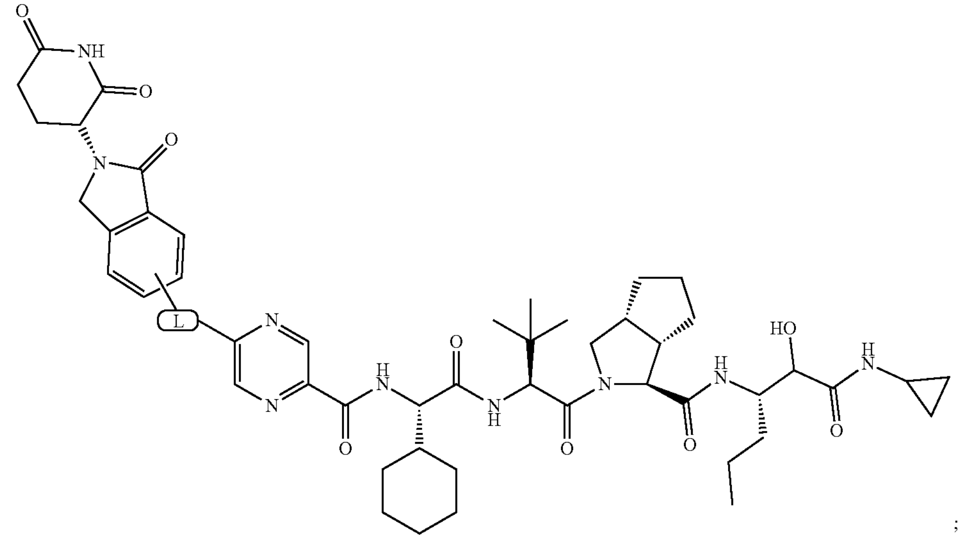
;
(dg21b)
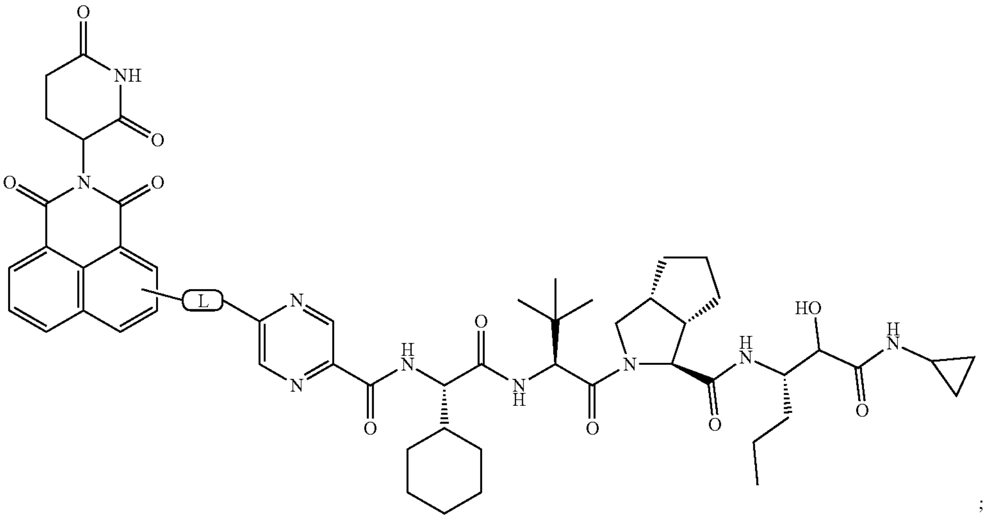
;
(dg22b)
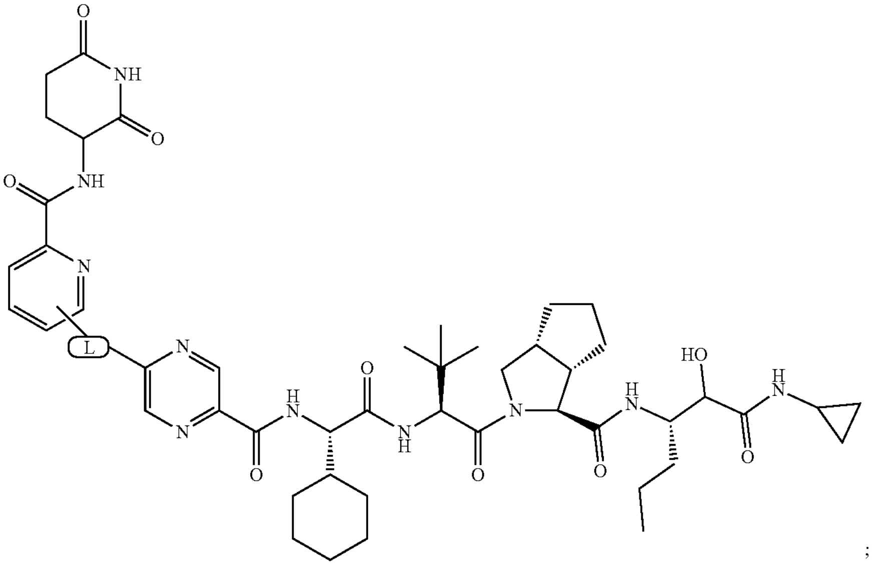
;

-continued
(dg17c)
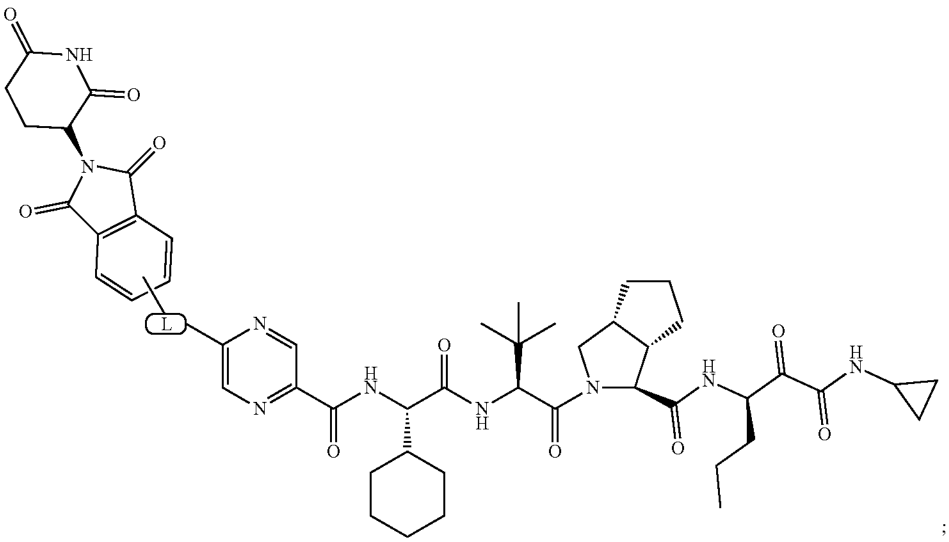
;
(dg18c)
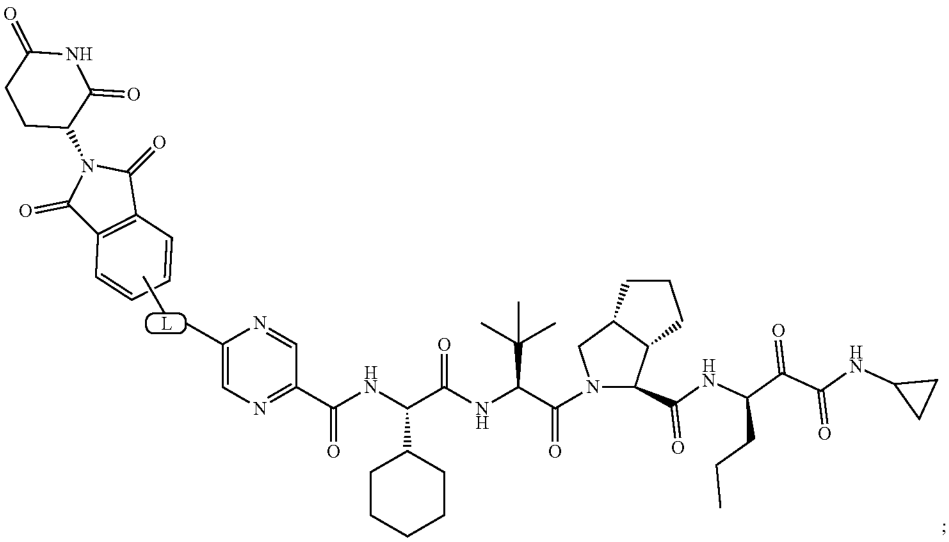
;
(dg19c)
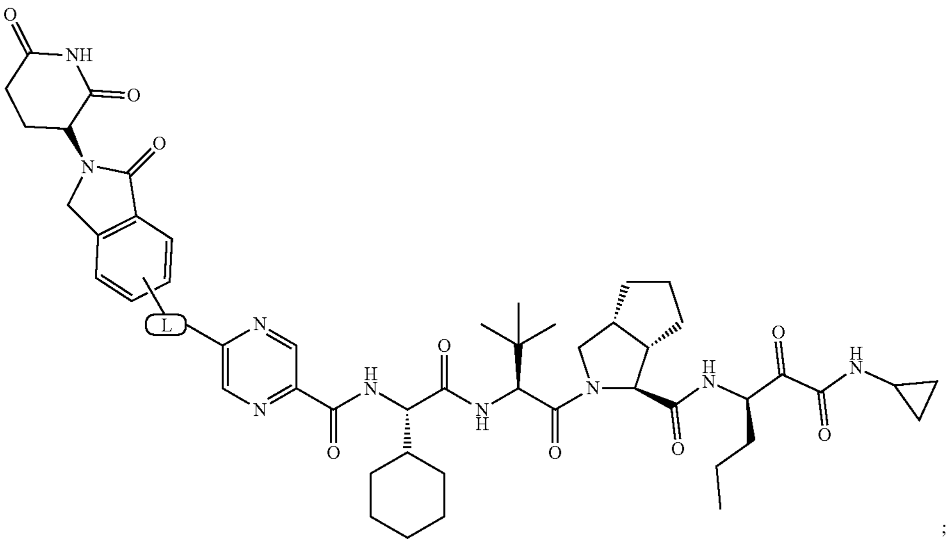
;

-continued
(dg20c)
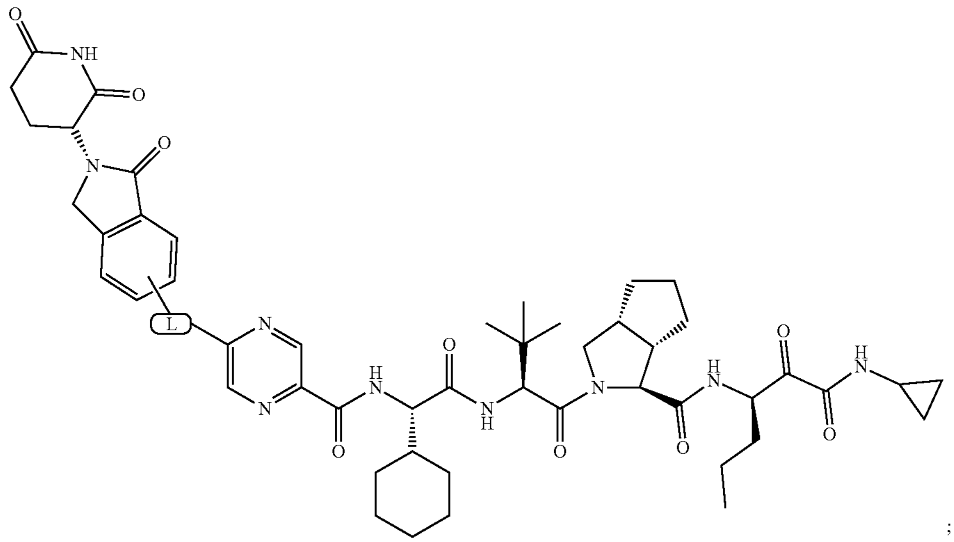
;
(dg21c)
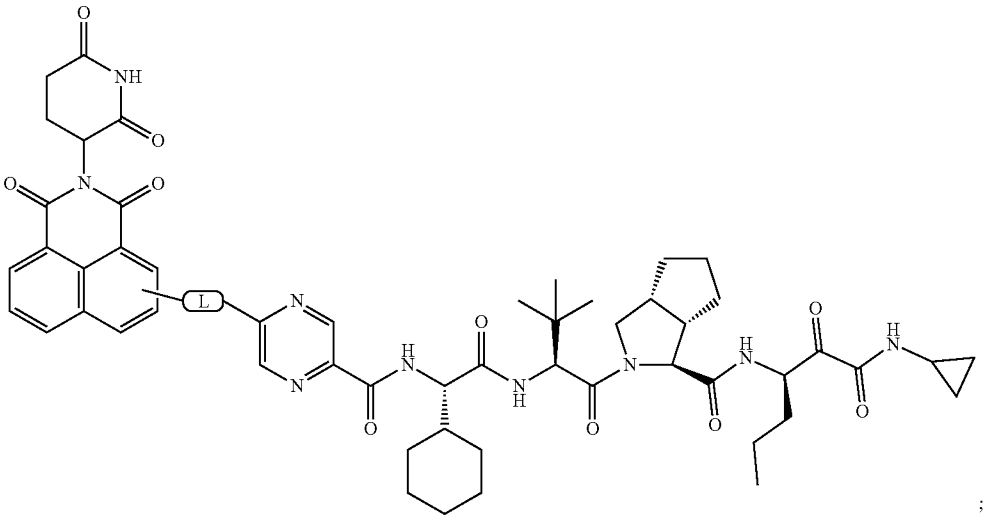
;
(dg22c)
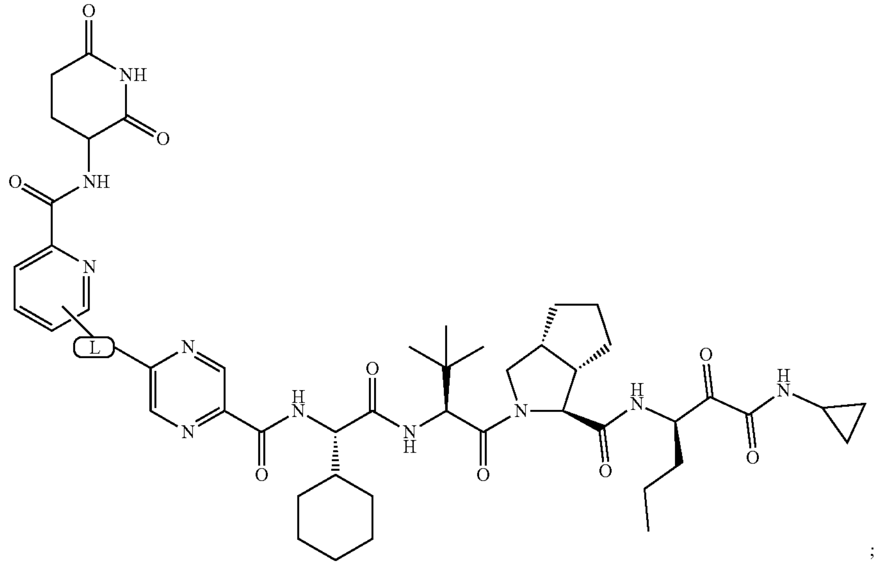
;

-continued
(dg17d)
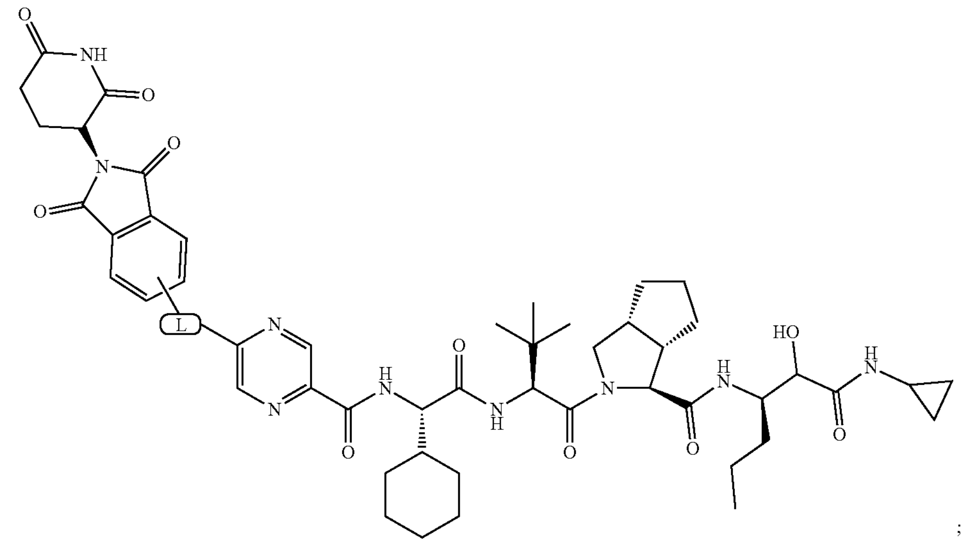
;
(dg18d)
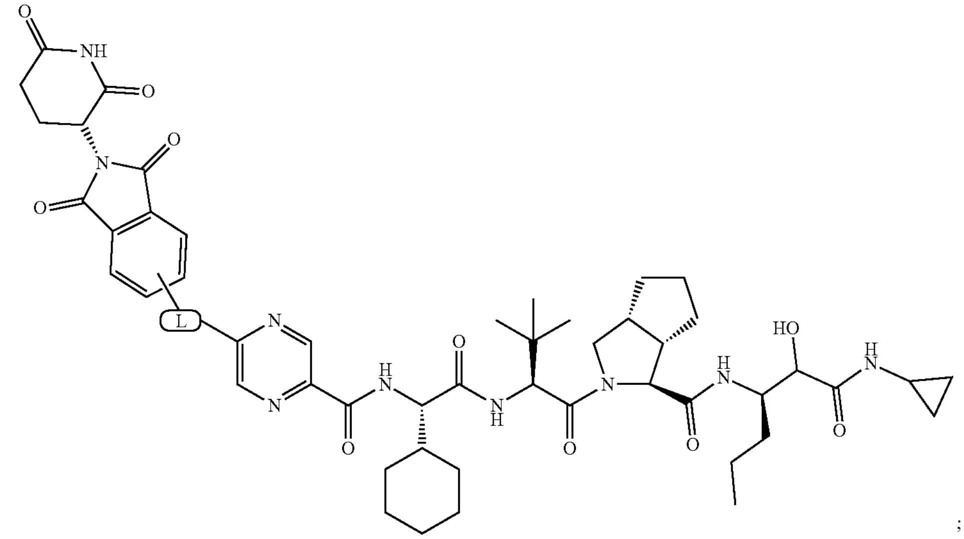
;
(dg19d)
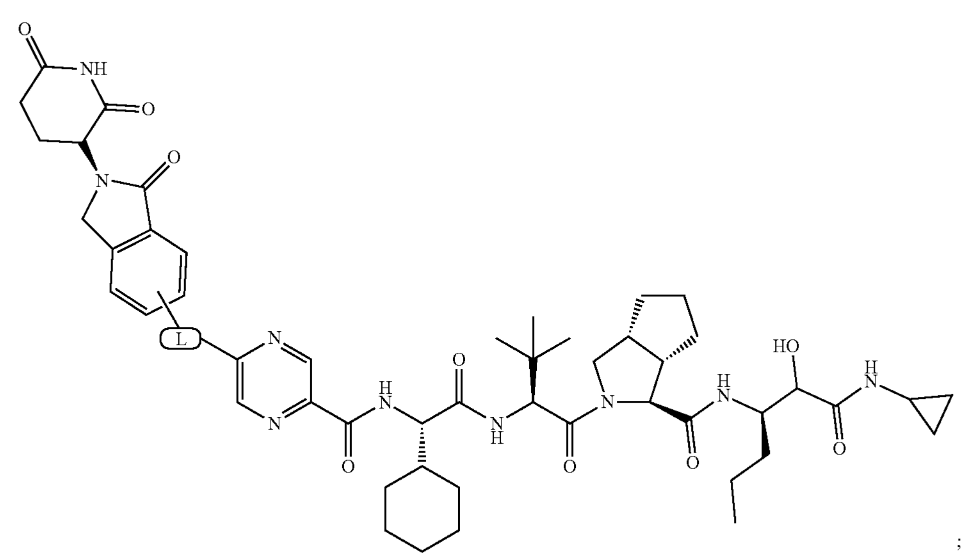
;

-continued
(dg20d)
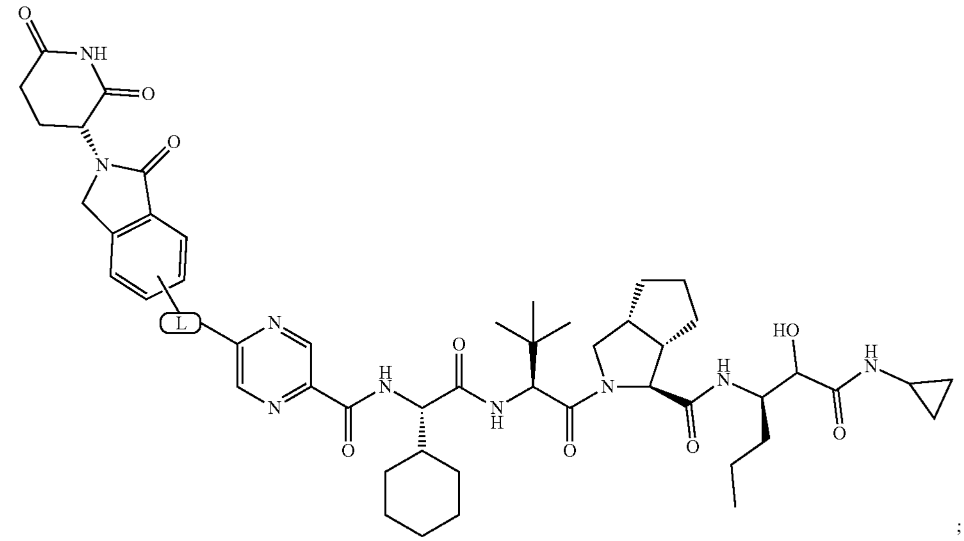
;
(dg21d)
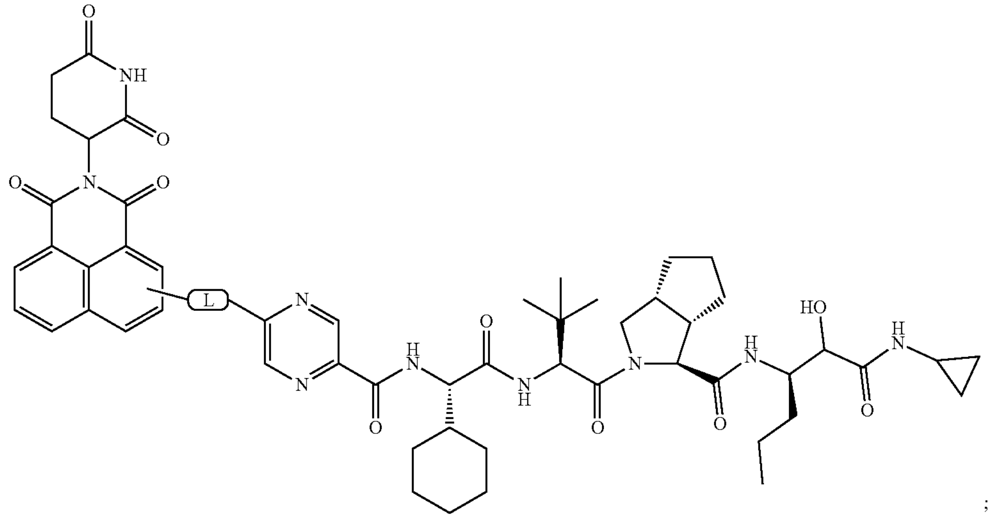
; and
(dg22d)
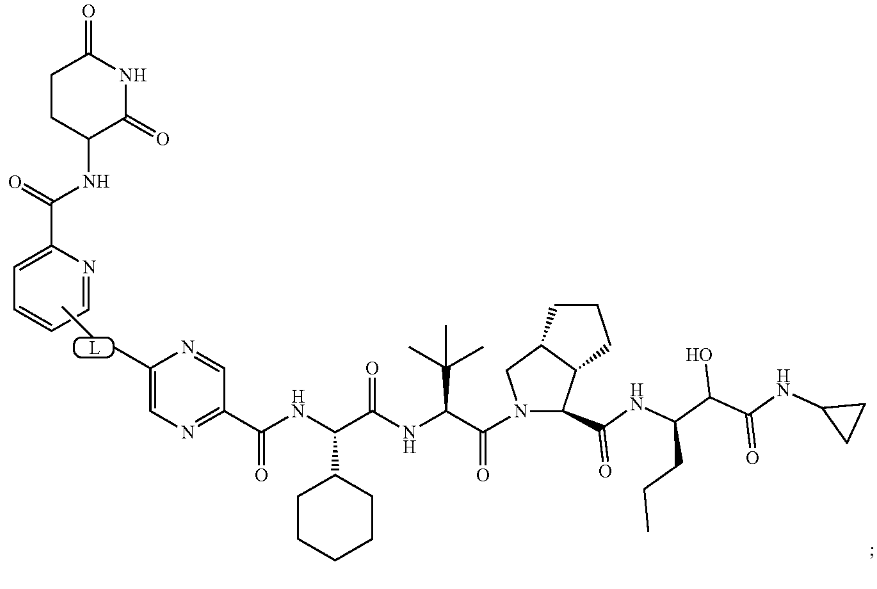
;

wherein R' is C—OH or C═O; or a pharmaceutically acceptable salt or stereoisomer thereof.
6. The bifunctional compound of claim 1, which is represented by a structure selected from the group consisting of:
(1)
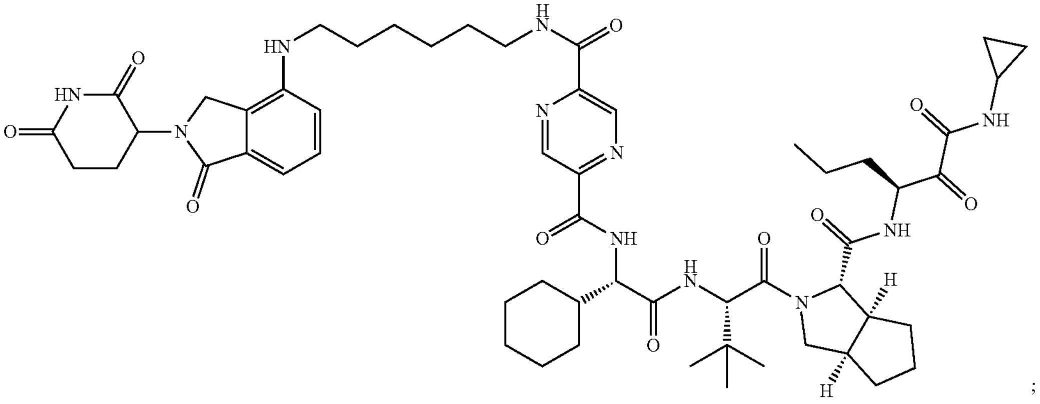
;
(2)
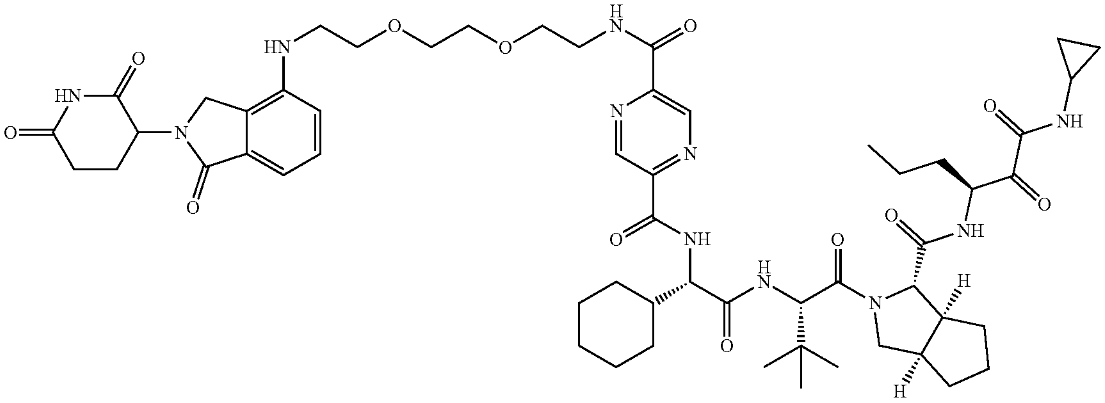
;
(3)
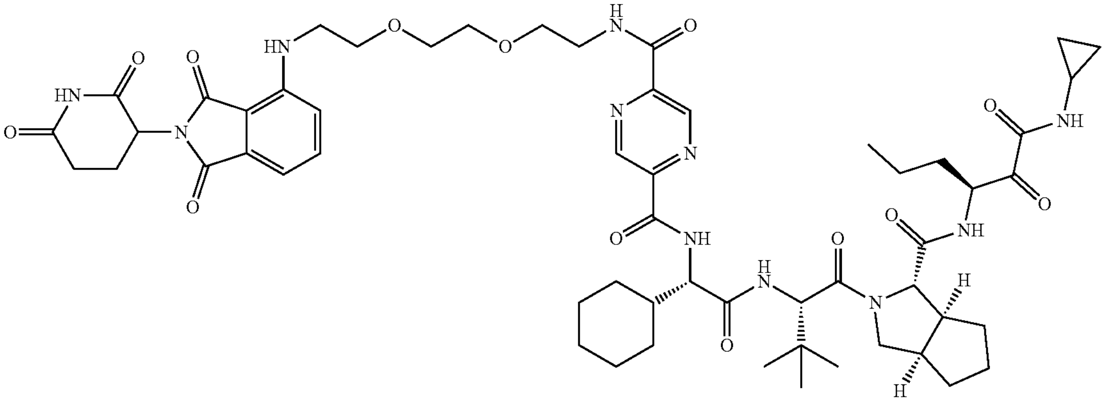
;

-continued
(4)
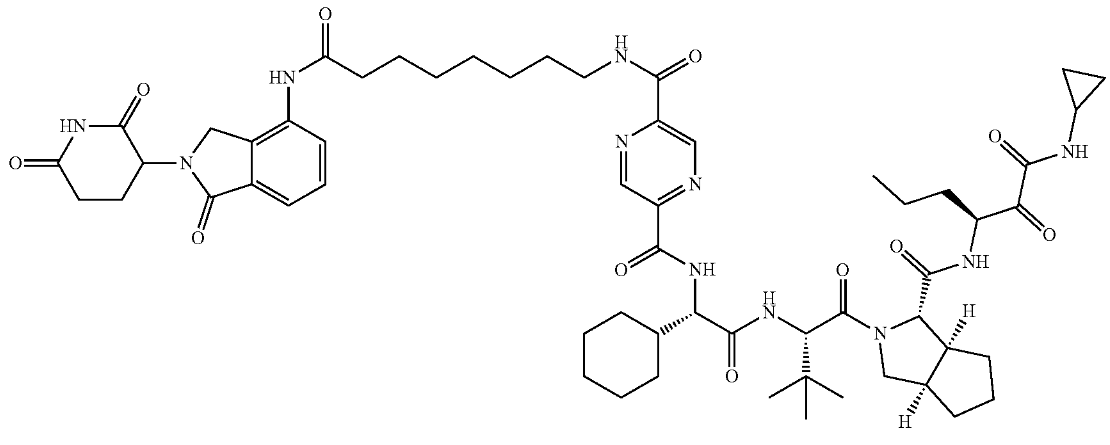
;
(5)
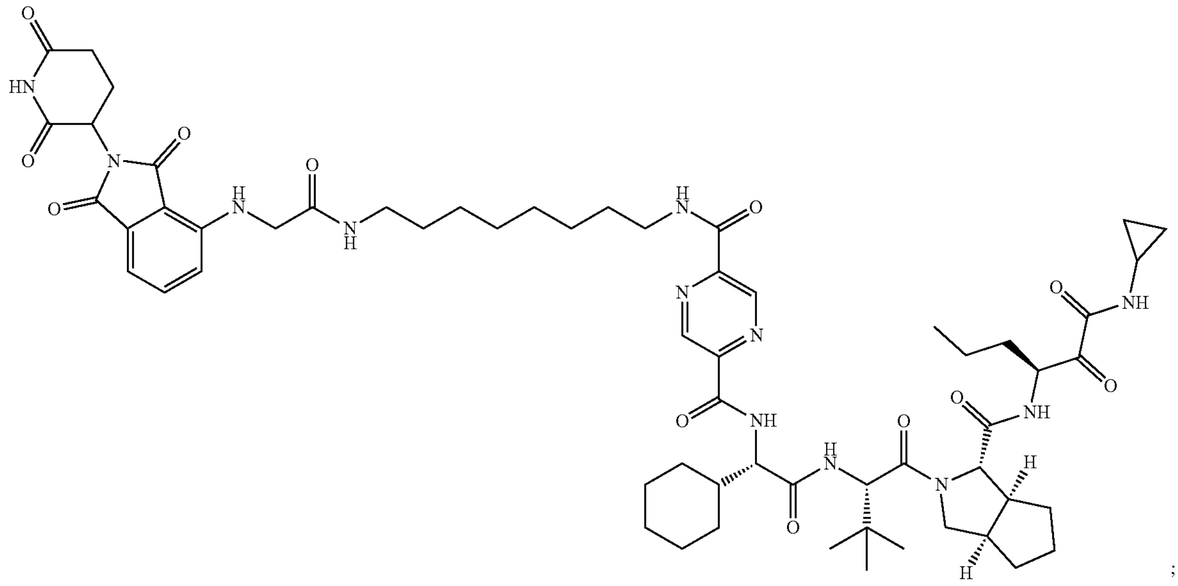
;
(6)
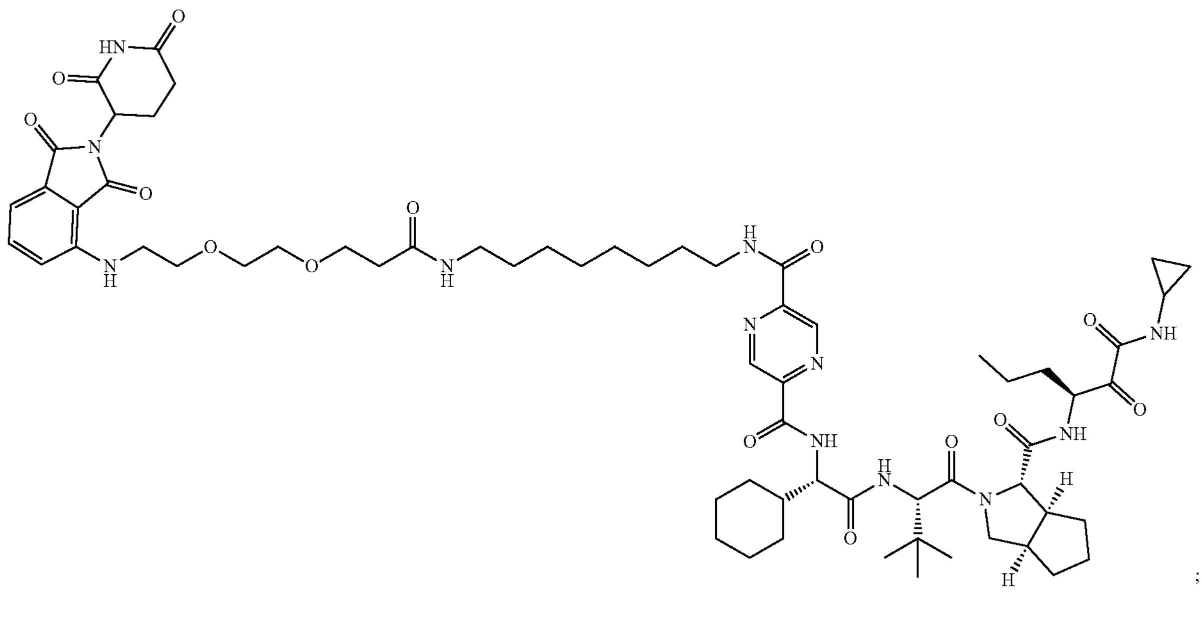
;

-continued
(7)
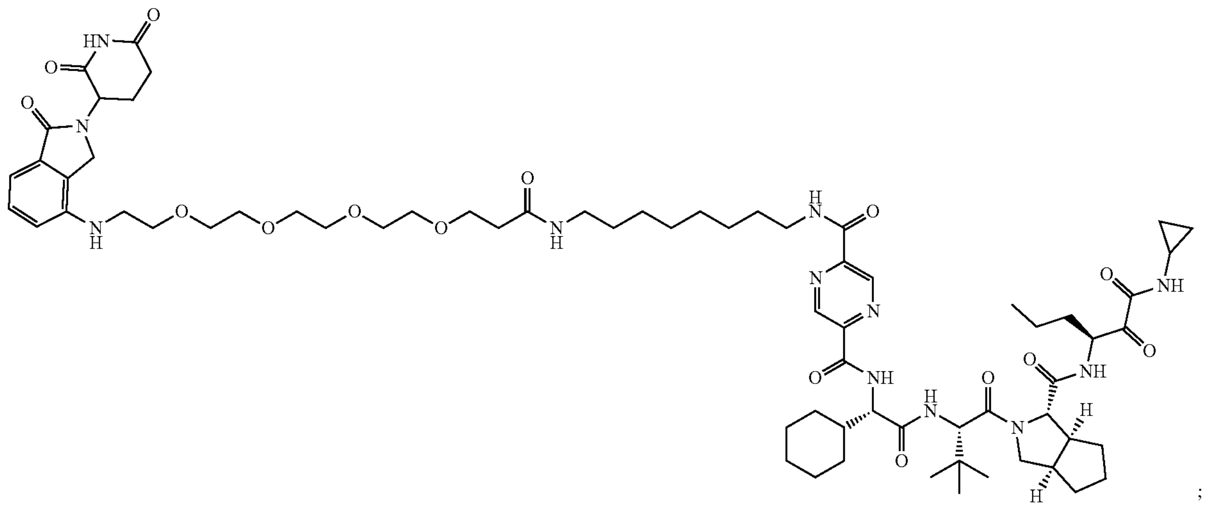
;
(8)
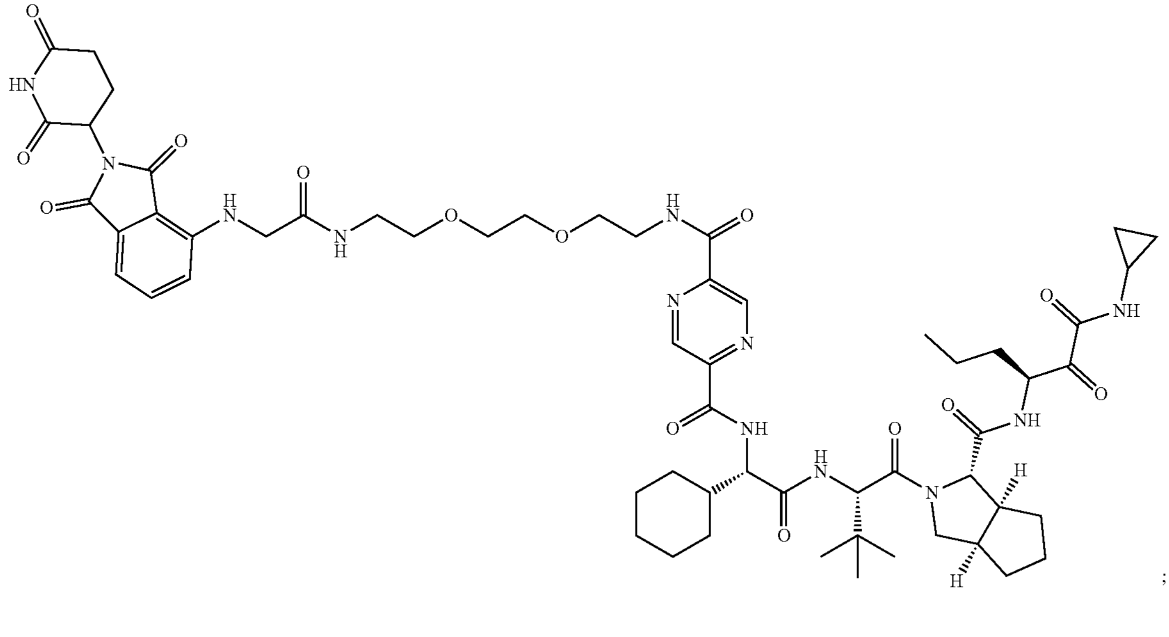
;

-continued
(9)
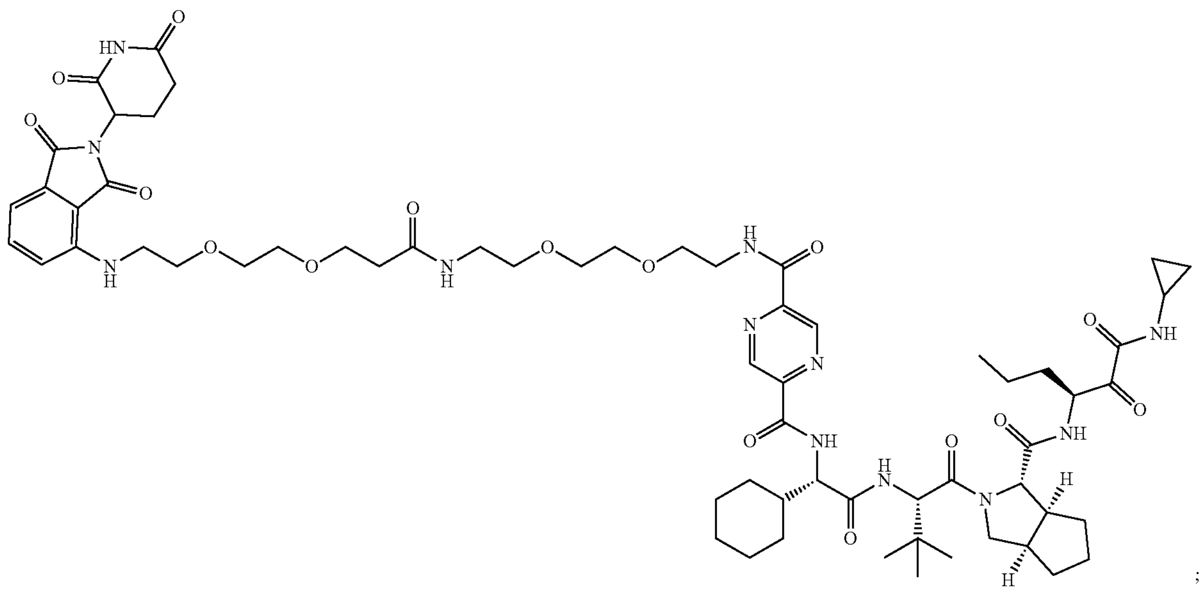
;
(10)
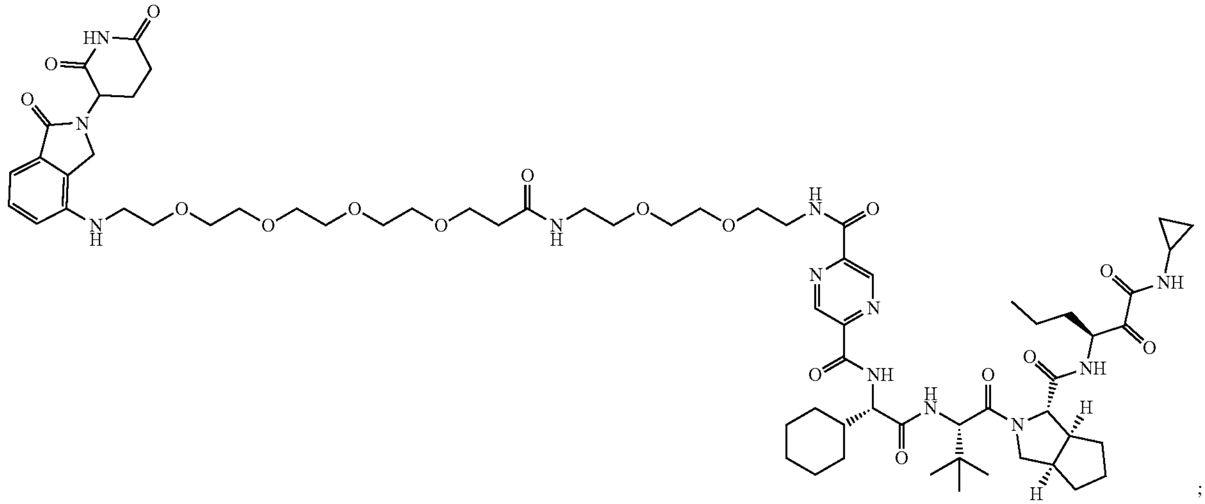
;
(12)
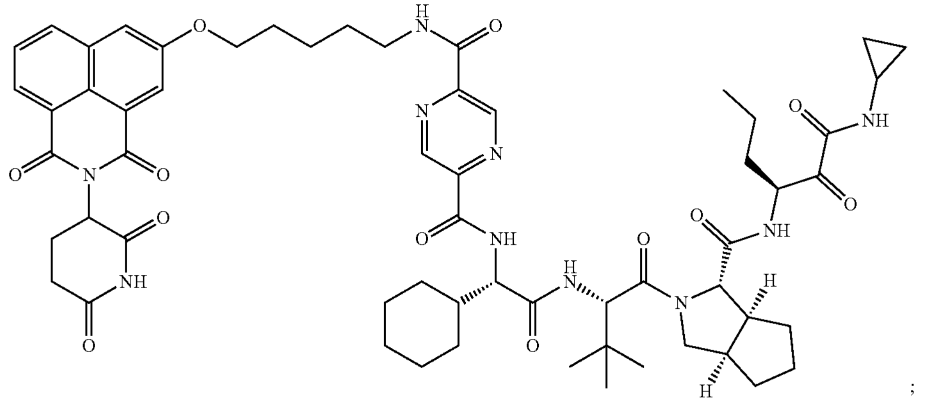
;

-continued
(13)
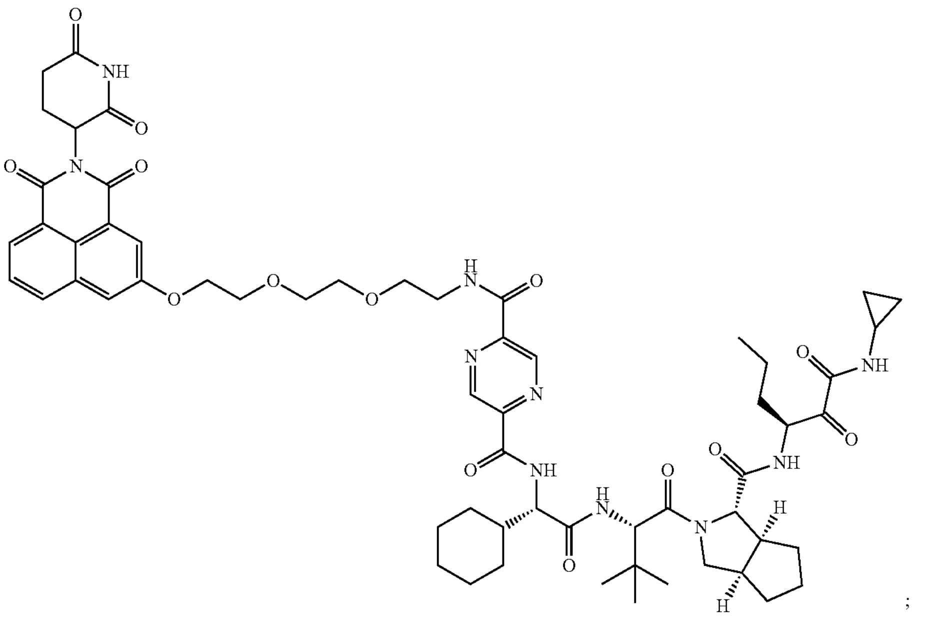
;
(14)
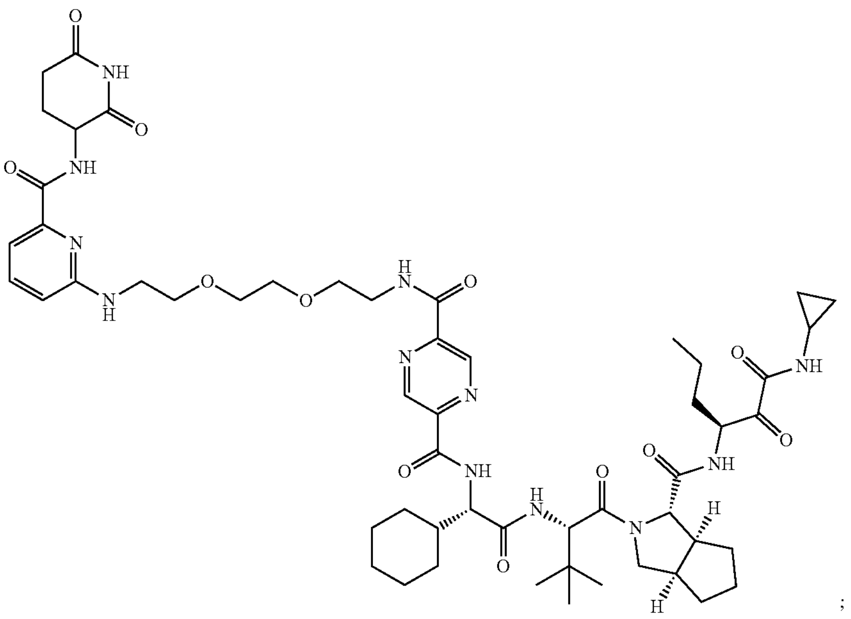
;

-continued
(15)
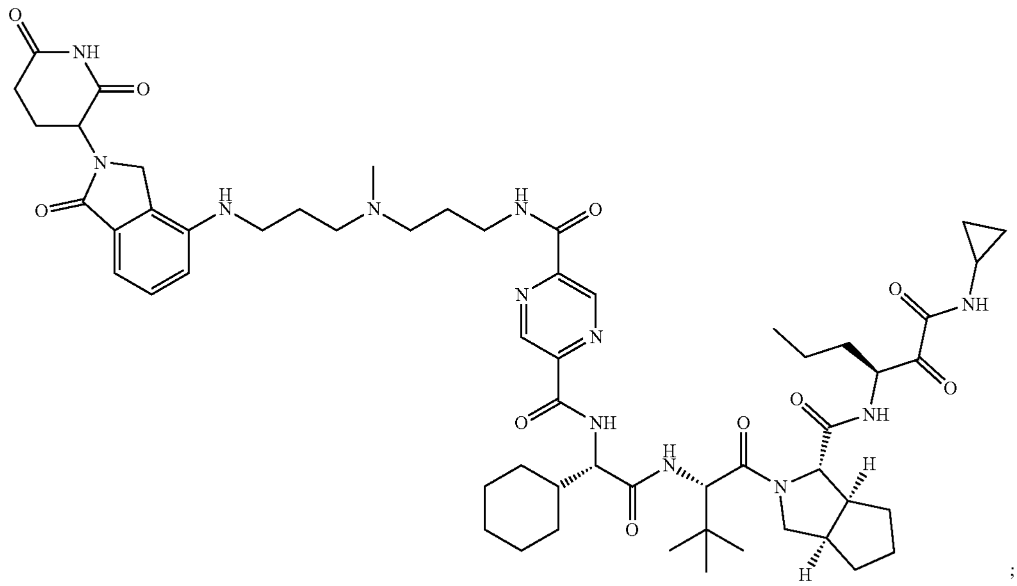
;
(16)
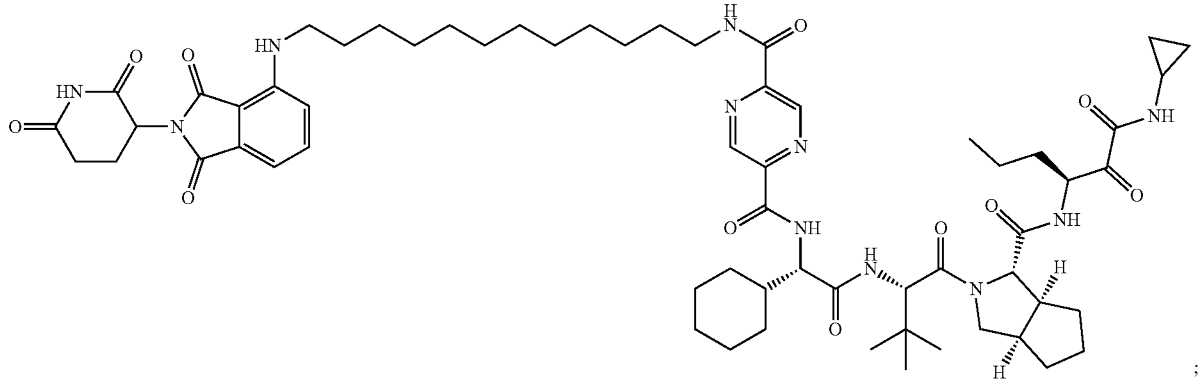
;
(17)
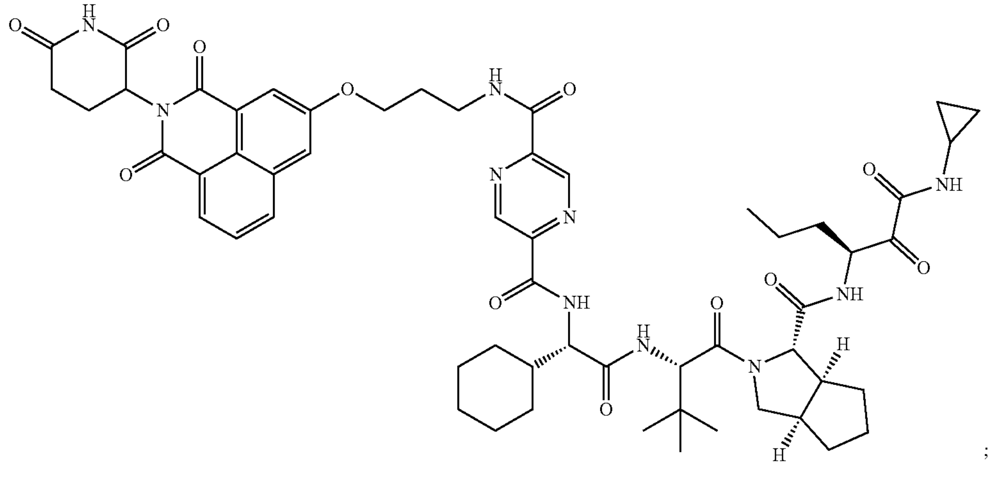
; and

-continued (18)

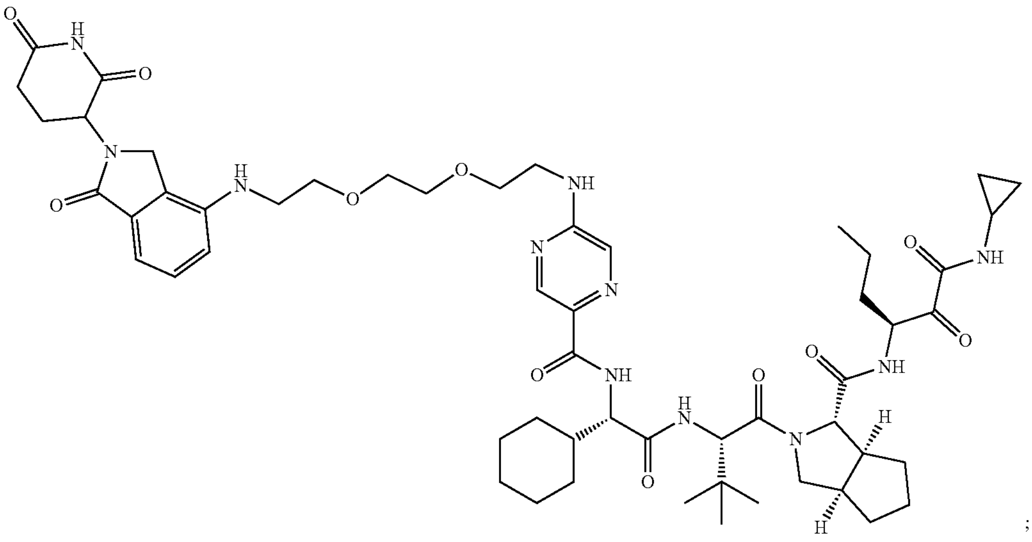

;

or a pharmaceutically acceptable salt or stereoisomer thereof.

7. A pharmaceutical composition comprising a therapeutically effective amount of the bifunctional compound of claim 1, or a pharmaceutically acceptable salt or stereoisomer thereof, and a pharmaceutically acceptable carrier.

8. A method of treating HCV infection, comprising administering a therapeutically effective amount of the bifunctional compound of claim 1, or a pharmaceutically acceptable salt or stereoisomer thereof, to a subject in need thereof.

9. The method of claim 8, wherein the subject has an HCV-associated disease or disorder, which is selected from the group consisting of hepatitis, cirrhosis, and liver cancer.

10. The bifunctional compound of claim 1, which is:

or a pharmaceutically acceptable salt or stereoisomer thereof.

11. A pharmaceutical composition comprising a therapeutically effective amount of the bifunctional compound of claim 10, or a pharmaceutically acceptable salt or stereoisomer thereof, and a pharmaceutically acceptable carrier.

12. A method of treating HCV infection, comprising administering a therapeutically effective amount of the bifunctional compound of claim 10, or a pharmaceutically acceptable salt or stereoisomer thereof, to a subject in need thereof.

13. The bifunctional compound of claim 1, wherein the NS3/4A targeting ligand is represented by structure:

(13)

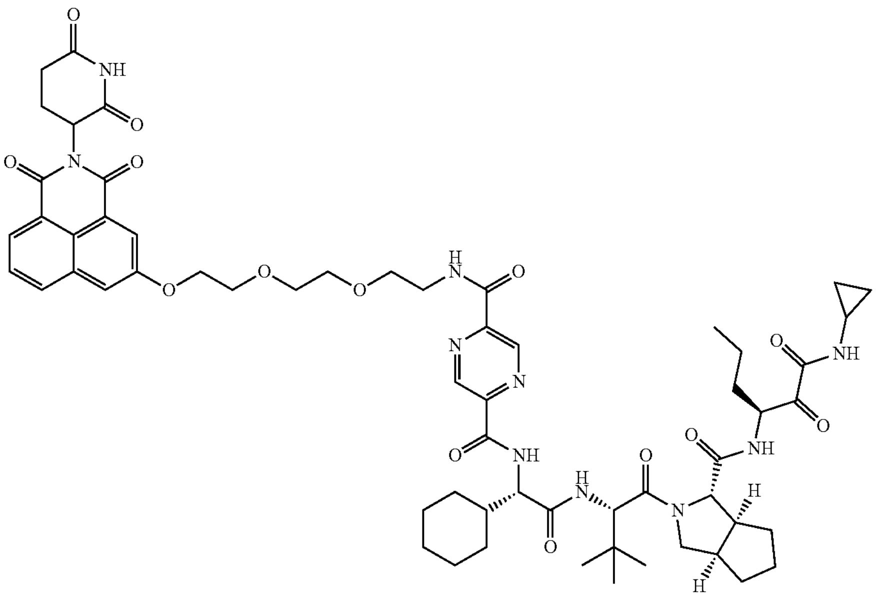

(TL1b)
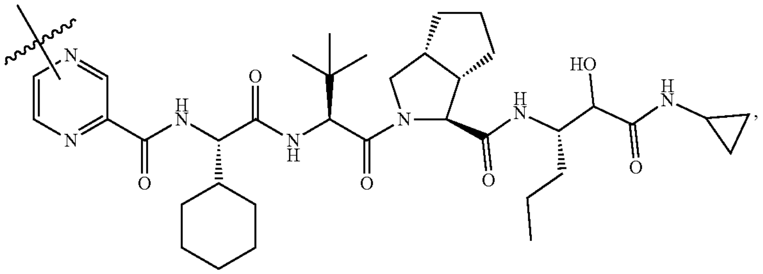
or a stereoisomer thereof.
14. The bifunctional compound of claim 1, wherein the NS3/4A targeting ligand is represented by structure:
(TL1c)
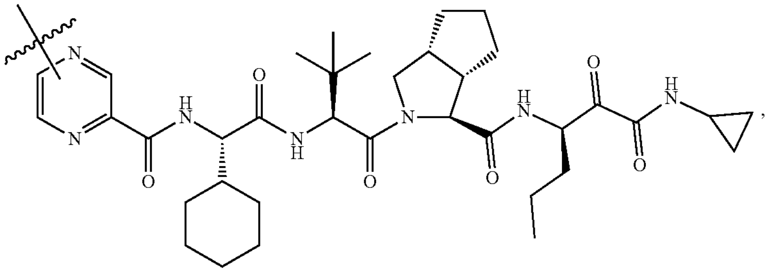
or a stereoisomer thereof.
15. The bifunctional compound of claim 1, wherein the NS3/4A targeting ligand is represented by structure:
(TL1d)
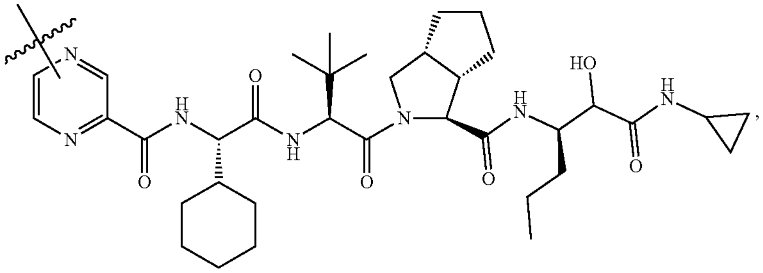
or a stereoisomer thereof.
* * * * *